United States Patent
Gundlach et al.

(10) Patent No.: US 12,321,837 B2
(45) Date of Patent: Jun. 3, 2025

(54) SYSTEMS AND METHODS FOR IMPROVED NANOPORE-BASED ANALYSIS OF NUCLEIC ACIDS

(71) Applicant: University of Washington, Seattle, WA (US)

(72) Inventors: Jens H. Gundlach, Seattle, WA (US); Matthew Noakes, Seattle, WA (US); Henry D. Brinkerhoff, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 905 days.

(21) Appl. No.: 17/430,695

(22) PCT Filed: Feb. 14, 2020

(86) PCT No.: PCT/US2020/018426
§ 371 (c)(1),
(2) Date: Aug. 12, 2021

(87) PCT Pub. No.: WO2020/168286
PCT Pub. Date: Aug. 20, 2020

(65) Prior Publication Data
US 2022/0366313 A1 Nov. 17, 2022

Related U.S. Application Data

(60) Provisional application No. 62/805,870, filed on Feb. 14, 2019.

(51) Int. Cl.
*G06N 20/10* (2019.01)
*C12Q 1/6869* (2018.01)
(Continued)

(52) U.S. Cl.
CPC ........... *G06N 20/10* (2019.01); *C12Q 1/6869* (2013.01); *G01N 33/48721* (2013.01); *G06N 20/20* (2019.01)

(58) Field of Classification Search
CPC ........... G01N 33/48721; C12Q 1/6869; G06N 20/20; G06N 20/10
See application file for complete search history.

(56) References Cited

U.S. PATENT DOCUMENTS 6,413,792 B1    7/2002  Sauer
8,452,546 B1 *  5/2013  Lathrop ........... G01N 33/48721
                                                  435/6.1

(Continued)

FOREIGN PATENT DOCUMENTS

WO    2007041621 A2    4/2007
WO    2013014451 A1    1/2013

(Continued)

OTHER PUBLICATIONS

Butler et al., Single-Molecule DNA Detection with an Engineered MspA Protein Nanopore, Proc. Natl. Acad. Sci. U.S.A, vol. 105, No. 52, Dec. 30, 2008, pp. 20647-20652 (Year: 2008).*

(Continued)

*Primary Examiner* — Natalie Huls
*Assistant Examiner* — Nyla Gavia
(74) *Attorney, Agent, or Firm* — Christensen O'Connor Johnson Kindness PLLC

(57) ABSTRACT

In some embodiments, a computer-implemented method of determining an identity of one or more monomer subunit residues of a polymer analyte is provided, In some embodiments, a raw current signal generated by using a variable voltage to translocate the polymer analyte through a nanopore. In some embodiments, change points are detected in the raw current signal to determine a series of states, In some (Continued)

embodiments, capacitance compensation is performed on the raw current signal for each state to create an ionic current-vs-voltage curve for each state. In some embodiments, the ionic current-vs-voltage curves is converted to conductance-vs-voltage curves. In some embodiments, filtering is performed for the series of states to create a series of filtered states. In some embodiments, the identity of one or more monomer subunit residues of the polymer analyte is determined based on the series of filtered states.

20 Claims, 36 Drawing Sheets

Specification includes a Sequence Listing.

(51) Int. Cl.
   *G01N 33/487* (2006.01)
   *G06N 20/20* (2019.01)

(56) References Cited

U.S. PATENT DOCUMENTS

| | | | |
|---|---|---|---|
| 8,986,928 | B2 | 3/2015 | Turner |
| 9,377,437 | B2 | 6/2016 | Chen |
| 9,605,307 | B2 | 3/2017 | Chen |
| 9,927,397 | B1 | 3/2018 | Brueck |
| 2009/0054919 | A2* | 2/2009 | Winters-Hilt ...... A61B 5/15128 606/167 |
| 2009/0177612 | A1 | 7/2009 | Gorham |
| 2011/0226623 | A1* | 9/2011 | Timp .................. C12Q 1/6869 204/543 |
| 2013/0146457 | A1* | 6/2013 | Gundlach ........ G01N 27/44704 977/924 |
| 2013/0204319 | A1* | 8/2013 | Trier .................. A61N 1/36146 607/46 |
| 2013/0341192 | A1* | 12/2013 | Dunbar ............ G01N 33/48728 204/601 |
| 2014/0221216 | A1* | 8/2014 | Cope ...................... G16B 15/00 506/1 |
| 2014/0266147 | A1 | 9/2014 | Blick |
| 2014/0333775 | A1 | 11/2014 | Naikal |
| 2015/0360194 | A1* | 12/2015 | Bustamante ......... C12Q 1/6809 506/26 |
| 2016/0222444 | A1* | 8/2016 | Gundlach ............ C12Q 1/6869 |
| 2017/0058337 | A1* | 3/2017 | Clarke ................. C12Q 1/6869 |
| 2017/0199149 | A1* | 7/2017 | Gundlach ........ G01N 33/48721 |
| 2018/0223351 | A1 | 8/2018 | Davis |
| 2018/0362594 | A1 | 12/2018 | Cech |
| 2019/0227050 | A1 | 7/2019 | Brueck |
| 2019/0310242 | A1 | 10/2019 | Reid |

FOREIGN PATENT DOCUMENTS

| | | | | |
|---|---|---|---|---|
| WO | 2013159042 | A1 | 10/2013 | |
| WO | WO-2014071250 | A1 * | 5/2014 | ........... C12Q 1/6827 |
| WO | 2015051378 | | 4/2015 | |
| WO | 2017125565 | A1 | 7/2017 | |
| WO | 2018218787 | A1 | 12/2018 | |
| WO | 2019057890 | A1 | 3/2019 | |

OTHER PUBLICATIONS

Craig, J. M. et al. Revealing dynamics of helicase translocation on singlestranded DNA using high-resolution nanopore tweezers. Proc. Natl Acad. Sci. 114, 11932-11937 (2017).

David, M. et al. Nanocall: an open source basecaller for Oxford Nanopore sequencing data. Bioinformatics 33, 49-55 (2017).

Deamer, D. et al. Three decades of nanopore sequencing. Nature Biotechnology. 34, 518-524 (2016).

Derrington, I. M. et al. Subangstrom single-molecule measurements of motor proteins using a nanopore. Nat. Biotechnol. 33, 1073-1075 (2015).

Derrington, I. M. et al., Nanopore DNA sequencing with MspA, Proc Natl, Sci USA Sep. 14, 2010: 107(37):16060-5.

Faria, N. R. et al. Establishment and cryptic transmission of Zika virus in Brazil and the Americas. Nature 546, 406-410 (2017).

Goodwin, S. et al. Oxford Nanopore sequencing, hybrid error correction, and de novo assembly of a eukaryotic genome. Genome Research. 25, 1750-1756 (2015).

Jain, M. et al. MinION analysis and reference consortium: phase 2 data release and analysis of R9.0 chemistry. F1000Res. 6, 760 (2017).

Jain, M. et al. Nanopore sequencing and assembly of a human genome with ultra-long reads. Nat. Biotechnol. 36, 338-345 (2018).

Kafetzopoulou, L. E. et al. Assessment of Metagenomic MinION and Illumina sequencing as an approach for the recovery of whole genome sequences of chikungunya and dengue viruses directly from clinical samples. bioRxiv. Jun. 25, 2018.

Kasianowicz, J. J., Brandin, E., Branton, D. & Deamer, D. W. Characterization of individual polynucleotide molecules using a membrane channel. Proc. Natl Acad. Sci. 93, 13770-13773 (1996).

Krishnakumar, R. et al. Systematic and stochastic influences on the performance of the MinION nanopore sequencer across a range of nucleotide bias. Sci. Rep. 8, 3159 (2018).

Laszlo, A. H. et al. Decoding long nanopore sequencing reads of natural DNA. Nat. Biotechnol. 32, 829-833 (2014).

Laszlo, A. H. et al. Detection and mapping of 5-methylcytosine and 5-hydroxymethylcytosine with nanopore MspA. Proc. Natl Acad. Sci. 110, 18904-18909 (2013).

Laszlo, A. H., Derrington, I. M. & Gundlach, J. H. MspA nanopore as a single-molecule tool: from sequencing to SPRNT. Methods 105, 75-89 (2016).

Lathrop, D. K. et al. Monitoring the Escape of DNA from a Nanopore Using an Alternating Current Signal. J. Am. Chem. Soc. 132, 6, 1878-1885 (2010).

Loman, N. J., Quick, J. & Simpson, J. T. A complete bacterial genome assembled de novo using only nanopore sequencing data. Nat. Methods 12, 733-735 (2015).

Lu, H. et al. Oxford Nanopore MinION Sequencing and Genome Assembly. Genomics, Proteomics & Bioinformatics, 14, 5, 265-279 (2016).

Manrao, E. A. et al. Reading DNA at single-nucleotide resolution with a mutant MspA nanopore and phi29 DNA polymerase. Nat. Biotechnol. 30, 349-353 (2012).

Manrao, E. A., Derrington, I. M., Pavlenok, M., Niederweis, M. & Gundlach, J. H. Nucleotide discrimination with DNA immobilized in the MspAnanopore. PLoS One 6, e25723 (2011).

McFarland, H. L. et al. First-Principles Investigation of Nanopore Sequencing Using Variable Voltage Bias on Graphene-Based Nanoribbons. J. Phys. Chem. Lett. 6 (13) 2616-2621 (2015).

Noakes, M .T., et al. Increasing the accuracy of nanopore DNA sequencing using a time-varying cross membrane voltage. Nature Biotechnology 37, 651-656 (2019).

Pomerantz, A. et al. Real-time DNA barcoding in a rainforest using nanopore sequencing: opportunities for rapid biodiversity assessments and local capacity building. GigaScience 7, giy033 (2018).

Quick, J. et al. Rapid draft sequencing and real-time nanopore sequencing in a hospital outbreak of *Salmonella*. Genome Biol. 16, 114 (2015).

Quick, J. et al. Real-time, portable genome sequencing for Ebola surveillance. Nature 530, 228-232 (2016).

Rames, E. & Macdonald, J. Evaluation of MinION nanopore sequencing for rapid enterovirus genotyping. Virus Res. 252, 8-12 (2018).

Rand, A. C. et al. Mapping DNA methylation with high-throughput nanopore sequencing. Nat. Methods 14, 411-413 (2017).

Rang, F. J., Kloosterman, W. P. & de Ridder, J. From squiggle to basepair: computational approaches for improving nanopore sequencing read accuracy. Genome Biol. 19, 90 (2018).

Schreiber, J. et al. Error rates for nanopore discrimination among cytosine, methylcytosine, and hydroxymethylcytosine along individual DNA strands. Proc. Natl Acad. Sci. USA 110, 18910-18915 (2013).

(56) References Cited

OTHER PUBLICATIONS

Sigalov et al. Detection of DNA Sequences Using an Alternating Electric Field in a Nanopore Capacitor. Nano Lett. 8, 1, 56-63 (2008).

Simpson, J. Signal-level algorithms for MinION data. Github https://github.com/jts/nanopolish (2018).

Simpson, J. T. et al. Detecting DNA cytosine methylation using nanopore sequencing. Nat. Methods 14, 407-410 (2017).

Sovic, I. et al. Fast and sensitive mapping of nanopore sequencing reads with GraphMap. Nature Communications. 7 (2016).

Szalay, T. et al. De novo sequencing and variant calling with nanopores using PoreSeq. Nature Biotechnology. 33, 1087-1091 (2015).

Teng, H. et al. Chiron: translating nanopore raw signal directly into nucleotide sequence using deep learning. GigaScience 7, giy037 (2018).

Theuns, S. et al. Nanopore sequencing as a revolutionary diagnostic tool for porcine viral enteric disease complexes identifies porcine kobuvirus as an important enteric virus. Sci. Rep. 8, 9830 (2018).

Vaser, R., Sovic, I., Nagarajan, N. & Sikic, M. Fast and accurate de novo genome assembly from long uncorrected reads. Genome Res. https://doi.org/10.1101/gr.214270.116 (2017).

Wang, Y. et al. The evolution of nanopore sequencing. Frontiers in Genetics. vol. 5, 1-20 (2015).

International Search Report and Written Opinion mailed on Jun. 8, 2020, issued in corresponding International Application No. PCT/US2020/018426, filed Feb. 14, 2020, 40 pages.

Bayley, H., "Nanopore Sequencing: From Imagination to Reality," Clinical Chemistry 61:1, pp. 25-31, 2015.

Bhattacharya, et al., "Molecular Dynamics Study of MspA Arginine Mutants Predicts Slow DNA Translocations and Ion Current Blockades Indicative of DNA Sequence," ACSNano, vol. 6, No. 8, pp. 6960-6968, 2012.

Bleidorn, C., "Third Generation Sequencing: Technology and Its Potential Impact on Evolutionary Biodiversity Research," Systematics and Biodiversity, 14:1, pp. 1-8, 2016.

Boza, et al., "Deepnano: Deep Recurrent Neural Networks for Base Calling in Minion Nanopore Reads," Plos One, pp. 1-13, 2017.

Branton, et al., "The potential and challenges of nanopore sequencing," Nature Biotechnology, vol. 26, No. 10, pp. 1146-1153, Oct. 2008.

Brinkerhoff, H., " Getting The Most Out Of A Nanopore," University of Washington, 2018.

Bronzato Badial, A., et al., "Nanopore Sequencing as A Surveillance Tool for Plant Pathogens in Plant and Insect Tissues," Plant Disease, vol. 102, No. 8, pp. 1648-1652, Aug. 2018.

Butler, et al., "Single-Molecule DNA Detection With An Engineered Mspa Protein Nanopore, " PNAS, vol. 105, No. 52, pp. 20647-20652, Dec. 30, 2008.

Cao, et al., "Streaming Algorithms For Identification of Pathogens And Antibiotic Resistance Potential from Real-Time Miniontm Sequencing," GigaScience, (2016) 5:32, pp. 1-16.

Castro-Wallace, S. L., et al., "Nanopore DNA Sequencing and Genome Assembly on the International Space Station," Scientific Report, (2017) 7:18022, pp. 1-12.

Cherf, et al., "Automated Forward And Reverse Ratcheting of DNA in A Nanopore at 5-Å Precision," Nature Biotechnology, vol. 30, No. 4, pp. 344-348, Apr. 2012.

Craig, et al., "Direct Detection of Unnatural DNA Nucleotides dNaM and d5SICS Using the MspA Nanopore," Plos One, pp. 1-9, Nov. 20, 2015.

\* cited by examiner (a)

Constant voltage

| Called Base | A | C | G | T | del |
|---|---|---|---|---|---|
| A | 77.2 | 6.6 | 6.1 | 2.6 | 7.5 |
| C | 6.7 | 73 | 5.2 | 5.3 | 9.8 |
| G | 7.9 | 5.8 | 70.4 | 6 | 9.9 |
| T | 1.9 | 3.6 | 6 | 81.6 | 6.9 |
| ins | 19.6 | 17.1 | 20 | 16.1 | 0 |

(b)

Variable voltage

| Called Base | A | C | G | T | del |
|---|---|---|---|---|---|
| A | 85.8 | 2.9 | 3.2 | 0.7 | 7.4 |
| C | 4 | 81.9 | 2.2 | 2.8 | 9.2 |
| G | 5.2 | 2.9 | 78.1 | 3.9 | 9.9 |
| T | 0.5 | 1 | 1.8 | 91.1 | 5.6 |
| ins | 6.2 | 6.4 | 6.6 | 5.5 | 0 |

FIG. 3A

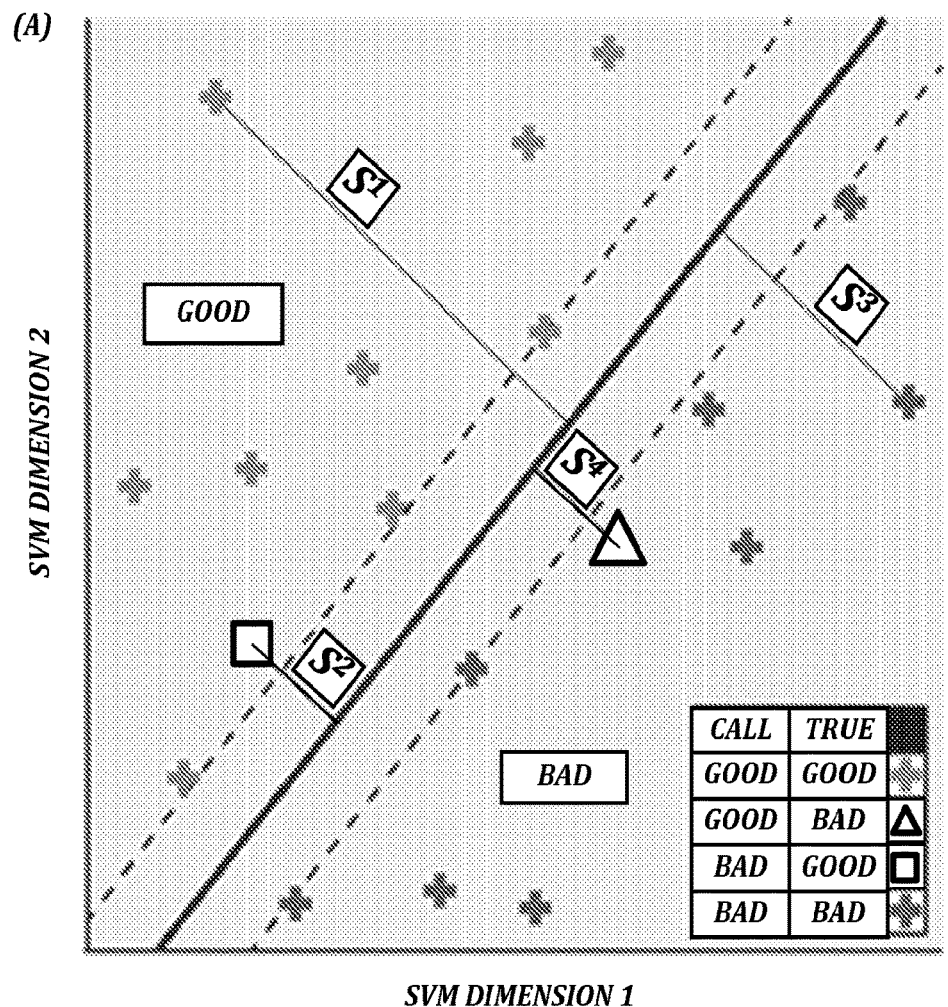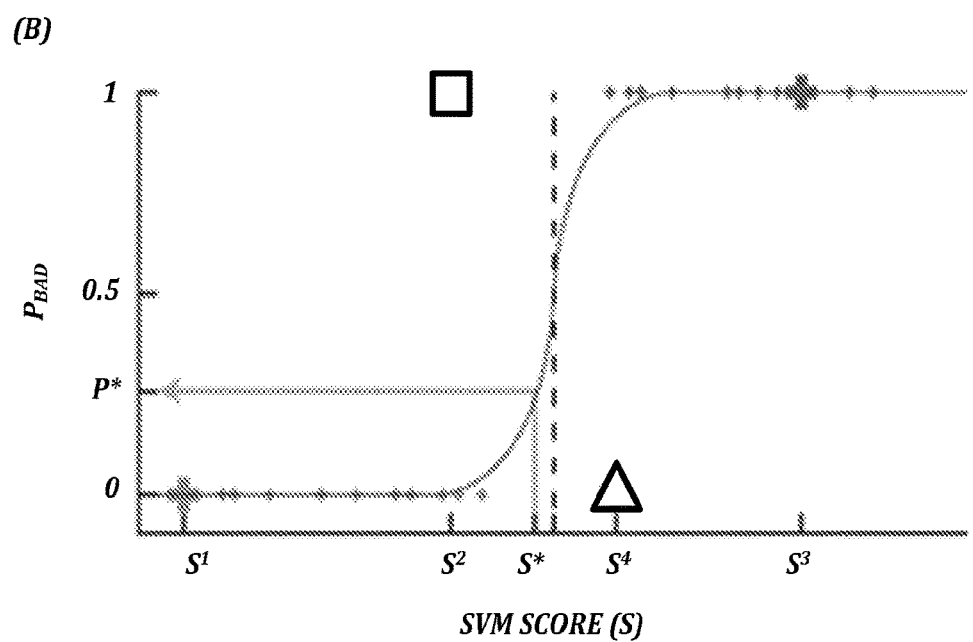
FIG. 20

| From \ To | i-4 | i-3 | i-2 | i-1 | new via step | new via skip | new via back |
|---|---|---|---|---|---|---|---|
| i-4 | S | K | K+K₊ | K+2K₊ | S+P_SA | K+P_SA | -- |
| i-3 | H | S | K | K+K₊ | S+P_SA | K+P_SA | -- |
| i-2 | B | H | S | K | S+P_SA | K+P_SA | -- |
| i-1 | B+B₊ | B | H | S | S+P_SA | K+P_SA | -- |
| new via step | B+2B₊ | B+B₊ | B | H | S+P_SA | K+P_SA | -- |
| new via skip | B+2B₊ | B+B₊ | B | H | S+P_SA | K+P_SA | B+P_SA |
| new via back | B+2B₊ | B+B₊ | B | H | -- | K+P_SA | -- |

FIG. 22

| 1 | Input:<br>$d$-dimensional data $\{x_i\}, i \in \{1:N\}$<br>Transition threshold $\mathcal{T}$ | |
|---|---|---|
| 2 | Initialize: $\{t\} \leftarrow [\ ]$ | Initialize an empty list of transition points |
| 3 | function PARTITION($\{x_i\}, \mathcal{T}, \{t\}$) | |
| 4 |    Score: assign a score $\mathcal{S}_i$ for the placement of a transition at each point $i \in \{1:N\}$ | |
| 5 |    $\mathcal{S}_{best} \leftarrow max(\{\mathcal{S}_i\})$ | |
| 6 |    $t_{best} \leftarrow i$ such that $\mathcal{S}_i = \mathcal{S}_{best}$ | |
| 7 |    if $\mathcal{S}_{best} > \mathcal{T}$) then | The best transition point is good enough to call a transition |
| 8 |       $\{t\}[end] \leftarrow t_{best}$ | Add the found transition to the growing list |
| 9 |       $\{t\} \leftarrow$ PARTITION($\{x_i\}, i \in \{1:t_{best}\}, \mathcal{T}, \{t\}$) | Recursively find partitions in the data to the left of the found transition point |
| 10 |       $\{t\} \leftarrow$ PARTITION($\{x_i\}, i \in \{t_{best}:N\}, \mathcal{T}, \{t\}$) | Recursively find partitions in the data to the right of the found transition point |
| 11 |    else | |
| 12 |       Output: $\{t\}$ | |
| 13 |    end if | |
| 14 | end function | |

*FIG. 26*

| 1 | assume we start with $N$ states $\{\mathbf{x}^i\}_{i \in 1:N}$ | |
|---|---|---|
| 2 | $stop \leftarrow false$ | |
| 3 | while $\sim stop$ do | |
| 4 | $anyremoved \leftarrow false$ | |
| 5 | calculate the SVM feature vectors $\{\xi^i\}_{i \in 2:N-1}$ from the states $\{\mathbf{x}^i\}_{i \in 1:N}$ | |
| 6 | calculate the bad state probabilities $\{P_{bad}^i\}_{i \in 2:N-1}$ from the SVM feature vectors $\{\xi^i\}_{i \in 2:N-1}$ | |
| 7 | for $j \in 2:N-1$ do | |
| 8 | if $P_{bad}^i > T_{thresh}$ then | |
| 9 | remove $\mathbf{x}^j$ from $\{\mathbf{x}^i\}$ | Remove states above the removal threshold |
| 10 | $anyremoved \leftarrow true$ | Stop iterating if nothing is removed |
| 11 | end if | |
| 12 | end for | |
| 13 | if $\sim anyremoved$ then | |
| 14 | $stop \leftarrow true$ | |
| 15 | end if | |
| 16 | end while | |
| 17 | remove $\mathbf{x}^1$ and $\mathbf{x}^N$ from $\{\mathbf{x}^i\}$ | Remove the first and last states |

FIG. 27

| 1 | Input: start with $N$ observed states $\{\mathbf{x}^i\}$, $i \in 1:N$ | States are passed in after removal filter |
|---|---|---|
| 2 | function STEPPROBS($\{x^i\}$) | Function to calculate the transition-by-transition step-type probabilities |
| 3 | Calculate Get the scores $\mathbb{S}_{SK}$, $\mathbb{S}_{SB}$, and $\mathbb{S}_{SH}$ from the SVMs $S_{SK}$, $S_{SB}$, and $S_{SH}$ | |
| 4 | Calculate Convert SVM scores into relative likelihoods using the attached logit functions | |
| 5 | Solve Use the resulting system of 4 equations to find $P_S$, $P_B$, $P_H$, and $P_K$ for each transition | |
| 6 | Output Transitions matrix $\mathcal{T}$ contains the step-type probabilities for each transition | |
| 7 | end function | |
| 8 | function SELFALIGN($\{x^i\}$) | |
| 9 | $\mathcal{T} \leftarrow$ STEPPROBS($\{x^i\}$) | |
| 10 | $P_{SA} \leftarrow -\dfrac{3}{2}$ | |
| 11 | Calculate Alignment $\mathcal{A}$ is the alignment of $\{x^i\}$ to $\{x^i\}$ subject to the self-alignment penalty $P_{SA}$ and the transition penalties $\mathcal{T}$ | $\mathcal{A}$ is a $1 \times N$ array, where $\mathcal{A}_i = j$ means that the $i^{th}$ measured state is the $j^{th}$ recombined state |
| 12 | Output: $\mathcal{A}$ | |
| 13 | end function | |
| 14 | Initialize: $changed \leftarrow TRUE$ $\{x^i_{new}\} \leftarrow \{x^i\}$ | |

*FIG. 28A*

| 15 | while *changed* do | |
|---|---|---|
| 16 | $\{x_{old}^i\} \leftarrow \{x_{new}^i\}$ | Store the existing $\{x_{new}^i\}$ in a new variable |
| 17 | $\mathcal{A} \leftarrow \text{SELFALIGN}(\{x_{old}^i\})$ | Conduct self-alignment |
| 18 | if $\max(\mathcal{A}) = \text{length}(\{x_{old}^i\})$ then | We have the same numer of recombined states as initial states, meaning nothing has been recombined |
| 19 | $\{x_{new}^i\} \leftarrow \{x_{old}^i\}$ | no states have changed so just pass on the old ones |
| 20 | *changed* $\leftarrow$ FALSE | Our recombination has converged, exit the while loop |
| 21 | else | |
| 22 | Initialize: $\{x_{new}^i\}$ as a empty holder of size 1 x $\max(\mathcal{A})$ | Storage for the set of recombined states |
| 23 | for $i \in 1{:}\max(\mathcal{A})$ do | Loop over old states and recombine into new states based on alignment |
| 24 | $x_{new}^i \leftarrow \text{mean}(\{x_{old}^{\{j\}}\})$ where $\{j\}$ is such that $\mathcal{A}^j = i$ for all $j \in \{j\}$ | |
| 25 | end for | |
| 26 | *changed* $\leftarrow$ TRUE | As long as things have changed, continue recombination |
| 27 | end if | |
| 28 | end while | |
| 29 | Output $\{x_{new}^i\}$ | Final output is the new set of recombined states |

FIG. 28B

| 1 | Input: | |
|---|---|---|
| | $\mathbb{P}$ | step-type log-probabilities for each of the $N-1$ transitions |
| | $\mathbb{L}$ | matrix of allowed "transition type" linkages |
| 2 | Initialize: | |
| | $\mathbb{A} \leftarrow \text{ones}(N-1, 4)$ | alignment matrix, $1^{st}$ column is $S$, $2^{nd}$ is $B$, $3^{rd}$ is $K|SK$, $4^{th}$ is $K|B$ |
| | $\mathbb{B} \leftarrow \text{ones}(N-1, 4)$ | traceback matrix |
| 3 | $\mathbb{A}_{1,1:3} \leftarrow [\mathbb{P}_{1,1}, \mathbb{P}_{1,2}, \mathbb{P}_{1,3}, -\infty]$ | Fill first row of alignment matrix |
| 4 | for $i \in 2 : (N-1)$ do | Loop over the rest of the transitions, filling the alignment and traceback matrices |
| 5 | $A \leftarrow [\mathbb{P}_{i,1}, \mathbb{P}_{i,3}, \mathbb{A}_{i,2}, \mathbb{A}_{i,2}]$ | Begin filling next row in alignment matrix |
| 6 | $T \leftarrow [\mathbb{A}_{i-1,1}, \mathbb{A}_{i-1,2}, \mathbb{A}_{i-1,3}, \mathbb{A}_{i-1,4}]$ | $T$ stores the scores of possible cells we can transition in from |
| 7 | for $j \in 1 : 4$ do | Loop over the 4 transition types |
| 8 | $t \leftarrow T$ | make a copy of $t$ as we fill this particular cell |
| 9 | $t_k \leftarrow -\infty$ for $\forall k$ where $\mathbb{L}_{k,j} = 0$ | turn off disallowed transitions |
| 10 | $t_* \leftarrow \max(t)$ | take the best scoring path in |

FIG. 29A

| 11 | $b_* \leftarrow k$ such that $t_k = t_*$ | record which transition had the best score |
|---|---|---|
| 12 | $\mathbb{A}_{i,j} \leftarrow A_j + t_*$ | fill alignment matrix cell |
| 13 | $\mathbb{B}_{i,j} \leftarrow b_*$ | fill traceback matrix cell |
| 14 | end for | |
| 15 | end for | |
| 16 | Initialize $\mathbb{R} \leftarrow []$ | initialize storage for the best path through the alignment matrix as we conduct traceback |
| 17 | $\mathbb{R} \leftarrow [r\mathbb{R}]$ where $r$ is such that $\mathbb{A}_{n-1,r} = \max(\mathbb{A}_{n-1,:}$ | start traceback at best scoring cell in bottom row of $\mathbb{A}$ |
| 18 | for do $i \in (n-1) : -1 : 2$ | conduct traceback over most likely pathway |
| 19 | $r \leftarrow \mathbb{B}_{i,r}$ | $\mathbb{B}$ tells us where we came from to get to the max cell in $\mathbb{A}$ |
| 20 | $\mathbb{R} \leftarrow [r\mathbb{R}]$ | append the location of the best score in the row to the start of the traceback |
| 21 | end for | |
| 22 | Output: $r$ contains the type of step ($1 = S$, $2 = B$, $3$ and $4 = K$) taken at each transition | |

FIG. 29B

SEQUENCE LISTING

```
<160> NUMBER OF SEQ ID NOS: 25

<210> SEQ ID NO 1
<211> LENGTH: 48
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is abasic
<220> FEATURE:
<221> NAME/KEY: misc_feature
<222> LOCATION: (15)..(15)
<223> OTHER INFORMATION: n is abasic

<400> SEQUENCE: 1
naaaaaaacc ttccnccttc ccatcatcat cagatctcac gcggtgca                48

<210> SEQ ID NO 2
```

```
<211> LENGTH: 32
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (32)..(32)
<223> OTHER INFORMATION: n is abasic

<400> SEQUENCE: 2
ccgcgtgaga tctgaaaaat ttaaacccaa an                              32

<210> SEQ ID NO 3
<211> LENGTH: 54
<212> TYPE: DNA
<213> ORGANISM: Artificial sequence
<220> FEATURE:
<223> OTHER INFORMATION: Synthetic

<400> SEQUENCE: 3
gacccgccaa gtacaagtaa gcctacgcct acggtttttt ttttttttttt tttt    54

<210> SEQ ID NO 4
<211> LENGTH: 31
<212> TYPE: DNA
<213> ORGANISM: Artificial sequence
<220> FEATURE:
<223> OTHER INFORMATION: Synthetic

<400> SEQUENCE: 4
ccgtaggcgt aggcttactt gtacttggcg g                              31

<210> SEQ ID NO 5
<211> LENGTH: 55
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is abasic

<400> SEQUENCE: 5
tactactact actactacnn ttttgagcct ctcactatcg cattctcatg caggt    55

<210> SEQ ID NO 6
<211> LENGTH: 33
<212> TYPE: DNA
<213> ORGANISM: Artificial sequence
<220> FEATURE:
<223> OTHER INFORMATION: Synthetic

<400> SEQUENCE: 6
cctgcatgag aatgcgatag tgagatcgta gcc                            33

<210> SEQ ID NO 7
<211> LENGTH: 33
<212> TYPE: DNA
<213> ORGANISM: Artificial sequence
<220> FEATURE:
<223> OTHER INFORMATION: Synthetic

<400> SEQUENCE: 7
ggacgtactc ttacgctatc actcttcgta gcc                            33
```

```
<210> SEQ ID NO 8
<211> LENGTH: 26
<212> TYPE: DNA
<213> ORGANISM: Artificial sequence
<220> FEATURE:
<223> OTHER INFORMATION: Synthetic

<400> SEQUENCE: 8
agagtgatag cgtaagagta cgtcct                                                26

<210> SEQ ID NO 9
<211> LENGTH: 159
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is abasic

<400> SEQUENCE: 9
tactactact actactacnn ttttttggcg cttcatacag ccgcgccggc gagattttgg           60
cgagacaggc acgcgcgagc ccaatctatt ttcaatctac gtatactagg gggttctagt          120 acttttctc actatcgcat tctcatgcag gtcgtagcc                                 159

<210> SEQ ID NO 10
<211> LENGTH: 158
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is abasic

<400> SEQUENCE: 10
tactactact actactacnn ttttctagta cactagacta gtccctacta cgatttttct          60
acgattaggg ccctatctaa tctagagttt ttctagagta gggaccccgg gactcccttg         120 tattttctc actatcgcat tctcatgcag tcgtagcc                                 158

<210> SEQ ID NO 11
<211> LENGTH: 159
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is abasic

<400> SEQUENCE: 11
tactactact actactacnn ttttccttgt agatcctata cggacggggt ctcttttgg           60 tctctagcgc tcgaatgtgt cgacaccttt ttgacacctc agagacctag ctaggctagt         120
gttttttctc actatcgcat tctcatgcag gtcgtagcc                                159

<210> SEQ ID NO 12
<211> LENGTH: 159
<212> TYPE: DNA
<213> ORGANISM: Artificial sequence
<220> FEATURE:
<223> OTHER INFORMATION: Synthetic
<220> FEATURE:
```

```
<221> NAME/KEY: misc_feature
<222> LOCATION: (19)..(20)
<223> OTHER INFORMATION: n is abasic

<400> SEQUENCE: 12
tactactact actactacnn ttttctagtg tacacctcgg accggtgccc tcgattttcc      60
ctcgagagga ccatgctagc cccccgcttt ttccccgcta tacaagtacc cgagttagaa     120 ctttttctc actatcgcat tctcatgcag gtcgtagcc                             159

<210> SEQ ID NO 13
<211> LENGTH: 159
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is abasic

<400> SEQUENCE: 13
tactactact actactacnn ttttagaac taggatagg tggggcacat accttttca        60 tacctaggtc cgaatcgatc ttagcctatt tttagcctaa gggtagacgt gattgggcct    120 acttttctc actatcgcat tctcatgcag gtcgtagcc                            159

<210> SEQ ID NO 14
<211> LENGTH: 121
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is abasic

<400> SEQUENCE: 14
tactactact actactacnn ttttcatacg tagcatttt cataggcccc attttcatc        60 ccgcgcattt ttcatcctac gcatttttc tcactatcgc attctcatgc aggtcgtagc     120
c                                                                    121

<210> SEQ ID NO 15
<211> LENGTH: 25
<212> TYPE: DNA
<213> ORGANISM: Artificial sequence
<220> FEATURE:
<223> OTHER INFORMATION: Synthetic

<400> SEQUENCE: 15
cctgcatgag aatgcgatag tgaga                                           25

<210> SEQ ID NO 16
<211> LENGTH: 70
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (31)..(32)
<223> OTHER INFORMATION: n is abasic

<400> SEQUENCE: 16
tactactact actactacta ctactactac nnttttattg aagtgcagta ctttactaat      60
```

```
tattgctttt                                                           70

<210> SEQ ID NO 17
<211> LENGTH: 38
<212> TYPE: DNA
<213> ORGANISM: Artificial sequence
<220> FEATURE:
<223> OTHER INFORMATION: Synthetic

<400> SEQUENCE: 17
gatcaaaagc aataattagt aaagtactgc acttcaat                            38

<210> SEQ ID NO 18
<211> LENGTH: 46
<212> TYPE: DNA
<213> ORGANISM: Artificial sequence
<220> FEATURE:
<223> OTHER INFORMATION: Synthetic

<400> SEQUENCE: 18
gatcattgaa gtgcagtact ttactaatta ttgcttttc tgagcc                    46

<210> SEQ ID NO 19
<211> LENGTH: 34
<212> TYPE: DNA
<213> ORGANISM: Artificial sequence
<220> FEATURE:
<223> OTHER INFORMATION: Synthetic

<400> SEQUENCE: 19
aaaagcaata attagtaaag tactgcactt caat                                34

<210> SEQ ID NO 20
<211> LENGTH: 74
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (31)..(32)
<223> OTHER INFORMATION: n is abasic

<400> SEQUENCE: 20
tactactact actactacta ctactactac nntttattg aagtgcagta ctttactaat     60
tattgctttt catg                                                      74

<210> SEQ ID NO 21
<211> LENGTH: 34
<212> TYPE: DNA
<213> ORGANISM: Artificial sequence
<220> FEATURE:
<223> OTHER INFORMATION: Synthetic

<400> SEQUENCE: 21
aaaagcaata attagtaaag tactgcactt caat                                34

<210> SEQ ID NO 22
<211> LENGTH: 38
<212> TYPE: DNA
<213> ORGANISM: Artificial sequence
<220> FEATURE:
<223> OTHER INFORMATION: Synthetic

<400> SEQUENCE: 22
```

```
aagtgcagta ctttactaat tattgctttt tctgagcc                        38
```

<210> SEQ ID NO 23
<211> LENGTH: 38
<212> TYPE: DNA
<213> ORGANISM: Artificial sequence
<220> FEATURE:
<223> OTHER INFORMATION: Synthetic

<400> SEQUENCE: 23

```
aaaagcaata attagtaaag tactgcactt caatcatg                        38
```

<210> SEQ ID NO 24
<211> LENGTH: 155
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is abasic

<400> SEQUENCE: 24

```
tactactact actactacnn tttttctgc agtgcagttt gctttgcgaa atgaaactgc   60
agtttgcgaa attgcagttt gcgaaagttt gctgcacgaa attttgctgc aggaaatttt  120
tttctcacta tcgcattctc atgcaggtcc gagcc                            155
```

<210> SEQ ID NO 25
<211> LENGTH: 25
<212> TYPE: DNA
<213> ORGANISM: Artificial sequence
<220> FEATURE:
<223> OTHER INFORMATION: Synthetic

<400> SEQUENCE: 25

```
cctgcatgag aatgcgatag tgaga                                       25
```

SYSTEMS AND METHODS FOR IMPROVED NANOPORE-BASED ANALYSIS OF NUCLEIC ACIDS

CROSS-REFERENCE(S) TO RELATED APPLICATION(S)

This application claims the benefit of Provisional Application No. 62/805,870, filed Feb. 14, 2019, the entire disclosure of which is hereby incorporated by reference herein for all purposes.

STATEMENT OF GOVERNMENT LICENSE RIGHTS

This invention was made with Government support under Grant No. R01 HG005115, awarded by the National Institutes of Health. The Government has certain rights in the invention.

STATEMENT REGARDING SEQUENCE LISTING

The Sequence Listing text file associated with this application is provided in TXT format and is hereby incorporated by reference into the specification. The name of the TXT file containing the sequence listing is 3915-P919US.PNP.UW_Seq_List_20250304_ST25.txt. The TXT file is 7,122 bytes; was created on Mar. 4, 2025; and is being submitted electronically via Patent Center with the filing of the specification.

BACKGROUND

Nanopore sequencing is an emerging third-generation single-molecule DNA sequencing technology capable of long contiguous read lengths and direct detection of non-canonical bases and epigenetically relevant modified bases at low cost and with minimal requirements for sample preparation and instrumentation. Enzyme-actuated nanopore strand sequencing devices are now commercially available, demonstrating nanopore sequencing's potential as a stand-alone DNA sequencing platform. Nanopore sequencing has been successfully employed in various DNA sequencing applications including species and pathogen identification, epigenetic mapping, outbreak tracking, and metagenomic sequencing.

Various aspects of nanopores, nanopore systems and uses of variable voltage for nanopore-based analyses are described in more detail in WO 2015/051378, incorporated herein by reference in its entirety.
potential as a stand-alone DNA sequencing platform. Nanopore sequencing has been successfully employed in various DNA sequencing applications including species and pathogen identification, epigenetic mapping, outbreak tracking, and metagenomic sequencing.

Various aspects of nanopores, nanopore systems and uses of variable voltage for nanopore-based analyses are described in more detail in WO 2015/051378, incorporated herein by reference in its entirety.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a method for analyzing a polymer analyte is provided. The method comprises translocating the polymer analyte through a nanopore from a first conductive liquid medium to a second conductive liquid medium, wherein the nanopore comprises a constriction zone, wherein the nanopore provides liquid communication between the first conductive liquid medium and the second conductive liquid medium and wherein translocating the polymer analyte through the nanopore from the first conductive liquid medium to the second conductive liquid medium comprises using a molecule configured to regulate a rate of translocation for the polymer analyte in one or more discrete steps per monomer subunit. The method also comprises applying a non-constant electrical potential between the first conductive liquid medium and the second conductive liquid medium as the polymer analyte translocates through the nanopore. The method also comprises measuring a plurality of current signals between the first conductive liquid medium and the second conductive liquid medium as the polymer analyte translocates through the nanopore. The method also comprises adjusting the measured plurality of current signals to provide an adjusted current pattern. The method also comprises determining a characteristic of the polymer analyte based on the adjusted current pattern.

In some embodiments, the characteristic of the polymer analyte is the identity of one or more monomer subunit residues of the polymer analyte. In some embodiments, the polymer analyte is a nucleic acid, and the monomer subunit is a nucleotide. In some embodiments, the polymer analyte is a peptide, and the monomer subunit is an amino acid.

In some embodiments, determining the characteristic of the polymer analyte based on the adjusted current pattern comprises conducting a principal component analysis. In some embodiments, the principal component analysis comprises use of coefficients of a plurality of top principal components of current observed at each step of the molecule configured to regulate the rate of translocation for the polymer analyte.

In some embodiments, adjusting the measured signals comprises correcting the plurality of current signals for capacitance imposed by a membrane, polymer analyte, or nanopore. In some embodiments, adjusting the measured signals comprises partitioning the plurality of current signals into separate states that correlate with the one or more discrete steps of the molecule configured to regulate the rate of translocation for the polymer analyte. In some embodiments, partitioning the current signals comprises modeling the non-constant electrical potential with a weighted sum of a plurality of time-varying basis functions. In some embodiments, partitioning the current signals comprises conducting a dimensionality reduction of the current signals associated with the separate states. In some embodiments, conducting the dimensionality reduction includes conducting a principal component analysis.

In some embodiments, adjusting the measured signals comprises normalizing the plurality of measured current signals, or the subset thereof, to remove any current signal not associated with a monomer subunit identity of the polymer analyte translocating through the nanopore. In some embodiments, the current not associated with the passage of ions through the nanopore is current associated with the capacitance of at least one of a membrane, the pore, the analyte, and internal capacitances of measurement circuitry used to collect the current signals.

In some embodiments, adjusting the measured plurality of current signals comprises deriving a current-potential curve from the current signals. In some embodiments, the method further comprises converting the current-potential curve into a conductance-voltage relationship. In some embodiments, the method further comprises converting the current-potential curve into a current-polymer analyte distance curve to provide a current pattern corresponding to a segment of the polymer analyte residing in the constriction zone of the nanopore associated with the single translocation step. In some embodiments, the converting step comprises modeling the polymer analyte as a spring with a linear restoring force, an extensible Freely Jointed Chain, or a Worm Like Chain. In some embodiments, the current-polymer analyte distance curve of the subset is indicative of the identity of one or more monomer subunit residues in the segment.

In some embodiments, at least some of the steps of adjusting measured signals may be repeated for one or more additional subsets associated with one or more additional sequential single translocation steps to provide an aggregation of multiple current patterns representing the current through the nanopore as the polymer analyte translocates continuously through the nanopore. In some embodiments, the aggregation of multiple current patterns is indicative of the identity of one or more monomer subunit residues in multiple overlapping segments of the polymer analyte. In some embodiments, the method further comprises comparing one or more of the multiple current patterns to current patterns from reference nucleic acids with known correlations between current patterns and sequence. In some embodiments, the method further comprises determining the sequence of a portion of the polymer analyte corresponding to the overlapping segments.

In some embodiments, the method further comprises detecting one or more discontinuities in the aggregation of multiple current patterns. In some embodiments, the method further comprises identifying the one or more discontinuities as a forward skip or backstep associated with an aberrant translocation movement of the polymer analyte. In some embodiments, the method further comprises correcting the discontinuity.

In some embodiments, adjusting the measured plurality of current signals comprises applying a filter to remove observed states from the current pattern that do not correlate with a polymer analyte in the nanopore. In some embodiments, the filter removes aberrant states of 1 ms or less of reduced current associated with the molecule configured to regulate the rate of translocation for the polymer analyte. In some embodiments, the filter removes long states based on a calculated probability of aberration. In some embodiments, the filter removes states corresponding to mis-steps, including skips or backsteps, of the molecule configured to regulate the rate of translocation for the polymer analyte. In some embodiments, the filter comprises self-alignment of the current to itself to detect repeated states. In some embodiments, the filter comprises application of one or more machine learning methods to provide a probability of an aberration state in the current signals. In some embodiments, the machine learning method includes application of one or more support vector machines (SVMs) coupled to logit functions.

In some embodiments, the molecule configured to regulate the rate of translocation for the polymer analyte is a molecular motor. In some embodiments, the molecule configured to regulate the rate of translocation for the polymer analyte is a translocase, a polymerase, a helicase, an exonuclease, or a topoisomerase. In some embodiments, the polymerase is phi29 DNA polymerase, Klenow fragment, or a variant or homolog thereof. In some embodiments, the helicase is a Hel308 helicase, a RecD helicase, a TraI helicase, a TraI subgroup helicase, an XPD helicases or a variant or homolog thereof. In some embodiments, the exonuclease is exonuclease I, exonuclease III, lambda exonuclease, or a variant or homolog thereof. In some embodiments, the topoisomerase is a gyrase or a variant or homolog thereof.

In some embodiments, the non-constant electrical potential has a periodic function or a non-periodic function. In some embodiments, the non-constant electrical potential is superimposed onto a constant potential that is between 10 mV and 1 V. In some embodiments, the non-constant electrical potential is superimposed onto a constant potential that is between 10 mV and 300 mV. In some embodiments, the periodic function of the non-constant electrical potential has minimum to maximum difference of less than 300 mV. In some embodiments, the periodic function of the non-constant electrical potential has a period of between 0.01 ms and 1 s. In some embodiments, the periodic function is triangular, sawtooth, square, sinusoidal, a custom function, or linear combinations thereof. In some embodiments, the periodic function is optimized to promote a substantially constant rate of polymer analyte movement within the nanopore during a period of increasing or decreasing potential in the periodic function.

In some embodiments, the nanopore is a solid-state nanopore, protein nanopore, a hybrid solid state-protein nanopore, a biologically adapted solid-state nanopore, or a DNA origami nanopore. In some embodiments, the protein nanopore is alpha-hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP), WZA, lysenin or a homolog or variant thereof. In some embodiments, the protein nanopore sequence is modified to contain at least one amino acid substitution, deletion, or addition. In some embodiments, the at least one amino acid substitution, deletion, or addition results in a net charge change in the nanopore. In some embodiments, the protein nanopore has a constriction zone with a non-negative charge.

In another aspect, a nanopore system is provided. The system comprises a nanopore, a molecule, a voltage source, a detection device, and a processor. The nanopore comprises a constriction zone and a vestibule that together define a tunnel. The nanopore provides liquid communication between a first conductive liquid medium and a second conductive liquid medium through the tunnel. The molecule is configured to regulate a rate of translocation of a polymer analyte molecule through the tunnel of the nanopore in one or more discrete steps per monomer subunit. The voltage source is configured to apply a non-constant electrical potential between the first conductive liquid medium and the second conductive liquid medium. The detection device is configured to measure current signals between the first conductive liquid medium and the second conductive liquid medium as a polymer analyte translocates through the nanopore. The processor is communicatively coupled to the detection device and comprises logic that, when executed, adjusts the measured current signals. The system is operative to translocate a polymer analyte from the first conductive liquid medium to the second conductive liquid medium.

In some embodiments, the polymer analyte is a nucleic acid, and wherein the monomer subunit is a nucleotide. In some embodiments, the polymer analyte is a peptide, and wherein the monomer subunit is an amino acid.

In some embodiments, the adjustment of the measured current signals implemented by the logic comprises correcting the plurality of current signals for capacitance imposed by a membrane, polymer analyte, or nanopore.

In some embodiments, the adjustment of the measured current signals implemented by the logic comprises partitioning the plurality of current signals into separate states that correlate with the one or more discrete steps of the molecule configured to regulate the rate of translocation.

In some embodiments, the adjustment of the measured current signals implemented by the logic comprises normalizing the plurality of measured current signals, or the subset thereof, to remove any current signal not associated with passage of ions through the nanopore.

In some embodiments, the adjustment of the measured current signals implemented by the logic comprises normalizing the plurality of measured current signals, or the subset thereof, to remove variations in the current signals caused by mechanical differences in the polymer analyte molecule based on an amplitude of applied electrical potential.

In some embodiments, the adjustment of the measured current signals implemented by the logic comprises performing a principal component analysis on the measured current signals.

In some embodiments, the adjustment of the measured current signals implemented by the logic comprises applying a filter to remove observed states from the current pattern that do not correlate with a polymer analyte in the nanopore.

In some embodiments, the system further comprises a membrane, wherein the membrane is a lipid bilayer. In some embodiments, the system further comprises a membrane, wherein the membrane comprises a block copolymer.

In some embodiments, the nanopore is a solid-state nanopore, protein nanopore, a hybrid solid state-protein nanopore, a biologically adapted solid-state nanopore, a graphene nanopore, or a DNA origami nanopore. In some embodiments, the protein nanopore is an alpha-hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP), WZA, lysenin or a homolog or variant thereof. In some embodiments, the protein nanopore sequence is modified to contain at least one amino acid substitution, deletion, or addition. In some embodiments, the at least one amino acid substitution, deletion, or addition results in a net charge change in the nanopore. In some embodiments, the protein nanopore has a constriction zone with a non-negative charge.

In some embodiments, the first conductive liquid medium and the second conductive liquid medium comprise KCl at a concentration in a range of about 100 mM to about 1000 mM, and HEPES at a concentration in a range of about 9 mM to about 11 mM at a pH in a range of about 7.00±0.05 to about 9.00±0.05. In some embodiments, the first conductive liquid medium comprises ATP at a concentration in a range of about 10 µM to about 1000 µM. In some embodiments, the first conductive liquid medium comprises EDTA at a concentration in a range of about 0.9 mM to about 1.1 mM, DTT at a concentration in a range of about 0.9 mM to about 1.1 mM, and MgCl2 at a concentration in a range of about 9 mM to 11 mM.

In another aspect, a computer-implemented method of determining an identity of one or more monomer subunit residues of a polymer analyte is provided. A raw current signal generated by using a variable voltage to translocate the polymer analyte through a nanopore is received. Change points are detected in the raw current signal to determine a series of states. Capacitance compensation is performed on the raw current signal for each state to create an ionic current-vs-voltage curve for each state. The ionic current-vs-voltage curves are converted to conductance-vs-voltage curves. Filtering is performed for the series of states to create a series of filtered states. The identity of one or more monomer subunit residues of the polymer analyte is determined based on the series of filtered states.

In some embodiments, the polymer analyte is a nucleic acid, and the monomer subunit is a nucleotide. In some embodiments, the polymer analyte is a peptide, and the monomer subunit is an amino acid.

In some embodiments, detecting change points in the raw current signal includes removing flicker from the raw current signal to create a flicker-free current signal, and using the flicker-free current signal to detect the change points.

In some embodiments, detecting change points in the raw current signal includes determining basis functions derived from a dimensionality-reduced version of the raw current signal. In some embodiments, the dimensionality-reduced version of the raw current signal is generated via principal component analysis.

In some embodiments, detecting change points in the raw current signal includes using an over-fitting bias removal technique to remove over-fitting bias from a likelihood-maximization process for determining the change points. In some embodiments, the over-fitting bias removal technique is at least one of a Change Point Information Criterion or an Aikaike Information Criterion.

In some embodiments, performing capacitance compensation on the raw current signal for each state to create an ionic current-vs-voltage curve for each state includes determining a phase of the raw current signal based on an applied voltage signal; binning data points in the raw current signal based on a location of each data point in the phase of the raw current signal; averaging data points in each bin to determine an average current-voltage characteristic for up portions of the phase and for down portions of the phase; determining a difference between the average current-voltage characteristic for up portions of the phase and the average current-voltage characteristic for down portions of the phase to find an asymmetry between the up portions and the down portions; fitting a parabola to the asymmetry between the up portions and the down portions over a second quartile and a third quartile of the voltage to determine a residual function; determining an up correction function and a down correction function based on the residual function; applying the up correction function to the average current-voltage characteristic for up portions of the phase and applying the down correction function to the average current-voltage characteristic for down portions of the phase; and applying a correction based on the average current-voltage characteristics to each data point of the raw current signal to create the ionic current-vs-voltage curves.

In some embodiments, one or more features are determined for each state based on the conductance-vs-voltage curves. In some embodiments, the conductance-vs-voltage curves include a full feature vector, and determining the one or more features for each state includes, for each state, performing dimensionality reduction on the full feature vector. In some embodiments, performing dimensionality reduction includes performing a principal component analysis to determine a reduced set of descriptive features of the full feature vector.

In some embodiments, converting the ionic current-vs-voltage curves to the conductance-vs-voltage curves includes performing conductance normalization to remove any portion of the current signal not associated with a monomer subunit identity of the polymer analyte translocating through the nanopore. In some embodiments, performing conductance normalization includes determining a mean conductance at each voltage over each state; and, for each state: subtracting the mean conductance from the measured conductance of the state to obtain a reduced conductance curve; fitting a linear model to the reduced conductance curve to obtain a slope; linearly fitting the slope to a mean voltage of the reduced conductance curves to obtain a bias; and subtracting the bias from the reduced conductance curve to remove the portion of the conductance that is not dependent upon monomer subunit position.

In some embodiments, performing filtering for the series of states to create a series of filtered states includes applying a removal filter to remove states that are not informative of the monomer subunit residues; applying a recombination filter to remove states that represent repeated measurements of the same monomer subunit position; and applying a reordering filter to identify and correct out-of-order states.

In some embodiments, applying the removal filter includes determining a probability that a state should be removed using a machine learning classification algorithm. In some embodiments, the machine learning classification algorithm is a support vector machine. In some embodiments, determining the probability that the state should be removed using the machine learning classification algorithm includes determining the probability based on one or more features of the state, one or more features of a preceding state, and one or more features of a subsequent state. In some embodiments, determining the probability that the state should be removed using the machine learning classification algorithm includes determining the probability based further on at least one of: a value of a single conductance measurement in the state that most deviates from an overall mean conductance; an average mean square difference between a full feature vector of the state and a reduced-dimensionality feature vector of the state; and a score of a best match for the state against a k-mer model.

In some embodiments, applying the recombination filter to remove states that represent repeated measurements of the same monomer subunit position includes performing a Needleman-Wunsch-style alignment of each state against itself. In some embodiments, performing the Needleman-Wunsch-style alignment of each state against itself includes determining step-type probabilities at each transition based on conductance curve overlap information using a machine learning classification algorithm; and applying a self-alignment penalty to newly created states.

In some embodiments, the machine learning classification algorithm is an ensemble of support vector machines.

In some embodiments, applying the reordering filter to identify and correct out-of-order states includes: using a machine learning classification technique to assign a probability that each transition was a step, a skip, or a backstep; and using a dynamic programming technique to reorder the states in a most likely true order. In some embodiments, the machine learning classification algorithm is an ensemble of support vector machines with associated logit functions.

In some embodiments, determining the identity of one or more monomer subunit residues of the polymer analyte based on the series of filtered states includes performing sequencing using a hidden Markov model (HMM) solver. In some embodiments, performing sequencing using the HMM solver includes using information regarding a likelihood of a sequencing enzyme used to translocate the polymer analyte through the nanopore in a given state to help determine state probabilities for a score matrix used with the HMM solver. In some embodiments, performing sequencing using the HMM solver includes using probabilities of steps, skips, and bad levels determined while performing filtering on the series of states to help determine state probabilities for a score matrix used with the HMM solver.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 20 includes two charts that illustrate a non-limiting example embodiment of converting SVM outputs to $P_{bad}$ probabilities;

FIG. 22 is a chart that illustrates a non-limiting example embodiment of a full matrix of transition penalties (penalties taken as log probabilities, $S=\log(P_S)$, etc.) according to various aspects of the present disclosure;

FIG. 26 is a pseudo-code listing that describes a non-limiting example embodiment of a change point detection technique according to various aspects of the present disclosure;

FIG. 27 is a pseudo-code listing that describes a non-limiting example embodiment of a removal filter according to various aspects of the present disclosure;

FIG. 28 is a pseudo-code listing that describes a non-limiting example embodiment of a recombination filter according to various aspects of the present disclosure;

FIG. 29 is a pseudo-code listing that describes a non-limiting example embodiment of a reordering filter that uses a dynamic programming technique according to various aspects of the present disclosure.

DETAILED DESCRIPTION

Figure 1:
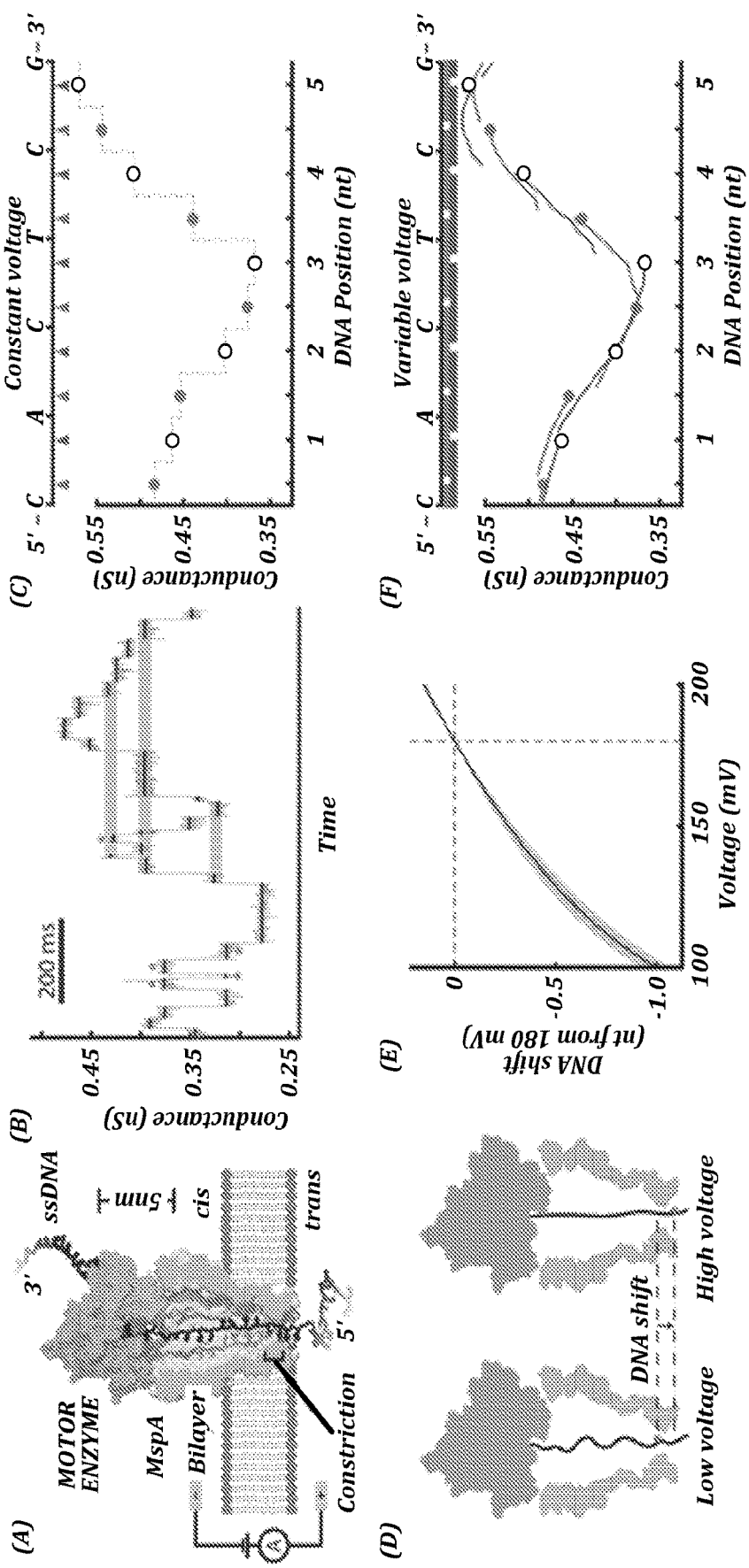
FIG. 1 includes multiple drawings and charts that illustrate various features of a non-limiting example embodiment of nanopore sequencing according to various aspects of the present disclosure.

FIG. 1 includes multiple drawings and charts that illustrate various features of a non-limiting example embodiment of nanopore sequencing according to various aspects of the present disclosure. Portion (a) of FIG. 1 illustrates that, in enzyme-actuated nanopore strand sequencing, a single nanometer-scale protein pore ("nanopore") is inserted into a membrane separating two wells, each filled with a buffered, conductive electrolyte solution. A lone MspA nanopore inserts into a lipid bilayer separating two chambers, cis and trans. A Hel308 helicase motor enzyme controls the motion of ssDNA through the pore while we apply a voltage across the bilayer and measure the conductance through the pore. The nanopore provides the lone conductive pathway between the two wells. When a voltage is applied across the membrane, an ionic current flows through the pore. DNA molecules, which are poly-negatively charged, are drawn into, and then through the pore by the voltage. As the DNA passes through the pore, it partially blocks the ionic current flow, reducing the conductance of the pore to a value dependent on the specific nucleotides present within the narrowest constriction of the pore. A DNA-translocating motor protein such as a DNA polymerase or helicase binds to the DNA, comes to rest on the pore, and restricts the DNA's translocation to discrete steps. The discrete enzyme steps incrementally pause translocation long enough to resolve the sequence-dependent modulations in the conductance signal. A change-point detection algorithm detects enzyme steps in the raw conductance signal, then a base calling algorithm decodes the segmented conductance signal into the DNA sequence.

Nanopore sequencing is limited by a low single-passage de novo sequencing accuracy relative to other established sequencing platforms. High accuracy de novo nanopore sequencing can be achieved by combining multiple high-error nanopore reads into low-error consensus sequences. However, this approach exchanges throughput for accuracy, and is still fundamentally limited by systematic errors. Additionally, some nanopore applications, such as pathogen detection at low concentrations and metagenomics studies, are most effective if they are able to identify a single molecule of DNA with only one read. Therefore, the path toward fully realized nanopore sequencers requires improvement of the baseline single-passage accuracy.

Many of the single-passage sequencing errors can be attributed to two primary error modes: distinct sequences with indistinguishable conductance signals and irregular steps by the motor enzyme. To decode an observed signal, the base calling algorithm must use a model of the blockaded pore conductance that maps observed conductance values to the likely generating DNA sequence. The conductance through the nanopore is influenced by several nucleotides near the constriction of the pore, resulting in a complex map of conductance to the underlying sequence. In many instances, different sequence segments generate statistically indistinguishable conductance values, thereby leading to error-prone base calls. Portion (b) of FIG. 1 illustrates these primary error modes. A segment of constant-voltage nanopore data (downsampled to 500 Hz) shows several common sequencing error modes. The overlaid black lines show the mean conductance at each enzyme step. Stars mark the locations of enzyme missteps. Bars highlight indistinguishable conductance states generated by distinct DNA sequences.

Irregular stepping by the DNA-controlling motor enzyme can also introduce sequencing errors. Ideally, the enzyme would move DNA unidirectionally through the pore in discrete steps of uniform length. However, the stochastic stepping of enzymes frequently diverges from this ideal behavior. In addition to regular forward steps, "skips" can occur when multiple forward steps occur in quick succession, too fast to electronically resolve the intermediate step or steps. Additionally, "backsteps" can occur when the enzyme backtracks to a previously observed position along the DNA (the stars in portion (b)). The existence of irregular enzyme steps means that the observed time order of conductance states does not necessarily match the base order in the DNA, and no part of the nanopore signal clearly distinguishes these steps from regular processive behavior. This complicates finding the true sequence from the observed conductance states and causes sequencing errors.

Accordingly, despite the advances in nanopore-based sequencing technologies, a need remains for enhancing the sensitivity and resolution of nanopore-based polymer analysis. The methods and systems of the present disclosure address this and related needs of the art.

Nanopore sequencing of polymer analytes is limited by intrinsically low base calling accuracy. Previous attempts at improving the accuracy have been focused on base calling algorithms, better nanopores and motor enzymes, and biochemical methods to re-read the molecule. Presented here is a new operational approach to improving nanopore sequencing accuracy. Specifically, the present disclosure demonstrates that using a time-varying waveform driving voltage generates a more information-rich electronic signal by fundamentally changing the method of controlling motion of a polymer analyte, such as a nucleic acid, through the nanopore.

The discussion herein primarily focuses on the processing of DNA as the polymer analyte for the sake of clarity. However, one will recognize that the technology disclosed herein is not limited to the processing of DNA. Instead, the technology disclosed herein may be used to process any polymer analyte made up of monomer subunits, including but not limited to proteins made up of amino acids, such as peptides.

In embodiments where an enzyme is used to move the DNA through the nanopore in discrete steps, the variable voltage positions the DNA continuously between these steps. The resulting signal permits identification and recovery from the primary error modes in base calling: enzyme missteps and multiple sequences with indistinguishable signals. Using new data analytics and correction approaches as described below, the inventors found that single-passage de novo accuracy in the system increased from 62.7±0.5% with a constant driving voltage to 79.3±0.3% with a variable driving voltage. This operational method is complementary to other advances in nanopore sequencing and is amenable to incorporation into other enzyme-actuated nanopore sequencing devices.

Portions (c)-(f) of FIG. 1 show additional characteristics of nanopore sequencing. Portion (c) illustrates that, in constant-voltage sequencing, we sample the conductance of the DNA-blockaded pore at discrete locations (arrows) along the DNA sequence (top). The resulting signal is a time-ordered series of mean conductance values, one for each enzyme step (circular points; gray line to guide the eye). The points mark odd-numbered half-nucleotide steps by the Hel308 helicase and the circles mark even-numbered steps. Portion (d) illustrates that applying different voltages changes the pulling force on the DNA. Higher forces cause the DNA to extend further, shifting the DNA within the constriction of the pore and changing the DNA bases affecting the conductance. This cartoon shows a DNA base (dot) changing position when the applied voltage is increased. In some embodiments, the present disclosure may model the nucleic acid as a Hookian spring with a linear restoring force, an extensible Freely Jointed Chain, or a Worm Like Chain when determining how far the DNA may shift within the constriction of the pore and/or how many DNA bases affect the conductance for a given voltage. Portion (e) illustrates that the range of applied voltages in our variable-voltage experiments (100 mV to 200 mV) shifts the DNA position in the pore by more than a full nucleotide. The position shift is relative to the DNA position at 180 mV.

Portion (f) illustrates aspects of variable-voltage sequencing, versus the constant voltage sequencing illustrated in portion (c). Variable-voltage sequencing samples the conductance of the DNA-blockaded pore continuously along the DNA sequence (top). Bars at the top show the overlapping ranges along the DNA molecule probed during the voltage swing at odd and even enzyme steps. In the resulting signal, each enzyme step is characterized by a conductance vs. DNA position curve (curves), rather than by a single mean conductance as in constant-voltage sequencing (points).

Figure 2:
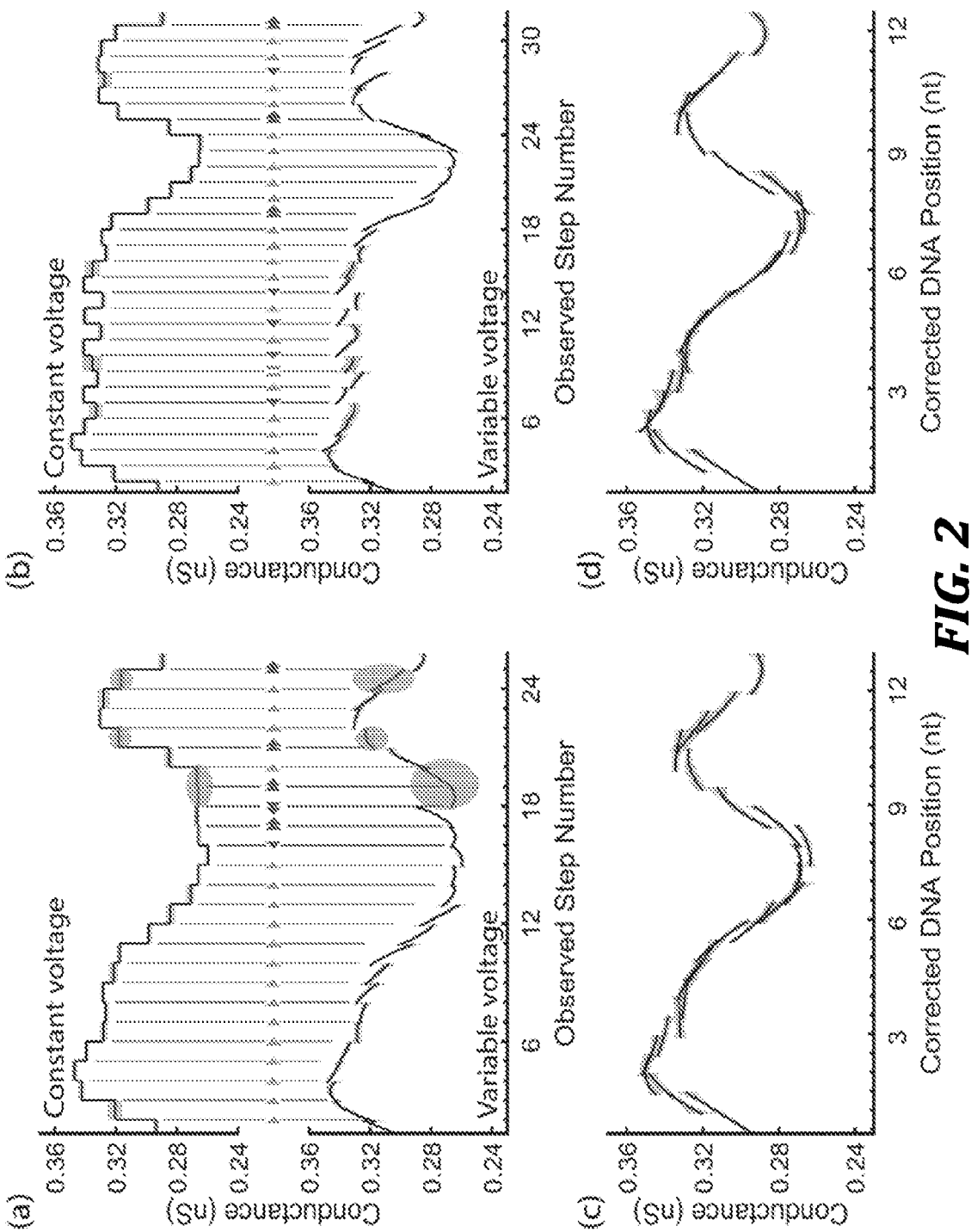
FIG. 2 includes several charts that illustrate some non-limiting examples of differences between constant-voltage reads and variable-voltage reads according to various aspects of the present disclosure.

FIG. 2 includes several charts that illustrate some non-limiting examples of differences between constant-voltage reads and variable-voltage reads according to various aspects of the present disclosure. Portions (a) and (b) of FIG. 2 compare the measured conductance vs. position curve segments of two typical variable-voltage reads (bottom) of the same DNA sequence to a reproduction of the corresponding constant-voltage reads (top), created by extracting the conductance of these segments at 180 mV only. Nearly identical conductances at 180 mV are easily distinguishable when the full conductance vs. position curves are compared (states highlighted with ovals). Enzyme stepping errors are inferred from discontinuities in the curve and identification of repeated curve segments. These are marked with right arrows (forward steps), double right arrows (skips) and left arrows (backsteps). Portions (c) and (d) show these reads after correction of the identified enzyme stepping errors. Although the uncorrected reads look dissimilar, the corrected reads are almost identical and will be decoded into the same DNA sequence.

Figure 3B:
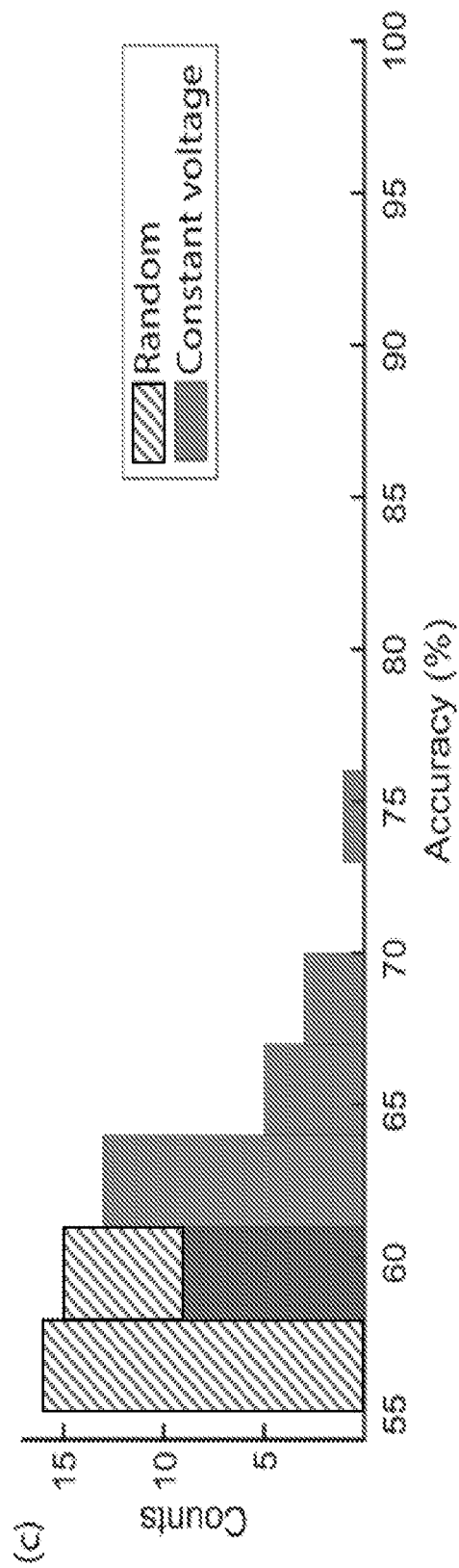
FIG. 3 includes several charts that illustrate some non-limiting examples of differences in performance between constant-voltage reads and variable-voltage reads according to various aspects of the present disclosure.
Figure 3C:
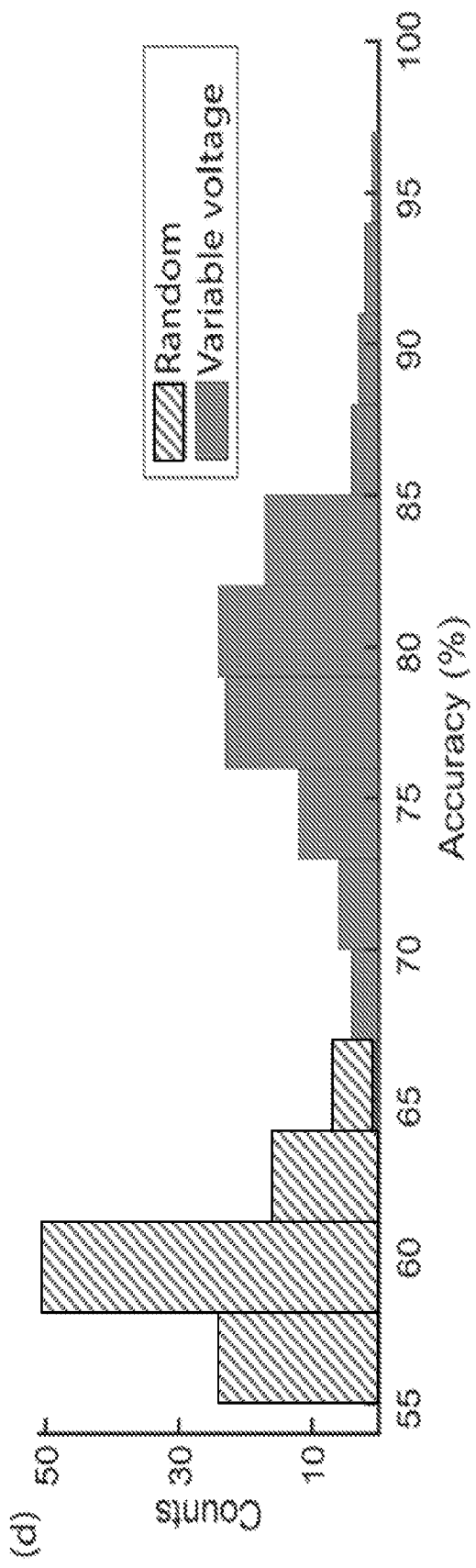

FIG. 3 includes several charts that illustrate some non-limiting examples of differences in performance between constant-voltage reads and variable-voltage reads according to various aspects of the present disclosure. Confusion matrices for sequencing using constant-voltage (portion (a)) and variable-voltage (portion (b)) show a reduction in mismatch, insertion and deletion errors across all bases with the use of variable-voltage. Histograms of single-passage accuracies for 31 constant-voltage reads (9368 total bases) (portion (c)) and 97 variable-voltage reads (17309 total bases) (portion (d)) show a significant improvement in the distribution of read accuracies using variable-voltage. Single-passage sequencing accuracies are plotted in solid bars, with the distribution of accuracies for randomly generated sequences of the same lengths plotted in dashed bars. While constant-voltage nanopore sequencing is only a few percent above random base calling, the variable-voltage method yields a substantial improvement.

The following descriptions are non-limiting examples of advances and embodiments provided by the present disclosure. These statements are intended to illustrate and not limit aspects of the disclosure.

Techniques for Handling Capacitive Currents ("Capacitance Compensation")

The lipid bilayer in the nanopore system acts as a capacitor. When a variable voltage is applied, this capacitance causes a capacitive current that obscures the DNA-dependent signal we wish to observe.

Previously, this signal was treated using the capacitance compensation features of the Axopatch amplifier. This approach relied on the operator to carefully adjust the compensation settings and was not robust to operator error or changing conditions over the course of a read. Additionally, it did not adequately correct for the changing resistance of the system as different DNA bases enter the pore.

The disclosure provides a new capacitance compensation technique that can be performed after data collection using a new software-implemented approach. This technique removes the possibility of operator error and can handle drift in experimental conditions over time, making the data more reliable. The technique also corrects the capacitance separately at each enzyme step, better accounting for the changing resistance at different DNA positions and yielding a better correction.

Techniques for Detecting Enzyme Step Locations in the Variable-Voltage Current Signal "Change Point Detection")

The nanopore current signal is partitioned into separate states at each enzyme step prior to sequencing. Enzyme steps are detected in the signal using a change point detection technique.

Previously, change point detection techniques worked only for constant-voltage signals. Prior techniques located enzyme steps in the data by detecting locations where the mean and standard deviation of the current signal changed. This technique could only be used for variable-voltage data if the data was first downsampled to average over each complete voltage cycle. This approach was suboptimal, as it was unable to detect the exact time point of the enzyme steps, had difficulty detecting enzyme steps lasting only a few voltage cycles, and did not fully make use of the additional information present in the variable-voltage signal.

The disclosure provides a new change point detection technique that been adapted to handle un-downsampled variable-voltage data. This point detection technique now models the variable-voltage signal using a weighted sum of several time-varying basis functions known to describe the data. These basis functions were derived from principal component analysis of known enzyme steps in un-capacitance-compensated variable voltage data. A set of the top (e.g., top five) principal components are used as the basis functions. This technique is better able to detect short enzyme states, can find the exact time point of enzyme steps, and can find states not easily distinguishable purely by their mean current by using the additional information in the variable-voltage signal. Furthermore, this technique works well even before capacitance compensation is performed. This allows us to operate the capacitance compensation separately at each enzyme step, best accounting for the changing resistance at the different DNA positions.

Techniques for Normalizing Current Measurements Collected at Different Voltages

The non-ohmic character of the nanopore's conductance when blockaded by a charged molecule introduces a non-DNA sequence-dependent component to the variable-voltage signal. This contribution must be removed in order to recover the purely DNA-position-dependent signal desired for variable-voltage sequencing. This process of accounting for and removing the non-DNA-dependent component of the signal is referred to as "normalization."

Prior normalization procedures relied on an empirical "correction function" based on measurement of the current-vs-voltage response of homopolymer DNA held anchored in the pore. This technique was not robust to changes in experimental conditions, including salt concentration in the buffer, temperature, pore orientation, and the like.

The disclosure provides a new normalization correction that calculates normalization directly from the measured data in a DNA read. This technique is far more robust to changes in experimental conditions. Additionally, we have incorporated an additional correction for the fact that more bases simultaneously influence the observed current at low voltages than at high voltages. This pore sensitivity correction improves the continuity of the recovered signal.

Features to Describe Individual Enzyme States in Variable Voltage Data

To extract the DNA sequence from variable-voltage data, we describe the data at each enzyme step using a "feature vector." The values in the entries in the feature vector describe the characteristic of that observed state. The covariances between the features describe the uncertainty in the measurement of the observed state.

Previously, the average current during the state was used at 101 separate voltages to define a 101-dimensional feature vector. Many of these features are not independent and so provide redundant information and serve only to introduce noise into the characterization of the state. Furthermore, the high dimensionality of these feature vectors made it difficult to accurately estimate their covariance.

The disclosure provides a new principal component analysis to reduce the dimensionality of these feature vectors. By replacing the 101 current measurements with the coefficients of a set of the top (e.g., top 3) principal components, nuisance parameters are removed from our feature vectors. The covariance of these 3-dimensional principal component feature vectors can be well estimated from far fewer measurements of the state.

Use of Variable-Voltage Information for State Filtering

Variable-voltage information can be used to filter states in various ways, including but not limited to the following:

Flicker Filter

Short (millisecond or less) states ("flickers") are observed with reduced current when using certain enzymes in our sequencing experiments, including the Hel308 helicase. As these states are not indicative of the DNA sequence in the pore, they should be removed prior to sequencing. Previously, these short states were not treated. Now, a software-implemented approach automatically identifies and removes these states early on in the data analysis, prior to change point detection. The removal of these flicker states reduces false positives in change point detection and cleans up the downstream signal to be used in sequencing. In some embodiments, the flicker states may be removed for purposes of change point detection, but left in the raw data to avoid reducing the amount of information available to later stages in the process.

Removal Filter

Some longer-lived (non-flicker) states in the nanopore signal are not informative of the DNA sequence moving through the pore. These uninformative "bad" states should be removed prior to sequencing. Previously, bad state removal used a simple thresholding approach on noise and mean current value. This thresholding was only effective on bad states of certain provenance and failed to remove all the uninformative states.

A trained Support Vector Machine (SVM) coupled with a logistic function can now be used to assign to each state a probability for removal. The SVM accounts for many more modes of "bad" levels than the earlier thresholding method and incorporates the state-to-state continuity information provided by the variable voltage method.

Recombination Filter

Enzyme mis-steps and over-called transitions by the change point detection algorithm can introduce repeated states into the nanopore signal. These should be identified and recombined prior to sequencing.

A "self-alignment" approach is now used to recognize repeated states, as a state will align nearly as well to its duplicate as to itself. The additional feature information provided by the variable-voltage method in describing each state improves our ability to recognize truly duplicate states.

Additionally, the continuity information between states can inform as to the likely location of enzyme backsteps. An ensemble of SVMs can be used to recognize different types of enzyme mis-steps and couple the SVM output to a set of logistic functions to obtain a probability for each type of enzyme step at each transition. These state-by-state transition probabilities are fed into the dynamic programming algorithm, which conducts the self-alignment. Inclusion of state-specific transition probabilities improves the performance of the recombination filter.

Reordering Filter

Sometimes, enzyme mis-step errors can persist in the signal even following the removal and recombination filters. The reordering filter aims to find and correct locations where enzyme mis-steps cause the observed states to be out of order.

Again, an ensemble of SVMs can be used to recognize different types of enzyme steps at each transition based on the continuity information in the variable-voltage signal. We convert the SVM outputs to a set of step-type probabilities using a set of logistic functions. Given the probabilities of each possible type of step at each state transition, we use a dynamic programming method to deduce the most likely correct ordering of states.

Model Mapping Signal to Sequence for Variable-Voltage Sequencing

To decode the DNA sequence most likely to have generated an observed series of states, a model relating the observed signal and the DNA sequence in the pore can be used.

Previously, a "4-mer" model has been used for constant-voltage sequencing, in which each 4-nucleotide combination is mapped to a predicted current signal.

A similar model is disclosed to describe the variable-voltage signal. As the DNA is moved within the pore by the voltage at each enzyme step, more than 4 nucleotides meaningfully influence the observed signal. Thus, the prior model is extended to look at longer-mers, e.g., 6 nucleotide combinations, or 6-mers. The longer, e.g., 6-mer, model is much more descriptive of the signal-to-sequence relationship and results in dramatically improved sequencing accuracy.

An initial prediction for the exemplary 6-mer variable-voltage model was made by extending the known constant-voltage 4-mer model. Then, various genomic DNA are measured in variable-voltage experiments and aligned the resulting reads to the predicted model in order to generate an updated, empirical version. Alignments were conducted using the BCJR alignment algorithm (in lieu of the Viterbi alignment algorithm as had been used previously). This algorithm allowed assignment of likelihoods that each observation was correctly interpreted, and thus update the model preferentially using the best observations. Following this process, several 6-mer states remained un-measured or poorly measured. These missing states were filled in using a small set of short custom oligonucleotides. These oligonucleotides were designed to parsimoniously cover all missing 6-mers using a de Bruijn graph approach to create a sequence containing all desired 6-mers in as short a sequence as possible.

Techniques for Decoding the DNA Sequence from the Observed Signal

A hidden Markov Model (HMM) solver is typically used to decode the DNA sequence from the observed nanopore signal. A similar technique was used in the past for sequencing constant-voltage nanopore data. The inventors have adapted and improved this technique to perform better on variable-voltage nanopore data.

Example work in this disclosure utilizes a different enzyme to control DNA motion through the pore (Hel308 helicase), which takes 2 steps per nucleotide, rather than 1. Each of the two steps is about a half nucleotide long. Use of this two-step enzyme improves sequencing by providing two measurements per nucleotide rather than 1. The HMM solver to account has been adapted for this two-step behavior.

The previous version of the HMM solver assigned uniform probabilities of various possible state transition types at each transition in the data. The state-to-state continuity information is now used to generate tailored transition probabilities at each state transition. Similar to the state filtering process, an ensemble of SVMs coupled with logistic functions can be used to generate the probabilities of possible transition types at each state transition. This approach dramatically improves the ability to identify locations in the data where information has been missed and corrected for this during sequencing.

The Hel308 helicase enzyme has been found to primarily take backsteps from only one of its two sub-nucleotide states. The HMM solver has been adapted to use the information of which observed states in the signal were found to exhibit backsteps and introduce a priori to prefer decoding these backstep states into the correct one of the two possible Hel308 sub-states. The incorporation of this kinetic knowledge simplifies the decoding of states observed to take backsteps.

The HMM solver uses a comparison of each observed signal state against the entire library of possible signals in the 6-mer model (4096 possible 6-mers and two steps per base produce 8192 possible model signals). For long sequences, this comparison can become computationally expensive. A cutoff mechanism can be introduced into the signal comparison software that allows one to only compute similarity to model states yielding a reasonably good match score while skipping over those yielding poor scores unlikely to represent a correct match. This cutoff mechanism dramatically reduces the computational load while having no adverse effect on the quality of the sequencing.

Constructing a 6-MER Model

General Considerations

To sequence the variable-voltage reads, we determine the DNA sequence most likely to have generated the observed series of conductance states. In order to decode this DNA sequence, we use a map relating the conductance signal and the DNA sequence in the pore. The nanopore signal is modeled as being generated by the k nucleotides (i.e. the k-mer, with k an integer) nearest the constriction of the pore. This model is described by a map of the $4^k$ possible k-mers to the conductances typically observed when they are in the pore. The k-mer model has been previously validated as an effective model for nanopore signal prediction.

Previous work on constant-voltage nanopore DNA sequencing used a model with k=4, but we found that a 4-mer model was insufficient for our variable-voltage signal. During variable-voltage sequencing, the nucleotides centered within the nanopore constriction at each enzyme registration are shifted forwards and backwards as the DNA is stretched by the changing voltage. This shifting means that the nucleotides both 5' and 3' of the central 4-mer have more of an effect on the observed signal when using variable-voltage than they had in the constant-voltage case. To better model this effect, we expanded the model from 4-mers to 6-mers, now including an additional nucleotide on both the 5' and 3' ends of the previous 4-mers, expanding our model from $4^4=256$ 4-mers to $4^6=4096$ 6-mers.

Each state in the variable-voltage model is characterized by more complex information than in the constant-voltage model. In the constant-voltage model, each k-mer state was characterized by its mean conductance value (G), its typical conductance noise (dG), and the variance of both of these quantities. In contrast, during variable-voltage sequencing, the k-mer state occupied at each enzyme step is not a constant conductance value characterized by a mean and noise, but instead a conductance vs. voltage (G-V) curve.

We found that each variable-voltage k-mer state is well characterized by its 3 principle component amplitudes p and their covariance $\Sigma^p$. This relationship is used in the discussion below relating to block 410 of the method 400 illustrated in FIG. 4.

Previous work by our lab used the Φ29 DNA polymerase (DNAP) as the motor protein controlling the DNA, which steps in full nucleotide increments. In some embodiments of the present disclosure, the Hel308 DNA helicase is used as the motor protein instead, which takes two distinct steps per nucleotide: an ATP-dependent step and an ATP-independent step. As the signal contains two distinct enzyme states per nucleotide, each single k-mer is now associated with two distinct states, and the 4096 6-mers in the model represent 8192 total states, two for each k-mer.

Initial Model

To construct the variable-voltage 6-mer model for the two-step-per-nucleotide Hel308 helicase motor protein, we refined the existing constant-voltage 4-mer model. We note that the 6-mer denoted $N_1N_2N_3N_4N_5N_6$ (where $N_i$ denotes a nucleotide A, C, G, or T) is made up of 3 distinct 4-mers: $N_1N_2N_3N_4$, $N_2N_3N_4N_5$, and $N_3N_4N_5N_6$. Additionally, we recall that the variable-voltage signal samples the conductance of the translocating DNA as a function of position. This function should interpolate smoothly between the discrete samples taken at constant voltage. We approximate the smooth conductance vs. position curve interpolating the DNA positions between the three constituent 4-mers by a quadratic fit to the three conductances known from the phi29 DNAP 4-mer model.

Figure 6A:
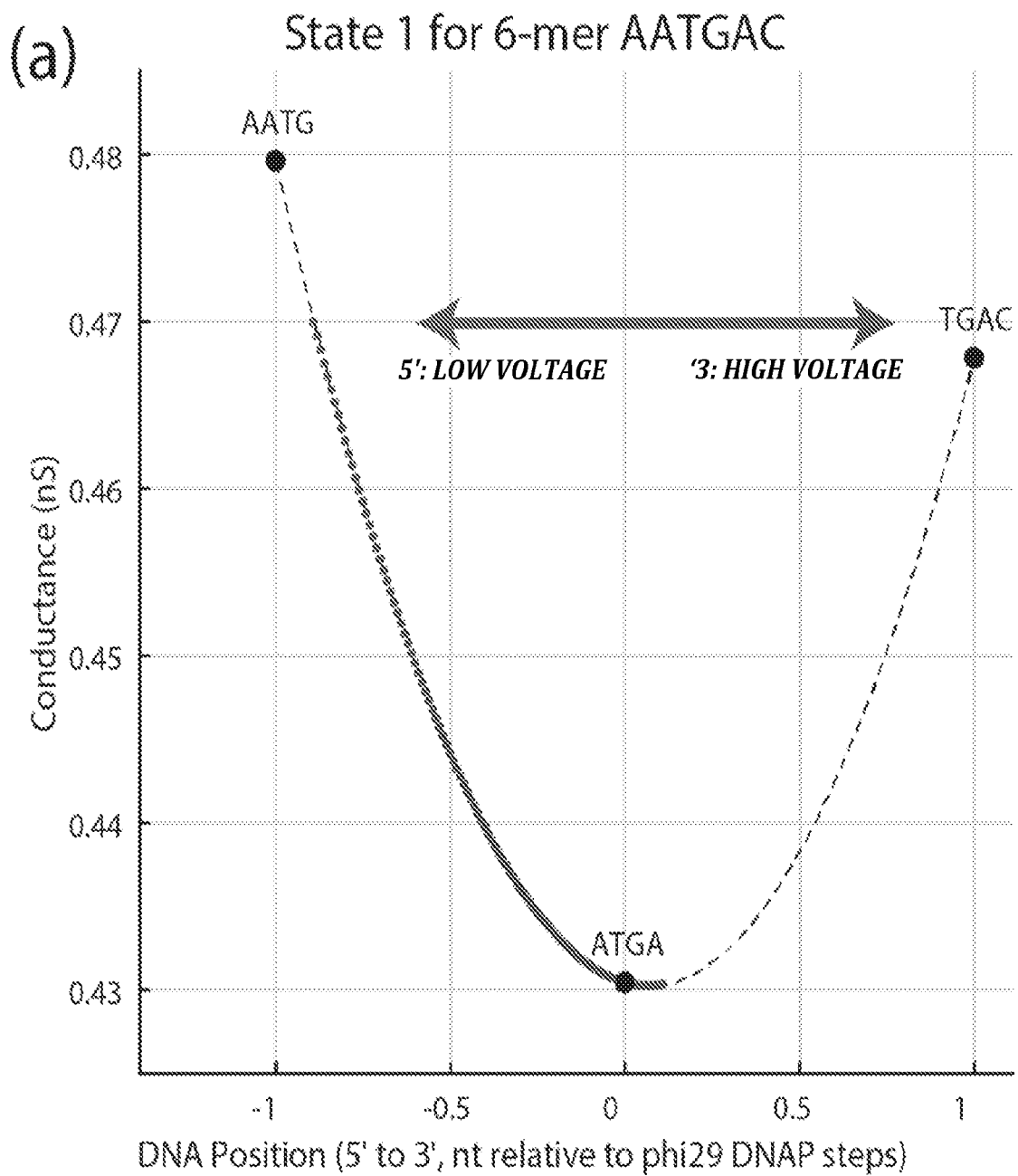
FIG. 6 includes two charts that illustrate example aspects of generating variable-voltage Hel308 helicase 6-mer predictions from the constant-voltage Φ29 DNAP 4-mer model according to various aspects of the present disclosure.
Figure 6B:
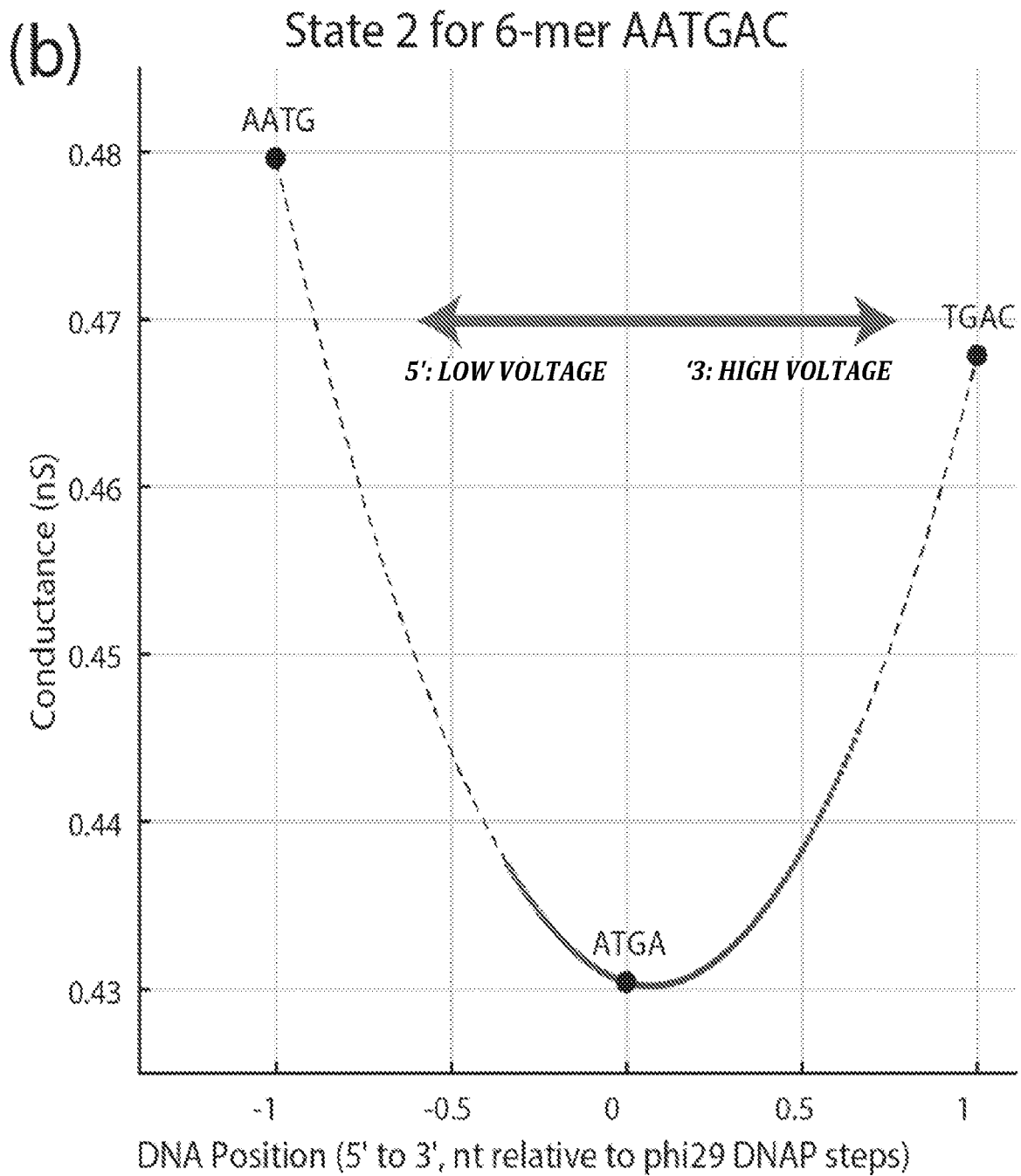

FIG. 6 includes two charts that illustrate example aspects of generating variable-voltage Hel308 helicase 6-mer predictions from the constant-voltage Φ29 DNAP 4-mer model according to various aspects of the present disclosure. The large points show the constant-voltage 4-mer model predictions for the 3 4-mers comprising the 6-mer of interest. The curved dashed line shows the quadratic fit to the 4-mer model predictions, which acts as an estimate of the smooth conductance vs. position profile explored by variable-voltage. The shaded points show the predicted conductance as a function of DNA position for the given 6-mer. The shaded points correspond to lower voltages to the left of the charts, and transition to higher voltages to the right of the charts. Chart (a) illustrates a prediction for the first of the two Hel308 states. The first of the two Hel308 states has the same DNA registration within the pore as the Φ29 DNAP full-nucleotide steps. The conductance value of the Hel308 state 1 prediction coincides with the Φ29 DNAP conductance prediction for the central 4-mer in the 6-mer of interest. Chart (b) illustrates a prediction for the second of the two Hel308 states. The second state is shifted 0.55 nt to the 3' of the first state.

Sampling this curve at the appropriate DNA positions gives an estimate of the variable-voltage 6-mer states. The first of the two Hel308 helicase states is known to have the same DNA registration within the pore as Φ29 DNAP. The constant-voltage model was derived from experiments run at a bias of 180 mV, and we know from the DNA force-extension curve (as discussed below) that the variable-voltage sweep stretches the DNA ~+0.1 nt from the 180 mV position at its highest voltage and ~−0.9 nt from the 180 mV position at its lowest voltage. So, to predict the state 1 conductance vs. position curve, we sample the interpolating curve at equally spaced points from −0.9 nt to +0.10 nt (FIG. S1a). The second of Hel308's two states is 0.55 nt 3' from state 1. So, state 2 is predicted by sampling the interpolating curve between −0.35 nt and 0.65 nt (chart (b) in FIG. 6).

The amplitudes of the 3 principle components p for each 6-mer state can now be calculated from the predicted G-V curve, as discussed below at block 410 of the method 400 illustrated in FIG. 4. All 8192 states in the initial guess map were assigned the same default covariance for their 3 principle components. The 3 principle components are sufficient for this initial model to provide a framework on which to build an empirical 6-mer model based on measurements of DNA under variable-voltage conditions.

Measuring Genomic DNA of Known Sequence

To build the 6-mer model we will ultimately use for DNA sequencing, we measure the signal produced by all 4096 of the 6-mers during variable-voltage experiments. We read DNA of known sequence under the variable-voltage sequencing conditions, then use the measured signals of this known DNA to update the initial 6-mer model.

ΦX174

Figure 7:
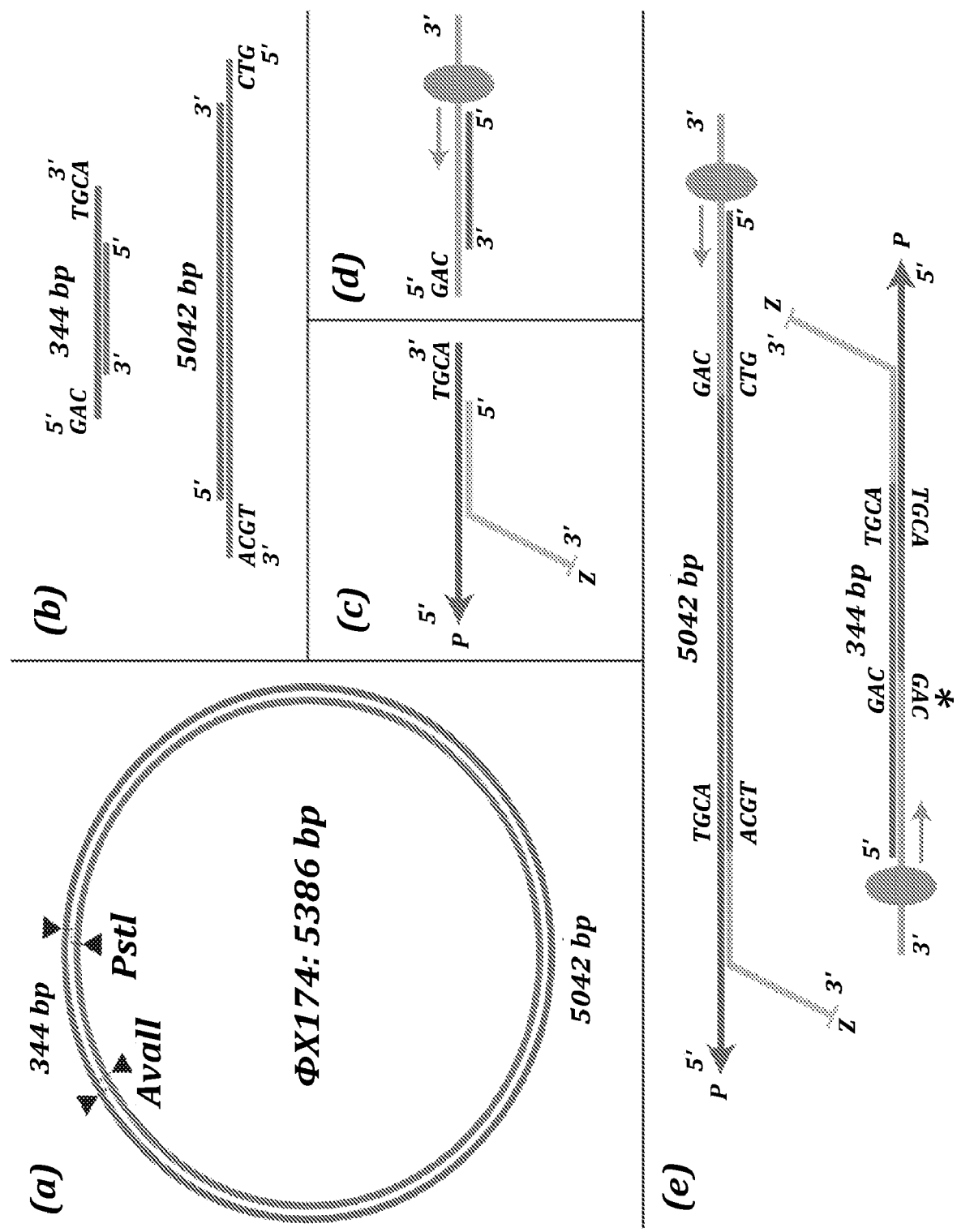
FIG. 7 includes several diagrams that illustrate various aspects of an example measurement of the ΦX174 genome.

We first measured the 5386 bp ΦX174 genome (New England Biolabs). FIG. 7 includes several diagrams that illustrate various aspects of an example measurement of the ΦX174 genome, and are discussed further below.

We prepared the circular genome for variable-voltage nanopore sequencing experiments as follows:

1. The circular genome was linearized via a double digest using the restriction enzymes PstI and AvaII (New England Biolabs). ΦX174 was prepared in 20 µg batches. For each batch, a mixture of (a) 40 µL of ΦX174 DNA at $$500 \frac{ng}{\mu L}$$

(b) 5 µL of 10× CutSmart (New England Biolabs) Buffer
   (c) 1 µL of PstI-HF restriction enzyme at $$100 \frac{\text{Units}}{\mu L}$$

(d) 1 µL of AvaII restriction enzyme at $$10 \frac{\text{Units}}{\mu L}$$

(e) 3 µL of molecular biology grade water was incubated at 37° C. for 60 minutes, then heat inactivated via heating to 80° C. for 20 minutes. Each of PstI and AvaII have a single cut site in ΦX174, so the double digest yields two linear fragments, one of 5042 bp, the other of 344 bp (FIG. 7, diagrams (a) and (b)), with sticky ends of size 3 and 4 nt.

2. The linearized fragments were purified from the heat-inactivated restriction enzymes on a DNA Clean and Concentrator column (Zymo Research), and eluted into 50 μL of molecular biology grade water.

3. Two DNA adapters are attached to each of the fragments enabling reading by the nanopore (FIG. 7, diagrams (c) and (d)). At one end, we ligate a threading adapter, which promotes capture a single strand into the pore, entering with the 5' end of the DNA threading into the pore. This threading adapter also features a cholesterol tagged 3' end. The cholesterol tagged 3' end inserts into the lipid bilayer, localizing the DNA strands near the pore and increasing the rate of 5' end capture. The threading adapter is made up of two partially complementary strands: the ΦX174 threading strand and the ΦX174 cholesterol blocker (Table S2, below). The threading adapter is formed at high concentration by mixing equal volumes of 12.5 μM threading strand and cholesterol blocker, then annealing to yield a 12.5 μM solution of the fully formed threading adapters. As shown in FIG. 7, diagram (c), the threading adapter includes a threading strand (dark) featuring a 5' phosphate (P, arrowhead) which promotes capture of this end by the pore, and a cholesterol blocker strand (light), featuring a 3' cholesterol tag (Z, crossbar) which associates with the lipid bilayer to concentrate the DNA constructs near the pore and increase the capture rate.

4. At the other end, we ligate a loading adapter which promotes loading of the Hel308 helicase onto the DNA construct. This adapter includes two partially complementary strands: the ΦX174 loading strand and the ΦX174 loading blocker (Table S2, below). The loading adapter is formed at high concentration by mixing equal volumes 12.5 μM loading strand and loading blocker, then annealing to yield a 12.5 μM solution of the fully formed loading adapters. As shown in FIG. 7, diagram (d), the loading adapter includes a loading strand (light) which overhangs the blocking strand (dark) at the 3' end to provide a loading site for the Hel308 helicase (ellipse). The helicase loads at the ss-dsDNA junction and proceeds to walk in a 3' to 5' direction along the loading strand (arrow).

5. The threading and loading adapters are ligated to the sticky ends of the linearized ΦX174 DNA fragments. A mixture of
  (a) 48 μL of 100 nM ΦX174 DNA
  (b) 6 μL of 10×T4 ligase buffer (New England Biolabs)
  (c) 2 μL of 12.5 μM threading adapters (to give 5:1 ratio of adapters to target sticky ends)
  (d) 2 μL of 12.5 μM loading adapters (to give 5:1 ratio of adapters to target sticky ends)
  (e) 1 μL of molecular biology grade water
  (f) 1 μL of T4 DNA ligase at $$400 \frac{\text{Units}}{\mu L} \text{(New Englad Biolabs)}$$

was incubated at 16° C. for 60 minutes, then heat inactivated by heating to 65° C. for 10 minutes.

6. The fully formed DNA constructs were purified from the remaining un-ligated adapters and the heat-inactivated ligase on a DNA Clean and Concentrator column, and eluted into 50 μL of molecular biology grade water. FIG. 7, diagram (e) shows the fully formed DNA constructs. After adapter ligation, the DNA constructs are now ready to be run in the variable-voltage sequencing experiments. Our adapters are designed such that we will read the sense (top) strand of the long fragment, and the antisense (bottom) strand of the short fragment. The asterisk marks a sticky end mismatch at the loading end of the short fragment, a byproduct of the non-palindromic AvaII cut site. Despite this mismatch, we still observe a population of reads of this smaller fragment, indicating that the loading adapter did still attach with some efficiency.

These two fragments, now with the necessary adapters attached, were run using the standard variable-voltage nanopore sequencing conditions. In total, we observed 155 individual reads comprising 188543 enzyme steps, or 94272 nucleotides.

λ Phage

In order to get better coverage of numerous 6-mers not present in the ΦX174 genome, and to increase the context diversity of all of our measurements, we next decided to measure a larger genome. For this second round of measurements, we chose the 48502 bp λ bacteriophage genome. We chose a new approach to fragmentation for this experiment in order to provide uniform read coverage over the entire genome. Due to the limited processivity of our Hel308 helicase (~1000 nt), restriction enzyme fragmentation results in most reads starting at the restriction site, but terminating prior to reading the entire fragment. Consequently, such a fragmentation gives excellent read coverage near the restriction sites, but poor coverage further away from them.

Figure 8:
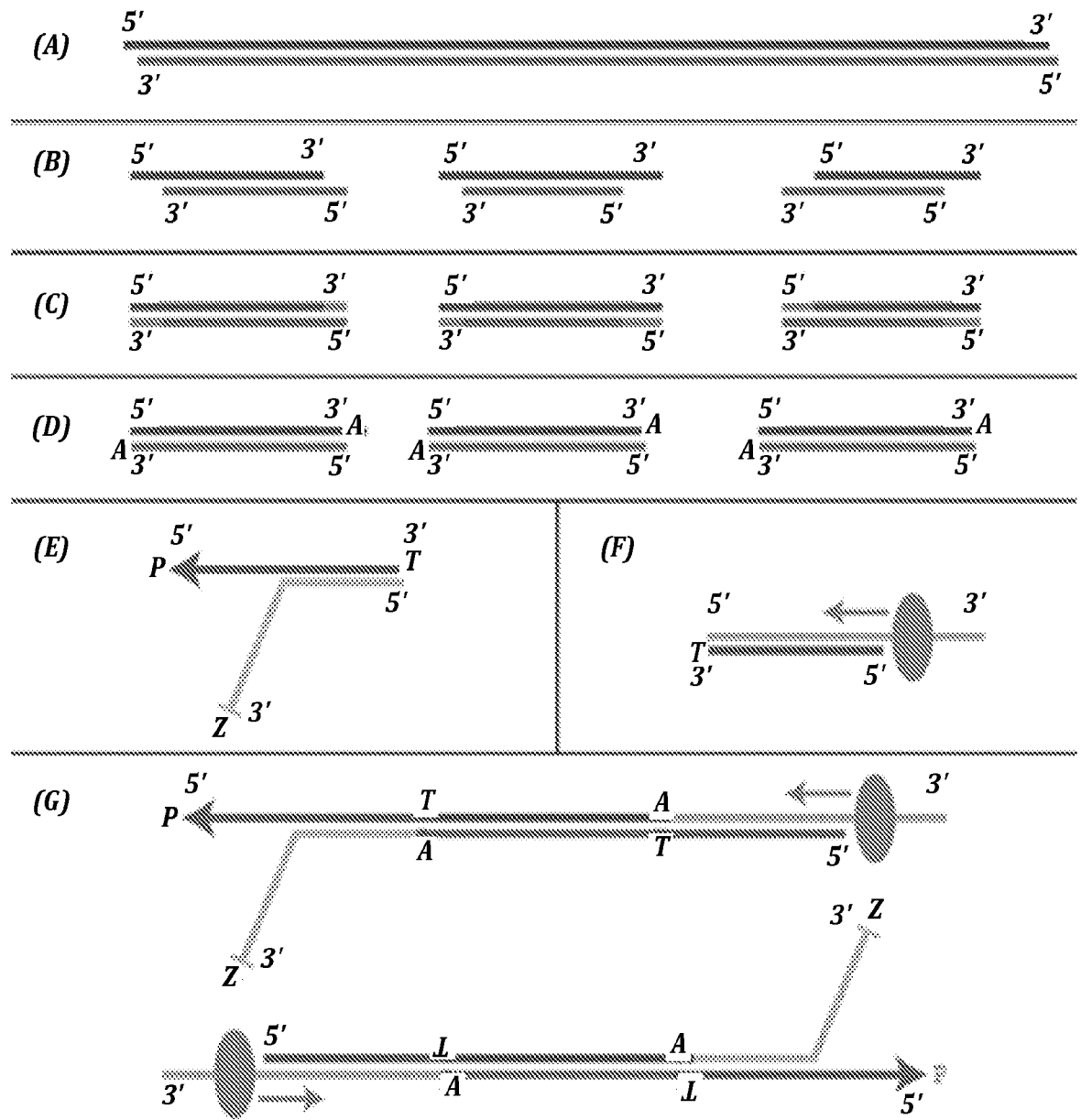
FIG. 8 includes several diagrams that illustrate various aspects of fragmentation of the λ bacteriophage genome.

FIG. 8 includes several diagrams that illustrate various aspects of fragmentation of the λ bacteriophage genome. Diagram (a) shows full length double stranded λ DNA, of 48502 bp. In diagram (b), the genomic DNA is sheared into random fragments of average length 3 kb (miniTUBE) or 6 kb (gTUBE). Diagram (c) shows that the random 3' and 5' overhangs generated through the shearing are repaired (short end segments) using the NEBNext end repair module. In diagram (d), a single base dA overhang is added to each 3' end using the NEBNext dA-tailing module. Diagram (e) shows that the threading adapter is composed of two strands. The threading strand (dark) has a 5' phosphate (P, arrowhead) to facilitate capture by the pore and a single base dT 3' overhang for ligation onto the A fragment. The cholesterol blocker (light) is partially complementary to the threading strand, with a non-complementary 3' end, and a terminal 3' cholesterol (Z, crossbar) which inserts into the lipid bilayer to up-concentrate DNA near the pore. Diagram (f) shows that the loading adapter is also composed of two strands. The loading strand (light) has an overhanging 3' end where the Hel308 helicase (ellipse) can load onto a ss-dsDNA junction, and proceed in a 3' to 5' direction along the strand. The loading blocker (dark) is complementary to the non-overhanging region of the loading strand, with a single base dT 3' overhang for ligation onto the A fragment. Diagram (g) shows the fully formed DNA constructs that are now ready to be run in variable-voltage nanopore sequencing experiments. This library preparation can obtain reads of both the sense (top construct) and antisense (bottom construct) strand.

For uniform coverage, we instead use two separate Covaris products giving random shearing over the entire genome into fragments of a well-defined size range. In one λ library preparation, we used the Covaris Blue DNA miniTUBE, which yielded random fragments of on average 3 kbp in length. For our second library preparation, we used Covaris gTUBEs to get random fragments of on average 6 kbp in length. We switched from miniTUBEs to gTUBEs simply for easy of use, as these required only a centrifuge, and not the Covaris sonicator instrument. For both shearing methods, the library preparation proceeded as follows:

1. The full length λ DNA (Promega) was fragmented using either Blue miniTUBEs (in 20 μg batches) or gTUBEs (in 30 μg batches) (FIG. 8, diagrams (a) and (b)). For miniTUBE fragmentation, 20 μg of λ DNA was suspended in Tris EDTA buffered at pH 8.0 to a total volume of 200 μL. DNA was then fragmented using the Covaris M220 Focused-ultrasonicator, using the recommended settings for product fragments of ~3000 bp in length. For gTUBE fragmentation, 30 μg of λ DNA was suspended in molecular biology grade water to a total volume of 150 μL. The gTUBE was then centrifuged on an Eppendorf 5417R centrifuge for 30 seconds at 12400 rpm (corresponding to 16200 g), resulting in fragments of ~6000 bp in length.
2. Following fragmentation, the DNA fragments have random 3' and 5' overhangs. Before proceeding with adapter ligation, we ensure that all DNA fragments are blunt-ended by running an end repair protocol, as shown in FIG. 8, diagram (c). Using the NEBNext end repair module (New England Biolabs), a mixture of
    (a) 5 μg fragmented DNA
    (b) 10 μL of NEBNext 10× End Repair Reaction Buffer
    (c) 5 μL of NEBNext End Repair Enzyme Mix
    (d) Molecular biology grade water to total volume of 100 μL
    was incubated at 20° C. for 30 minutes. The end-repaired fragments (now blunt-ended) were purified on a DNA Clean and Concentrate column.
3. After end repair, we used the NEBNext dA-tailing module (New England Biolabs) to attach a dA monomer at the 3' end of each strand as a target for adapter ligation, as shown in FIG. 8, diagram (d). A mixture of
    (a) 5 μg of λ DNA
    (b) 5 μL of 10× NEBNext dA-Tailing Reaction Buffer
    (c) 3 μL of Klenow Fragment (3'→5' exo−)
    (d) Molecular biology grade water to a total reaction volume of 50 μL
    was incubated at 37° C. for 30 minutes, then purified on a DNA Clean and Concentrate column.
4. Similar threading and loading adapters are used for variable-voltage sequencing experiments on the λ DNA as were used for ΦX174, differing only in the sequence at the sticky ends to be ligated onto the genomic DNA fragments. For the threading adapter (shown in FIG. 8, diagram (e)), equimolar parts of the A threading strand and the A cholesterol blocker (Table S2, below) were mixed and annealed to a final concentration of 10 μM. Similarly, for the loading adapter (FIG. 8, diagram (f)), equal molar parts of the A loading strand and the λ loading blocker were mixed and annealed to a final concentration of 10 μM.
5. Adapters were ligated to the dA-tailed λ DNA fragments using T4 DNA ligase (New England Biolabs). A mixture of
    (a) 10 μg of λ DNA fragments
    (b) 3 μL of 10 μM threading adapters (for a ~10:1 adapter to dA-tail end ratio)
    (c) 3 μL of 10 μM loading adapters (for a ~10:1 adapter to dA-tail end ratio)
    (d) 15 μL of 10× Ligation Buffer
    (e) 7.5 μL T4 DNA Ligase
    (f) Molecular biology grade water up to a total reaction volume of 150 μL
    was incubated at 22° C. for 125 minutes, then heat inactivated at 65° C. for 10 minutes. The ligation products (FIG. 8, diagram (g)) were purified on DNA Clean and Concentrator columns to remove the inactive ligase and residual un-ligated adapters, and eluted into molecular biology grade water.

As all the 3' ends of the λ fragments have the same single dA overhang, not all ligation products will have the correct conformation of one threading adapter and one loading adapter. 25% of the population will have loading adapters at each end, and 25% will have threading adapters at each end. This reduces the overall effective yield of this library preparation by half, but a sufficient number of constructs were well formed to allow us to generate 128 individual reads comprising 120867 enzyme steps, or 60434 nucleotides.

Building the Empirical 6-Mer Model from Genomic Reads

Having measured a total of 309410 enzyme steps along genomic DNA tracks (120867 in λ, 188543 in ΦX174) representing 154705 measured nucleotides, we now organize these measurements to empirically update the initial model of the predicted nanopore signal for each of the 8192 model states (2 enzyme states for each of the 4096 6-mers). Each observed enzyme step is a measurement of one of the two Hel38 helicase states at one of the 4096 possible 6-mers.

To update the model, we must associate the signal at each enzyme step with the sequence that generated it. We get this association by aligning the measured signal to the predicted signal for the known DNA sequence being measured (ΦX174 or λ). For the first construction of the empirical model, the predicted signal is given by the initial model described above.

Each read of genomic DNA is aligned to the predicted signal for its reference sequence using the BCJR alignment algorithm. The alignment maps the G-V curve at each measured conductance state to a state in the predicted signal, which represents a known location in the reference sequence. In addition to an alignment location, the BCJR algorithm also returns a likelihood that each alignment location is the true alignment location for the measured state. We update the mean values in the 6-mer model by filling each state in the model with the weighted average (weighted by the likelihood score of alignment) of all measured states aligning to locations in the reference corresponding to that enzyme and 6-mer state. Additionally, the covariance of each state in the model is updated with the covariance of all measured states aligning to reference locations corresponding to that state.

Figure 9:
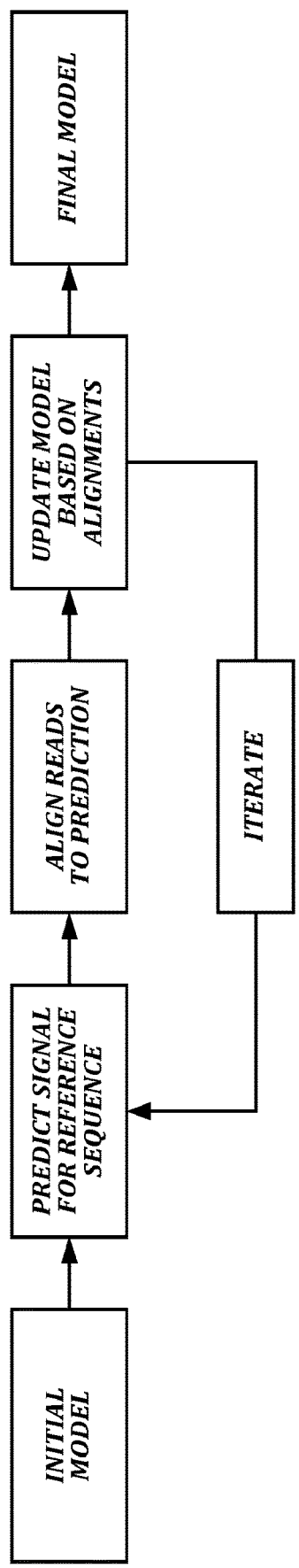
FIG. 9 is a flowchart that illustrates a non-limiting example embodiment of a method for iterating this process according to various aspects of the present disclosure.

The above procedure of generating predictions, aligning reads, and updating the predictions can be iterated. FIG. 9 is a flowchart that illustrates a non-limiting example embodiment of a method for iterating this process according to various aspects of the present disclosure. For the work presented here, we ran two iterations: one starting from the interpolated initial model and second aligning to the first version of the empirical model. Though we found that two iterations yielded a good quality model, it is possible that a larger data set of genomic DNA reads combined with further iterations of the model generation could result in an improved model.

Filling in Unmeasured 6-Mers

After constructing the empirical 6-mer model from long reads of ΦX174 and λ DNA, we found that for a small fraction (168 out of 4096) of the 6-mers, one or both of the enzyme states had not been well measured. In order to efficiently measure the remaining states, we used a de Bruijn graph approach to construct a minimal sequence of length 337 nt containing all 168 of the poorly measured 6-mers. We then split up this minimal sequence over a total of 6 short synthetic DNA oligos (Fill-in strands 1-6 in Table S2, below).

Figure 10:
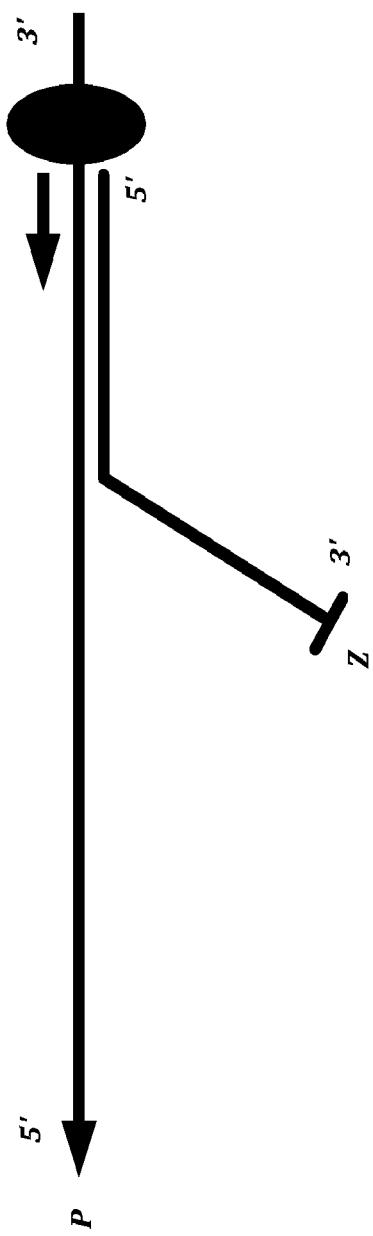
FIG. 10 is a diagram that illustrates a non-limiting example of a DNA construct for the fill-in data set according to various aspects of the present disclosure.

FIG. 10 is a diagram that illustrates a non-limiting example of a DNA construct for the fill-in data set according to various aspects of the present disclosure. DNA constructs for the fill-in data set are composed of two partially complementary short oligos. The fill-in template (one of a possible 6) on top has a 5' terminal phosphate (P, arrowhead) facilitating threading of this end into the pore. The 5' phosphate is followed by a section of the minimal sequence containing the missing 6-mers, then by a target sequence for duplexing the complementary strand, and finally an overhanging non-complementary 8 nucleotide section at the 3' end for loading the Hel308 helicase (oval). The fill-in cholesterol blocker (bottom bent bar) contains at its 5' end the complementary sequence to the target duplex sequence in the template strand. The complementary sequence is followed by a series of 4 18-Carbon spacers and a 3' terminal cholesterol tag (Z, crossbar). The 18-Carbon spacers give the construct a flexible fan-tail, and the terminal cholesterol tag associates with the lipid bilayer, up-concentrating the constructs near the pore.

We ran these 6 strands using standard variable-voltage sequencing conditions, collecting a total of 172 reads comprising 16675 enzyme steps (8338 nucleotides) across the 6 strands. Using these reads, we filled in the remaining gaps in the empirical 6-mer model using the same approach detailed above: we predicted the signal for the known sequence based on the existing 6-mer model, aligned the reads to this prediction, then updated the model based on the alignments and iterated the process. We iterated the predict/align/update cycle 10 times for the short strands in order to generate the final version of the 6-mer model which we ultimately use for sequencing.

Constant-Voltage Model Extraction

The variable-voltage 6-mer map contains as a subset all the information required for a constant-voltage 6-mer model. In evaluating the performance of the two sequencing methods, we used the constant-voltage 6-mer model extracted from the variable-voltage model to provide a fair test. By doing this, any errors present in one model detracting from the sequencing accuracy will be present in both models, and will affect the accuracy of both methods equally.

The constant-voltage model is extracted from the variable-voltage model. The constant-voltage mean conductance for each 6-mer is extracted from the corresponding variable-voltage conductance curve by taking the value of the curve at the point corresponding to 180 mV (the operating voltage for our constant-voltage sequencing experiments). The variance of the mean constant-voltage conductance is taken as the variance in the value of the variable-voltage conductance curve at that same point.

Figure 11:
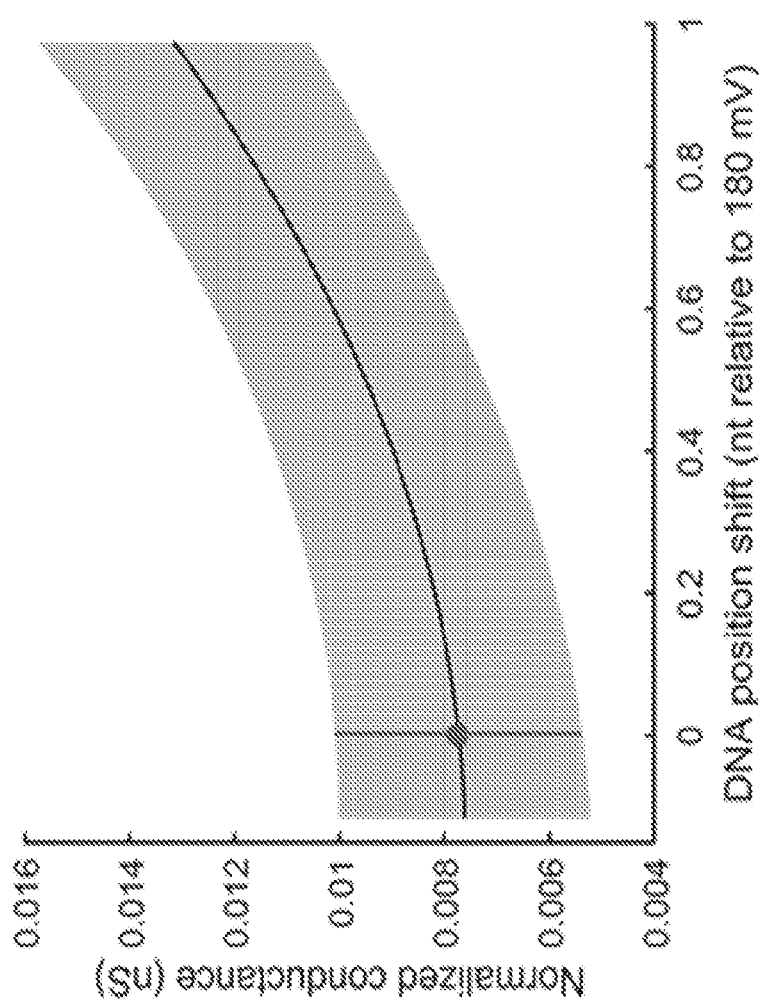
FIG. 11 is a chart that illustrates a non-limiting example embodiment of extraction of the constant-voltage model from the variable-voltage model according to various aspects of the present disclosure.

FIG. 11 is a chart that illustrates a non-limiting example embodiment of extraction of the constant-voltage model from the variable-voltage model according to various aspects of the present disclosure. The constant-voltage model value for a given 6-mer (e.g. A TGAGA) is taken as the point (dot) in the variable-voltage conductance curve for that 6-mer in the variable-voltage model (black curve) corresponding to 180 mV (0 nt shifted relative to 180 mV). The uncertainty (vertical line) is taken as the variation in the variable-voltage model prediction (shading) at the 180 mV point.

Example Sequencing Method

Figure 4:
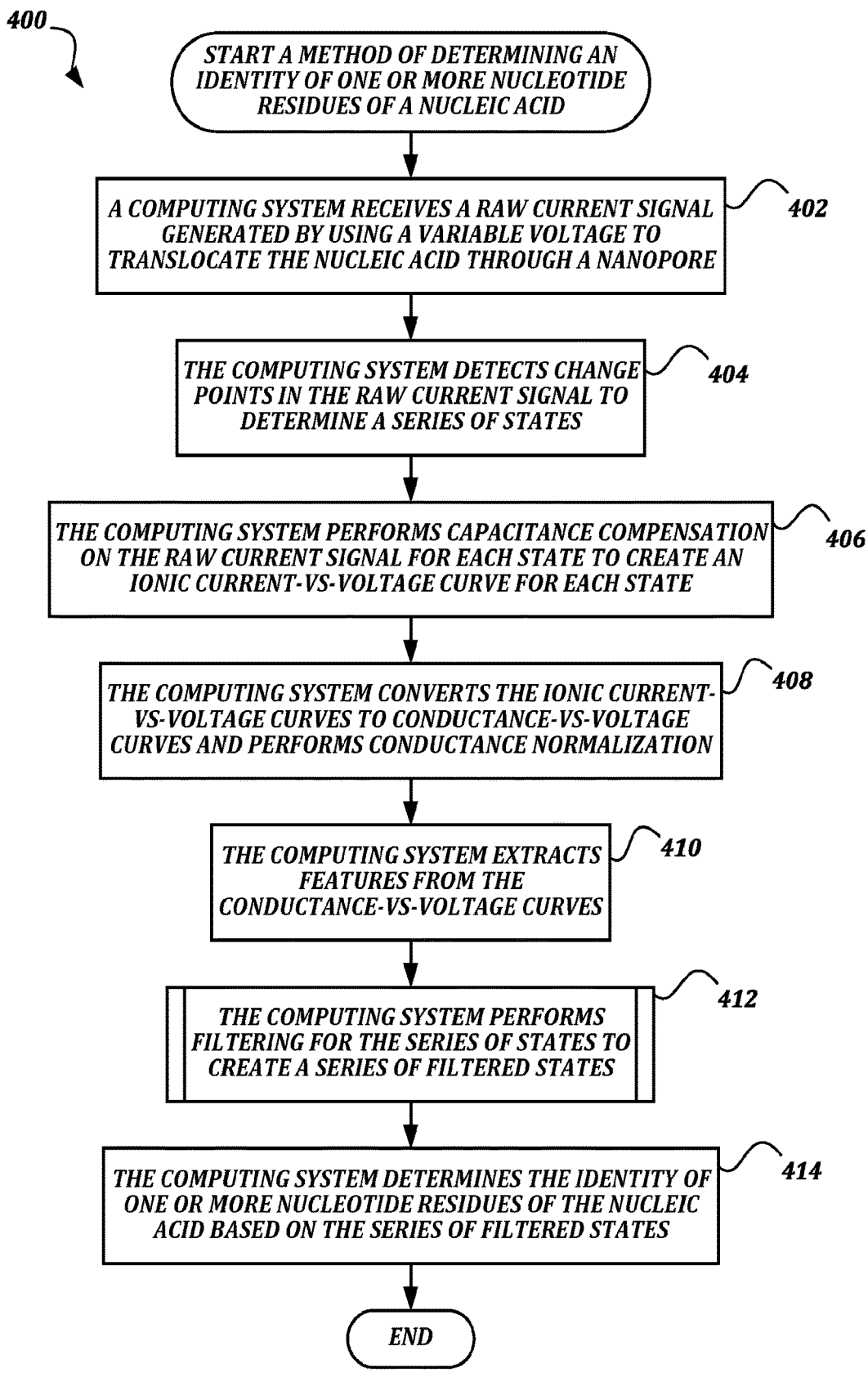
FIG. 4 is a flowchart that illustrates a non-limiting example embodiment of a method of determining an identity of one or more nucleotide residues of a nucleic acid according to various aspects of the present disclosure.

FIG. 4 is a flowchart that illustrates a non-limiting example embodiment of a method of determining an identity of one or more nucleotide residues of a nucleic acid according to various aspects of the present disclosure. As mentioned above, though the discussion herein focuses on the determination of nucleotide residues of a nucleic acid, this is merely an example, and in other embodiments another polymer analyte (such as a protein) may be analyzed to determine its monomer subunits (such as amino acids).

From a start block, the method 400 proceeds to block 402, where a computing system receives a raw current signal generated by using a variable voltage to translocate the nucleic acid through a nanopore. The raw current signal is generated using a technique as discussed herein, at least in FIGS. 1-3 and the associated descriptions thereof.

In some raw current signals, including but not limited to Hel308-controlled DNA translocation data, we observe short-lived states of a particular character which we refer to as "flickers." These states are milliseconds or less in duration, always have a lower conductance than the state they start from, and always return to the state they started in. These flicker states cannot be mapped to any predicted conductance state when reads are compared against the predicted signal for the known DNA sequence, and are thus not informative in decoding the DNA sequence. We avoid considering these flickers during some of the data processing during the method 400 (including change point detection) as their presence decreases the performance and accuracy of certain processing. During other data processing during the method 400, the flickers may be left in the processed data.

In variable-voltage data, flickers are identified and removed by the removal filter, as discussed below, because their conductance curves look starkly different from normal data. To remove these transients from the constant-voltage data, we search for outlying low states of short duration. We score every individual conductance measurement xn in a read with a one-sample t-test against the data surrounding it:

$$t_n = \frac{x_n - \mu_{[n-k,n+k]}}{\sigma_{[n-k,n+k]}}$$

where $$\mu_{[n-k,n+k]} = \frac{1}{2k}\left[\left(\sum_{m=n-k}^{n+k} x_m\right) - x_n\right]$$

and $$\sigma^2_{[n-k,n+k]} = \frac{1}{2k}\left[\left(\sum_{m=n-k}^{n+k} x_m^2\right) - x_n^2\right] - \mu^2_{[n-k,n+k]}$$

are the mean and variance of the data k points to the left and right of the point being scored, not including the point itself. We discard any points $|t_n|>e$, where e is a threshold chosen to specify the desired aggressiveness of the filter. This procedure is iterated with a fixed threshold e and window k until no more points are removed, then repeated a second time with a larger window k. In the constant-voltage sequencing data in this work, we use e=3 for both iterations and k=2 for the first iteration and k=5 for the second. Filtering is done on the 5 kHz time series data.

Figure 12:
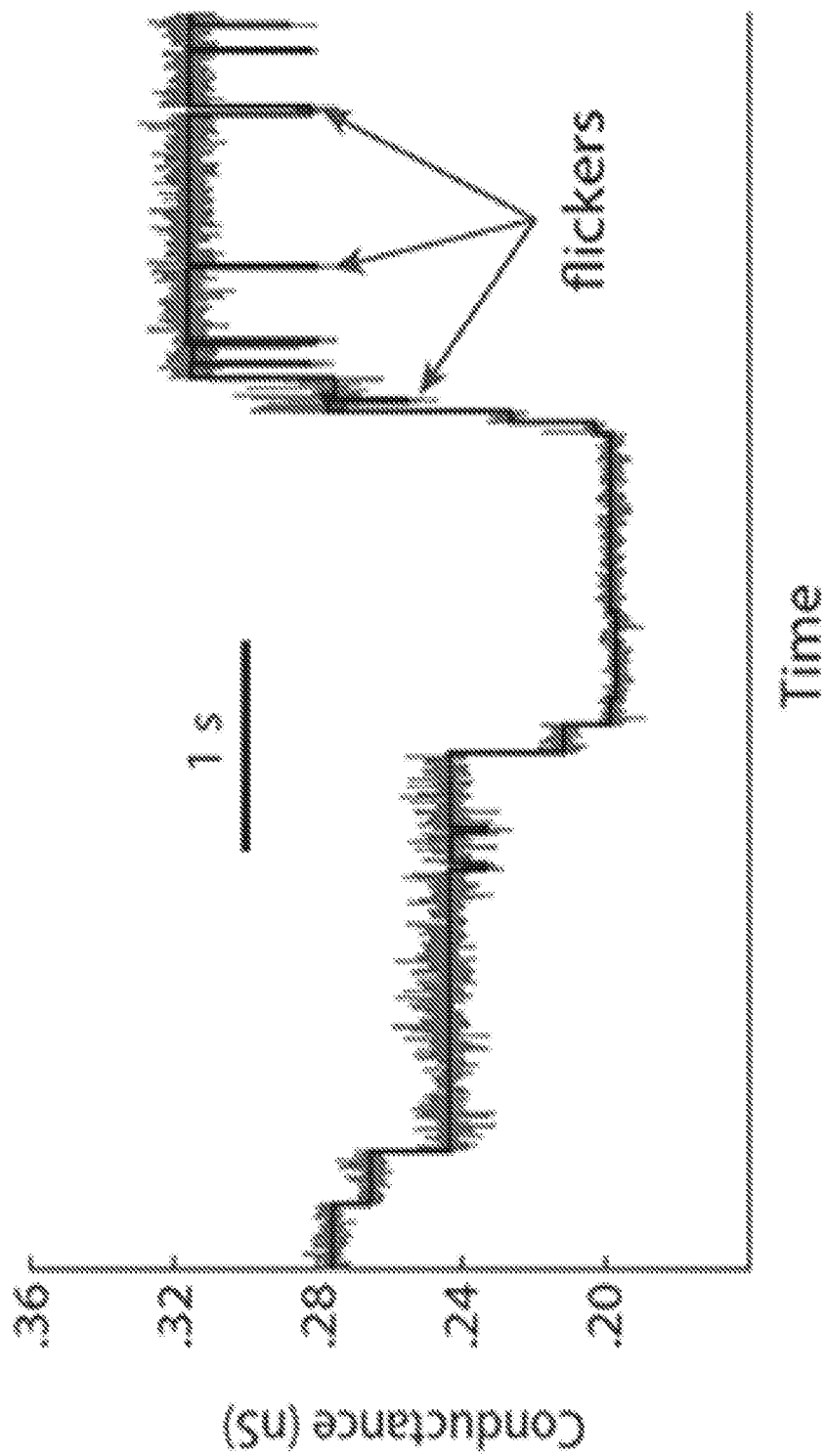
FIG. 12 is a chart that illustrates a non-limiting example of flicker states in a raw current signal according to various aspects of the present disclosure.

FIG. 12 is a chart that illustrates a non-limiting example of flicker states in a raw current signal according to various aspects of the present disclosure. The raw ionic current trace (downsampled to 5 kHz) for a Hel308-controlled DNA translocation event is shown, with the states found by the change point detection algorithm overlaid in black. The arrows identify several flickers-transient decreases in the ionic current that are not cannot be mapped to any sequence state.

Returning to FIG. 4, at block 404, the computing system detects change points in the raw current signal to determine a series of states. Each state is intended to represent a segment of the raw current signal corresponding to an enzyme step. Partitioning simplifies the data stream passed to the hidden Markov model by turning the many noisy measurements making up an enzyme step observation into a series of a few low-noise parameters describing each step. In the case of constant-voltage sequencing, each enzyme step is described by a mean ionic current and an associated variance. For variable-voltage sequencing, we use the coefficients of the top three principal components, along with their associated covariance (as discussed below).

Figure 13:
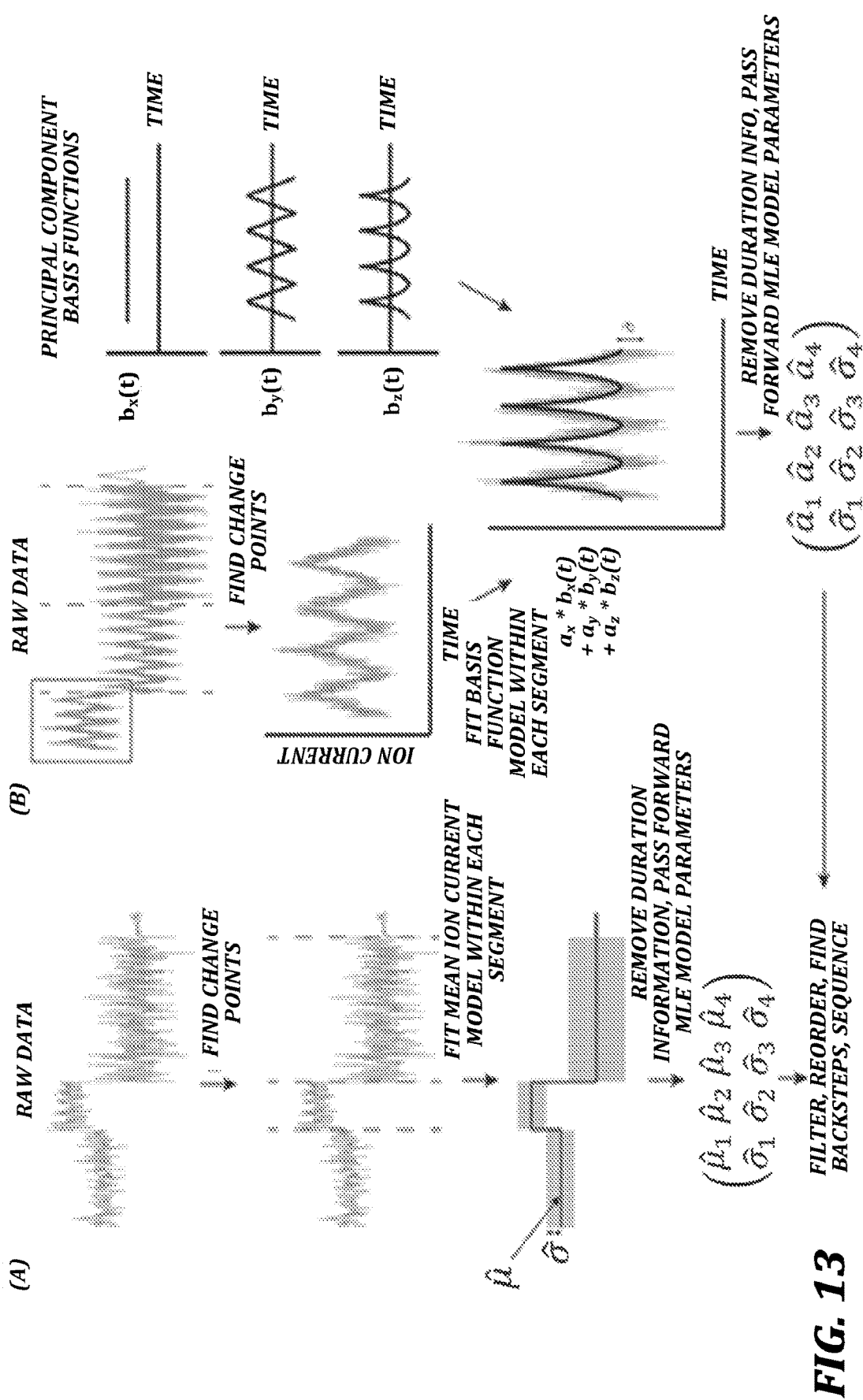
FIG. 13 includes several charts that illustrate non-limiting example embodiments of change point detection of constant-voltage raw current data and variable-voltage raw current data according to various aspects of the present disclosure.

FIG. 13 includes several charts that illustrate non-limiting example embodiments of change point detection of constant-voltage raw current data and variable-voltage raw current data according to various aspects of the present disclosure. Section (a) illustrates constant-voltage data. For constant-voltage experiments, change point detection involves finding transitions between states of different ionic current means and variances. Section (b) illustrates variable-voltage data. For variable-voltage experiments, we are looking for changes in the parameters of a time-dependent model describing the data. The model we use is a sum of basis functions which are the principal components of the nanopore signal, parameterized by the amplitude of each basis function.

In some embodiments, the data is partitioned into enzyme steps using a change point detection technique. The same fundamental technique works for both constant-voltage and variable-voltage sequencing data. Simply, change point detection chooses between two competing hypotheses. Given a segment of data $\{x_i\}$, is the data best modeled by a single model (parameterized as $\theta_T$) or by two models ($\theta_L$, $\theta_R$) each separately describing the data to the left and right of some transition point t? If the single-model hypothesis proves better, no change point is present in the segment. If the two-model hypothesis is better, a change point is called at the best transition point.

The basic considerations in this type of technique are how to model the data, and how to prevent over-calling transitions. In the case of constant-voltage data, we use a mean ionic current and a variance to describe the individual states. We modeled the variable-voltage data by the five largest principal components of the periodic functions that represent the raw data of each enzyme state.

Figure 14A:
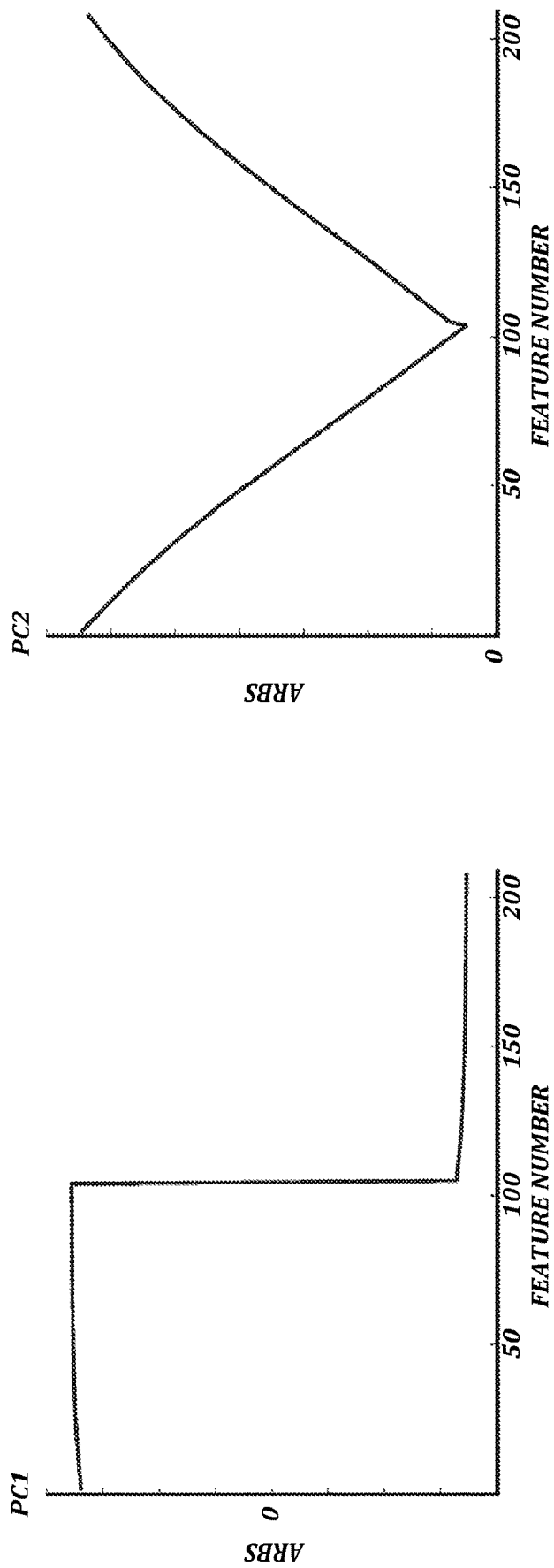
FIG. 14 includes charts that illustrate non-limiting examples of principal components for change point detection according to various aspects of the present disclosure.
Figure 14B:
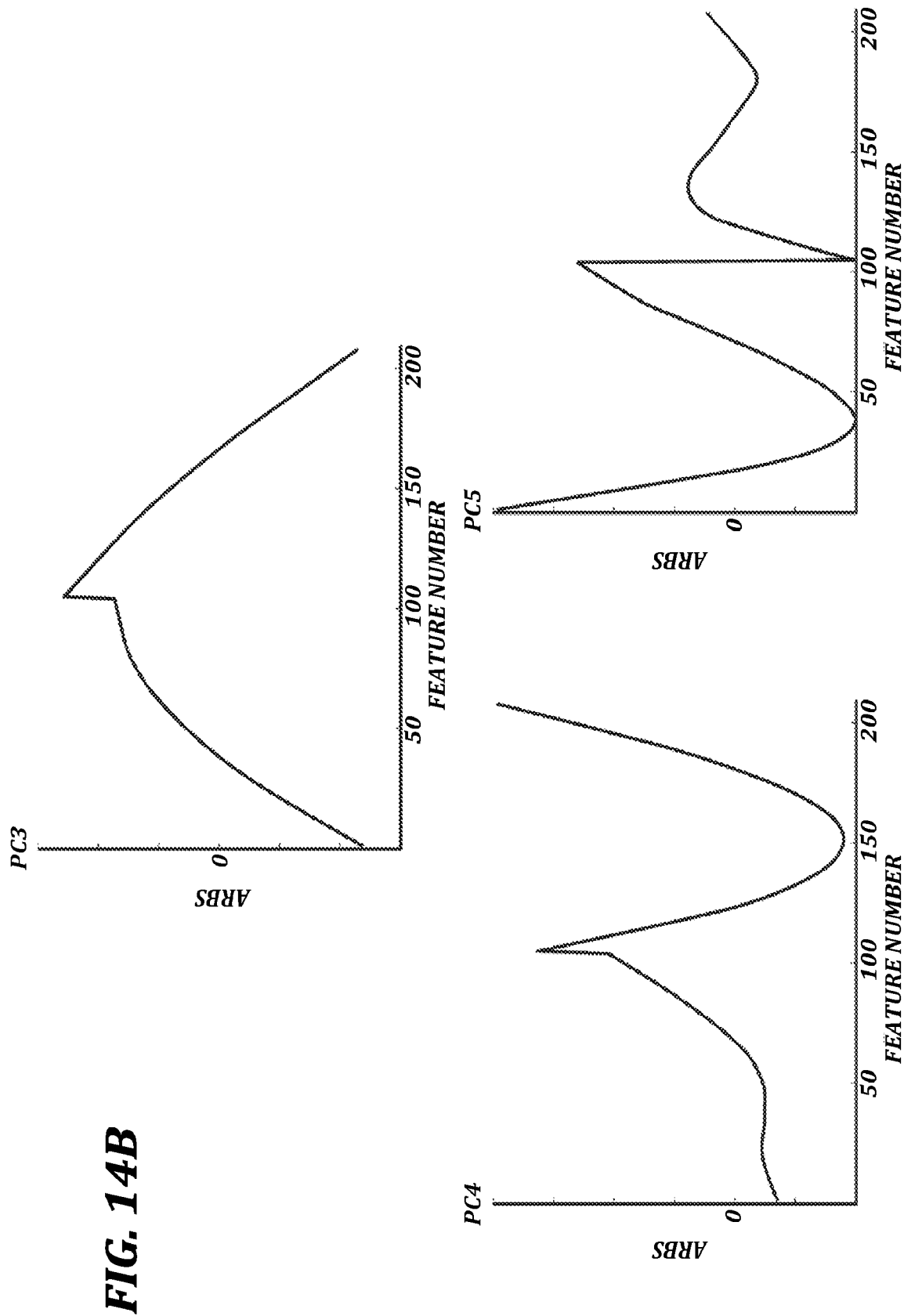

FIG. 14 includes charts that illustrate non-limiting examples of principal components for change point detection according to various aspects of the present disclosure. The five principal component vectors used to model the variable-voltage time series date are shown. Linear combinations of these five vectors can describe the observed data. These principal components were determined by choosing change points by-eye, then averaging each enzyme state into a single 250-sample period of the waveform We then treated each state as a separate measurement for the purposes of principal component analysis. The principal components provide a descriptive, concise basis with which we can describe the variable-voltage time series data.

The over-calling issue is a consequence of the fact that a model with more parameters can always describe a data set better than a model with fewer parameters, even if it is not actually more predictive. Consequently, the two-model hypothesis will always fit the data better—the question is rather is it sufficiently better to justify the addition of more parameters into our description of the data? We correct this bias by penalizing the addition of extra parameters, using the results of Lamont and Wiggins to determine the appropriate penalty.

FIG. 26 is a pseudo-code listing that describes a non-limiting example embodiment of a change point detection technique according to various aspects of the present disclosure. The following is a full mathematical description of the change point detection procedure.

The change point problem is formulated mathematically as follows: given a time series of d-dimensional data $\{x_1, x_2, \ldots, x_N\}$, $x \in \mathbb{R}^k$, choose a model consisting of some number of change points $\{t_a, t_b, \ldots\}$, and a different set of parameters $\{\theta_a, \theta_b, \ldots\}$ describing the data between each change point. Our change point detection technique finds a close-to-optimal partitioning of time series data using this model.

We assume each state is a function $f$ of time t and parameters $\theta$ with normally distributed noise $\sigma$. Under these assumptions, the probability density of obtaining a measurement x(t) at a time t given a choice of parameters $\theta$ for that time is $$p(x(t), t \mid \theta) = \frac{1}{\sqrt{2\pi\sigma^2}} e^{-\frac{(f(t;\theta) - x(t))^2}{2\sigma^2}}$$

For a number of measurements indexed by time t=1, 2, 3, ..., the probability density is the product of the probabilities of each measurement:

$$p(x \mid \theta) = \prod_{t=1}^{N} \frac{1}{\sqrt{2\pi\sigma^2}} e^{-\frac{(f(\theta)_t - x_t)^2}{2\sigma^2}}$$

We convert this probability into a log-likelihood $L(\theta|x) = p(x|\theta)$ to simplify calculations, giving $$\log \mathcal{L} = -\frac{1}{2} \sum_{t=1}^{N} \log 2\pi\sigma^2 + \frac{(f(\theta)_t - x_t)^2}{\sigma^2}$$

For change point detection, we are interested in the relative likelihood between using two different sets of parameters $\theta_L$ and $\theta_R$ to model the data to the left and right of a possible change point, versus using one set of parameters $\theta_T$ to describe the total region in question. Defining the first time index of the region as L, the final index as R, and the number of points to the left, the right and in the whole region as $N_L$, $N_R$, and $N_T = R - L + 1$ respectively, the relative log-likelihood is $$\log \mathcal{L} = -\frac{1}{2} \left[ \sum_{t=L}^{L+N_L-1} \log 2\pi\sigma_L^2 + \frac{(f(\theta_L)_t - x_t)^2}{\sigma_L^2} + \sum_{t=L+N_L}^{N_T} \log 2\pi\sigma_R^2 + \frac{(f(\theta_R)_t - x_t)^2}{\sigma_R^2} - \sum_{t=L}^{L+N_T-1} \log 2\pi\sigma_T^2 + \frac{(f(\theta_T)_t - x_t)^2}{\sigma_T^2} \right]$$

If our maximum likelihood estimate for $\theta$ given the data is $\hat{\theta}$, the residual variance is $$\hat{\sigma}^2 = \frac{1}{N}\sum_t (f(\hat{\theta})_t - x_t)^2.$$

We find the maximum log-likelihood $\log \hat{\mathcal{L}}$ by plugging in these estimators:

$$\log\hat{\mathcal{L}} = -\frac{1}{2}$$

$$\left[ N_L \log 2\pi\hat{\sigma}_L^2 + N_L \frac{\hat{\sigma}_L^2}{\hat{\sigma}_L^2} + N_R \log 2\pi\hat{\sigma}_R^2 + N_R \frac{\hat{\sigma}_R^2}{\hat{\sigma}_R^2} - N_T \log 2\pi\hat{\sigma}_T^2 - N_T \frac{\hat{\sigma}_T^2}{\hat{\sigma}_T^2} \right] =$$

$$-\frac{1}{2}\left[ N_R \log\hat{\sigma}_R^2 + N_L \log\hat{\sigma}_L^2 - N_T \log\hat{\sigma}_T^2 \right]$$

This is the correct expression for the log-likelihood of a fit, giving the most descriptive model of the data. However, we are not interested in the most descriptive but rather the most predictive model. To find this, we need to correct for the tendency to over-fit. We can always fit better by partitioning data and supplying more parameters, but we lose information by doing so. This leads to an over-fitting bias. To correct for this, we use the results of LaMont and Wiggins to subtract this bias. In general, the bias is a function of the number of points $N_T$ and the dimensionality of the data being partitioned d, and is calculated through Monte Carlo simulations and either fitted or used as a lookup table. The test statistic is $$CPIC = -\log\hat{\mathcal{L}} + p(N, d) = \frac{N_R}{2}\log\hat{\sigma}_R^2 + \frac{N_L}{2}\log\hat{\sigma}_L^2 - \frac{N_T}{2}\log\hat{\sigma}_T^2 + p_d(N_T)$$

where $p_d(N_T)$ is the penalty for adding parameters in modeling $N_T$ d-dimensional data points. The natural choice is to call a level transition if $CPIC_p<0$. One way to tune the sensitivity of this score is to apply a multiplier $\lambda>0$ to $p_d$, which can be made higher to increase the penalty and find fewer levels. This is done to compensate for a model that does not exactly describe the data; we choose $\lambda=4$ because it provides empirically good results. So the final score used is $$CPIC(\lambda) = \frac{N_R}{2}\log\hat{\sigma}_R^2 + \frac{N_L}{2}\log\hat{\sigma}_L^2 - \frac{N_T}{2}\log\hat{\sigma}_T^2 + \lambda p_d(N_T)$$

To calculate the $\hat{\sigma}$'s, we need to determine the maximum likelihood estimates of the model parameters $\hat{\theta}$. Obtaining these can in general be slow and difficult, possibly even requiring nonlinear optimization not guaranteed to converge. However, in certain situations it is easy, and we can even take advantage of some tricks to avoid redundant calculation. The simplest example is the case of constant levels about a single mean. The maximum likelihood estimate of the mean in bounds [L, R] is $$\hat{\mu} = \frac{1}{R-L+1}\sum_{t=L}^{R} x_t$$

We can avoid continually re-adding the same points together by instead defining and pre-calculating the cumulate $X_t = \sum_{s=1}^{t} x_s$, in which case our expression for the mean is simply $$\hat{\mu} = \frac{X_R - X_L}{R-L+1}.$$

This difference is much more expedient to calculate than the mean, and the calculation of its value for many possible transition points may be vectorized. We can use a similar technique to calculate the variance, $$\hat{\sigma}^2 = \frac{1}{R-L+1}\sum_{t=L}^{R}(x_t - \hat{\mu})^2 = \left[\frac{1}{R-L+1}\sum_{t=L}^{R} x_t^2\right] - \hat{\mu}^2$$

Again defining and pre-calculating the cumulate sum $$X_t^2 = \sum_{s=1}^{t} x_s^2,$$

we quickly calculate the MLE variance as $$\hat{\sigma}^2 = \frac{X_R^2 - X_L^2}{R-L+1} - \hat{\mu}^2.$$

In general, the function $f(\theta)$ may depend on time. One case is if we can write $f(\theta)_t$ as a sum of p basis functions $b_{it}$ with amplitudes $\theta_i$, $$f(\theta)_t = \sum_{i=1}^{p} \theta_i b_{it}.$$

Assuming again normally distributed random errors, we find maximum likelihood estimators $$\hat{\theta} = \mathrm{argmin}_\theta \sum_{t=L}^{R}\left(x_t - \sum_{i=1}^{p}\theta_i b_{it}\right)^2$$

To this end, we set the derivative of the sum squared error to zero, $$2\sum_{t=L}^{R}\left(x_t - \sum_{i=1}^{p}\hat{\theta}_i b_{it}\right)b_{jt} = 0$$

$$\sum_{t=L}^{R} x_t b_{jt} = \sum_{i=1}^{p}\hat{\theta}_i \sum_{t=L}^{R} b_{it} b_{jt}$$

Both of these sums over time are again precalculable from cumulates, which we define as $$B_{ijt} = \sum_{s=1}^{t} b_{it} b_{jt} \text{ (note: } B_{ijt} \text{ is symmetric in } i \text{ and } j.)$$

$$c_{ij} = \sum_{s=1}^{t} x_t b_{it}$$

Then, in vector notation, interpreting $c_t$ as the vector with elements $(c_{1t}, c_{2t}, \ldots, c_{pt})$, $\theta$ as $(\theta_1, \theta_2, \ldots, \theta_p)$, and $B_t$ as the matrix with $B_{ijt}$ as the element at row i and column j, the expression for $\hat{\theta}$ becomes $$[c_R - c_L]^T = \hat{\theta}^T [B_R - B_L]^T$$

$$[c_R - c_L] = [B_R - B_L]\hat{\theta}$$

$$\hat{\theta} = [B_R - B_L]^{-1}[c_R - c_L]$$

We can now calculate $\sigma$ on that domain to be used in the CPIC calculation. The sum of squared errors is $$\hat{\sigma}^2 = \frac{1}{R - L + 1} \sum_{t=L}^{R} \left[ x_t - \sum_{i=1}^{p} \hat{\theta}_i b_{it} \right]^2.$$

Expanding the squared term, $$\hat{\sigma}^2 = \frac{1}{R - L + 1} \sum_{t=L}^{R} \left[ x_t^2 - 2\sum_{i=1}^{p} \hat{\theta}_i x_t b_{it} + \sum_{i,j=1}^{p} \hat{\theta}_i b_{it} b_{jt} \hat{\theta}_j \right].$$

Plugging in our expression for $\hat{\theta}_i$, $$\hat{\sigma}^2 = \frac{1}{R - L + 1} \left[ \sum_{t=L}^{R} x_t^2 - 2\sum_{i,j=1}^{p} [B_R - B_L]_{ij}^{-1} [c_R - c_L]_j \sum_{t=L}^{R} x_t b_{it} + \right.$$

$$\left. \sum_{i,j,k,l=1}^{p} [B_R - B_L]_{ik}^{-1} [c_R - c_L]_k \left( \sum_{t=L}^{R} b_{it} b_{jt} \right) [B_R - B_L]_{jl}^{-1} [c_R - c_L]_l \right].$$

Defining one more cumulate $X_t^2 = \sum_{s=1}^{t} x_t^2$ and plugging in this as well as other cumulate expressions, $$\hat{\sigma}^2 = \frac{1}{R - L + 1} \left[ X_R^2 - X_L^2 - 2\sum_{i,j=1}^{p} [B_R - B_L]_{ij}^{-1} [c_R - c_L]_j [c_R - c_L]_i + \right.$$

$$\left. \sum_{i,j,k,l=1}^{p} [B_R - B_L]_{ik}^{-1} [c_R - c_L]_k [B_R - B_L]_{ij} [B_R - B_L]_{jl}^{-1} [c_R - c_L]_l \right].$$

$$\hat{\sigma}^2 = \frac{1}{R - L + 1} \left[ X_R^2 - X_L^2 - 2\sum_{i,j=1}^{p} [B_R - B_L]_{ij}^{-1} [c_R - c_L]_j [c_R - c_L]_i + \right.$$

$$\left. \sum_{i,j=1}^{p} [B_R - B_L]_{ik}^{-1} [c_R - c_L]_j [c_R - c_L]_i \right].$$

$$\hat{\sigma}^2 = \frac{1}{R - L + 1} \left[ X_R^2 - X_L^2 - 2\sum_{i,j=1}^{p} [c_R - c_L]_i + [B_R - B_L]_{ij}^{-1} [c_R - c_L]_j \right]$$

Or, in vector notation, $$\hat{\sigma}^2 = \frac{1}{R - L + 1} \left[ X_R^2 - X_L^2 - [c_R - c_L][B_R - B_L]^{-1}[c_R - c_L] \right]$$

At every possible division point we invert a unique matrix, but these matrices are small, and with a reasonably small number of basis functions applying this algorithm is not too slow. For the variable-voltage data, we used the five largest principal components of the periodic ionic current signal, as described above.

As discussed above, application of the Change Point Information Criterion (CPIC) is an example of an over-fitting bias removal technique that can be used. In other embodiments, other over-fitting bias removal techniques may be used, including but not limited to an Aikaike Information Criterion.

Returning to FIG. 4, at block 406, the computing system performs capacitance compensation on the raw current signal for each state to create an ionic current-vs-voltage curve for each state. The bilayer separating the cis and trans wells acts as a capacitor. When operating the nanopore sequencer at constant voltage, the capacitor's presence in the circuit is unimportant. However, when operating using a time-varying voltage, the capacitor introduces an additional charging and discharging ionic current $I_{cap}$ which should be removed from the signal $I_{sig}$ we wish to observe. Thus, rather than directly reading out the sequence-dependent ionic current signal, the observed ionic current $I_{obs}$ takes the form $I_{obs} = I_{sig} + I_{cap}$.

$I_{cap}$ depends on both the size of the capacitor formed by the bilayer (a constant value over the course of the experiment) and the size of the resistor formed by the pore and the translocating DNA (which varies as a function of the sequence present within the pore). Because the resistance is different at each ionic current state, capacitance compensation is conducted separately for each ionic current state.

As $I_{cap}$ is proportional to the rate of change of the voltage $$\frac{dV}{dt},$$

our triangle wave applied voltage causes an in-phase square wave capacitive current, plus decaying exponential contributions around the ill-defined regions of $$\frac{dV}{dt}$$

when the voltage transitions from up-slope to down-slope and back. The goal of our capacitance compensation procedure is to infer the $I_{cap}$ from the asymmetry between the current values during the up-slope and down-slope voltage ramps, then subtract out this inferred signal to reveal $I_{sig}$.

Figure 15:
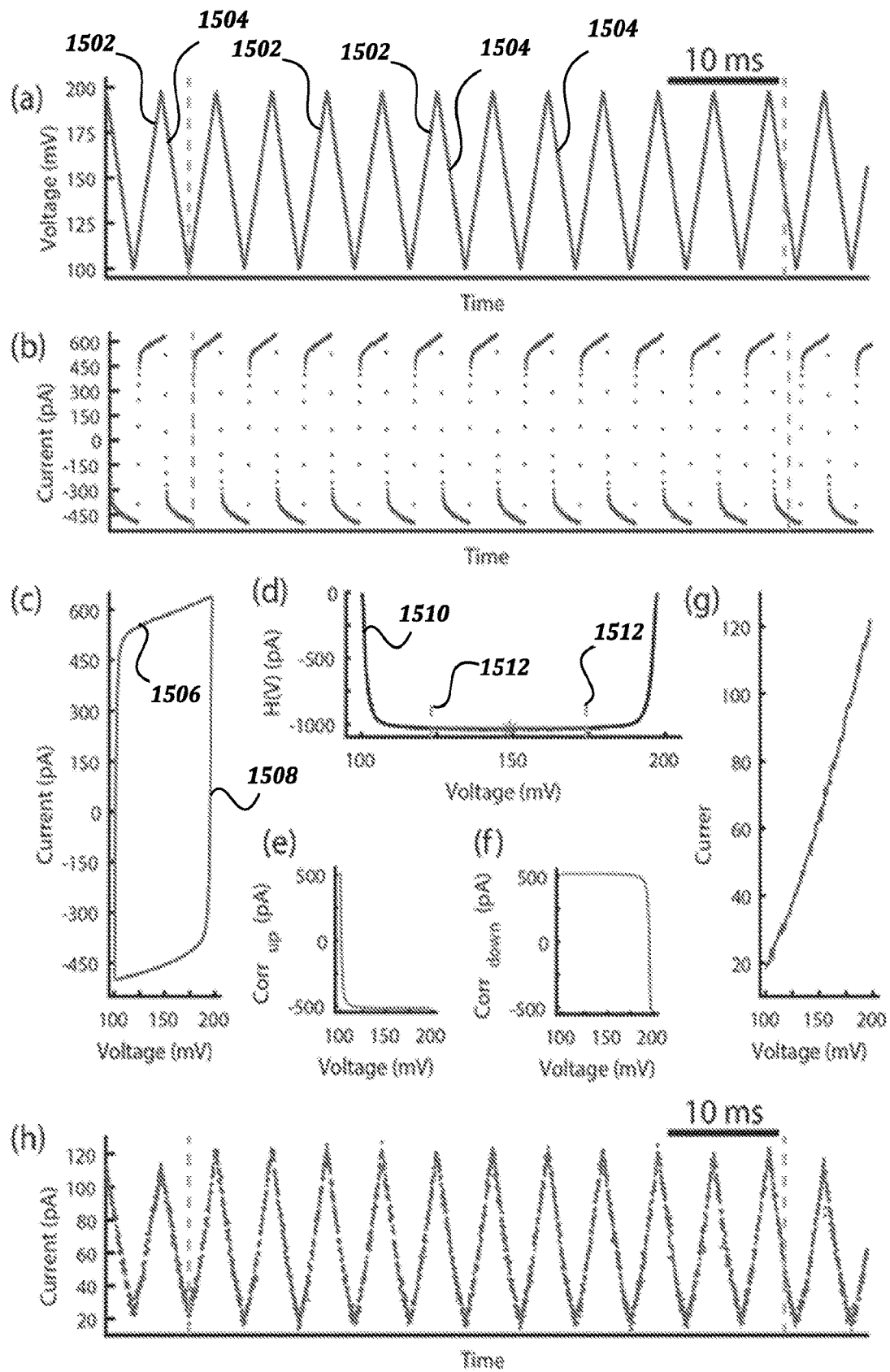
FIG. 15 includes multiple charts that illustrate various non-limiting aspects of the capacitance compensation procedure.

An example procedure for capacitance compensation is as follows. FIG. 15 includes multiple charts that illustrate various non-limiting aspects of the capacitance compensation procedure, as discussed in further detail below.

1. The overall phase of the signal is calculated from the applied voltage signal for the entire read. Knowing the overall phase, along with the number of data points collected per voltage cycle (50 kHz sampling rate, with the voltage cycling at 200 Hz gives 250 points per cycle) allows us to assign an identification index between 1 and 250 to each point in the ionic current trace I(t) marking its phase.
2. For each ionic current state, all data points in the ionic current trace I(t) are grouped by their previously determined identification index, thus binning together all data points collected at the same location in the voltage sweep. For each ionic current state, the ionic current trace I(t) is divided into "up-slope" and "down-slope" based on the identification index previously determined. Chart (a) in FIG. 15 illustrates a voltage time series for a single variable-voltage ion current state. Examples of points at which the voltage is increasing are marked as element 1502, and examples of points at which the voltage is decreasing are marked as element 1504. Dashed vertical lines mark the beginning and end of the ionic current state. Chart (b) in FIG. 15 illustrates raw ionic current time series for the single ionic current state in chart (a), and are aligned vertically in time with the corresponding points in chart (a).

3. For both the up-slope and down-slope data, we group and average all data points with the same identification index, thus finding the average ionic current value at each location in the voltage cycle. This yields the average current-voltage (I-V) characteristic for both up and down: $I_{up}$ (V) and $I_{down}$ (V) Chart (c) in FIG. 15 illustrates a raw ionic current vs. voltage curve for the ionic current state illustrated in charts (a) and (b). Individual cycles have been averaged together. Element 1506 shows the average up-slope curve, element 1508 shows the average down-slope curve.

4. Taking the difference between the two I-V curves, we get the asymmetry between the sweeps, $H(V)=I_{down}(V)-I_{up}(V)$ Chart (d) in FIG. 15 illustrates a residual function H(V) for the above ionic current state. Element 1510 shows the residual as a function of voltage. Dashed lines 1512 mark the first and third quartiles in the voltage over which the quadratic fit is calculated. The portion of Element 1510 between the dashed lines 1512 shows the quadratic fit to these data. The asterisk marks the calculated vertex.

5. To find the magnitude of the square wave component in the capacitive signal, which appears as a systematic offset m between the up and down I-V curves, we fit a parabola to the residual, H(V), over the second and third quartiles in the voltage (125 to 175 mV). The x-coordinate of the parabola's vertex is constrained to occur at the voltage midpoint (150 mV), and the y-coordinate is taken as the systematic offset m. Low and high voltages are omitted in order to isolate the offset, without interference from the sharp spikes appearing near the voltage turnaround points. A parabolic fit is used in lieu of a mean, as H(V) exhibits some curvature even over the middle voltage quartiles due to the decaying exponential current spikes generated at the voltage turnaround points. 6. Capacitive correction functions for up and down ($Corr_{up}$ (V) and $Corr_{down}$ (V)) are generated from the left and right halves of the residual function H(V) Charts (e) and (f) of FIG. 15 illustrate calculated correction functions to be added in to the up-slope (e) and down-slope (f) I-V curves, respectively. The residual function is split around the midpoint voltage of the sweep $V_{mid}$, and the correction functions are given by:

For $V<V_{mid}$, $$Corr_{up}(V) = H(V) - \frac{m}{2}$$

$$Corr_{down}(V) = -\frac{m}{2}$$

And for $V>V_{mid}$ $$Corr_{up}(V) = \frac{m}{2}$$

$$Corr_{down}(V) = \frac{m}{2} - H(V)$$

Splitting the correction in this way attributes the spike at low voltage to the up-sweep and the spike at high voltage to the down-sweep. The overall offset m is attributed equally to both sweep directions. This assignment is justified, as the capacitive effect of an instantaneous change in V(t) falls off exponentially, with time constant RC. As the low voltage turnaround immediately precedes the up-slope region, the effect of this turnaround is strong in the up-slope, but negligible by the down slope. The opposite is true for the high voltage turnaround. The overall offset is the manifestation of the square wave current generated by the constant $$\frac{dV}{dt}$$

throughout the rest of the triangle wave, and so appears equally in both up-slope and down-slope curves.

7. Applying the up and down correction functions to their respective I-V curves gives the corrected curves $I_{up}^{cc}$ and $I_{down}^{cc}$:

$$I_{up}^{cc} = I_{up}(V) + Corr_{up}(V)$$

$$I_{down}^{cc} = I_{down}(V) + Corr_{down}(V)$$

8. The corrected curves show no residual hysteresis, and the spikes around the turnarounds have been eliminated. Chart (g) in FIG. 15 illustrates corrected up-slope and down-slope I-V curves. Dashed lines are used as both curves lie directly on top of one another after the capacitance compensation has removed all hysteresis.

9. Lastly, the correction is applied to all I(t), at each point according to the identification index previously determined. This yields the capacitance compensated I(t) trace that will be used in all further analysis. Chart (h) in FIG. 15 illustrates a corrected current time series for the above ionic current state, aligned vertically with charts (a) and (b) in time.

Returning to FIG. 4, at block 408, the computing system converts the ionic current-vs-voltage curves to conductance-vs-voltage curves and performs conductance normalization. Following change point detection (block 404) and capacitance compensation (block 408), the sequencing data is in the form of a series of time-ordered ionic current-vs-voltage (I-V) curves. These I-V curves are converted to conductance-vs-voltage (G-V) curves by dividing out the voltage from the ionic current. Going forward from here, variable-voltage sequencing analysis is conducted using conductance in lieu of voltage.

Following capacitance compensation (block 408), the response to the changing voltage in the variable-voltage signal retains a nuisance component in addition to the DNA-position-dependent portion of the signal (which is the signal we are ultimately interested in for sequencing). This complicating component, dominated by the intrinsically non-ohmic character of the pore conductance when blockaded by a charged molecule, is mostly additive with the DNA-dependent portion of the signal, but is not itself affected by DNA position. It is desirable to remove this portion of the signal in order to arrive at the purely DNA-position-dependent conductance signal that changes smoothly as a function of DNA position. We refer to the process of removing the non-position-dependent portion of the conductance as "normalization" and refer to the final smooth conductance profile as the "normalized" conductance.

To find the normalized conductance curve $g_i(V)$ of a state i, we take an average of the conductance at each voltage $g_j(V)$ over each state in a read ($j \in 1: N$ where N is the number of states), and subtract this mean conductance from the measured conductance from each state:

$$\vartheta_i(V) = g_i(V) - \frac{1}{N}\sum_{j=1}^{N} g_j(V)$$

In effect, this process estimates the position-independent contribution to each state's conductance curve as the portion of the curve found on average in all of the states, then removes this shared component.

Following this simple normalization, we require a further correction to fully realize the continuous conductance profile. We observe a "fraying" of the segments in the continuous curve. That is, at high voltage, states with normalized conductances well above the mean tend to exaggerated and take higher values than what is necessary for the curve to be continuous. Likewise, states with conductances below the mean take values lower than would be expected for the continuous curve. We attribute this effect to the stretching of the DNA at high voltages. The additional elongation of the DNA at higher voltage means that fewer bases on average will contribute to the instantaneous conductance through the pore, as fewer bases spend time near the constriction. So, the DNA-dependent signal is dominated further by a few bases at high voltage than low voltage. This effect serves to exaggerate the peaks and troughs in the normalized signal.

To correct for this effect, we note that there should be no correlation between the applied voltage and the DNA-dependent conductance. Therefore, we correct to the first order by fitting a linear model to each reduced conductance curve, obtaining from each $g_i$ a slope $m_i$. These slopes are then linearly fit to the voltage means of the normalized conductances, $$\langle g_i \rangle = \frac{1}{N_V}\sum_{j=1}^{N_V} g_i(V_j)$$

where $N_V$ is the number of voltages measured in each state (=101). This fit with slope $\alpha$ represents the magnitude of the linear voltage response as a function of conductance. Subtracting this bias, we obtain the final normalized conductance which represents the DNA-dependent signal that will ultimately be used:

$$\vartheta_i(V) = g_i(V) - \frac{1}{N}\sum_{j=1}^{N} g_j(V) - \alpha V\left(g_i(V) - \frac{1}{N}\sum_{j=1}^{N} g_j(V)\right)$$

Figure 18:
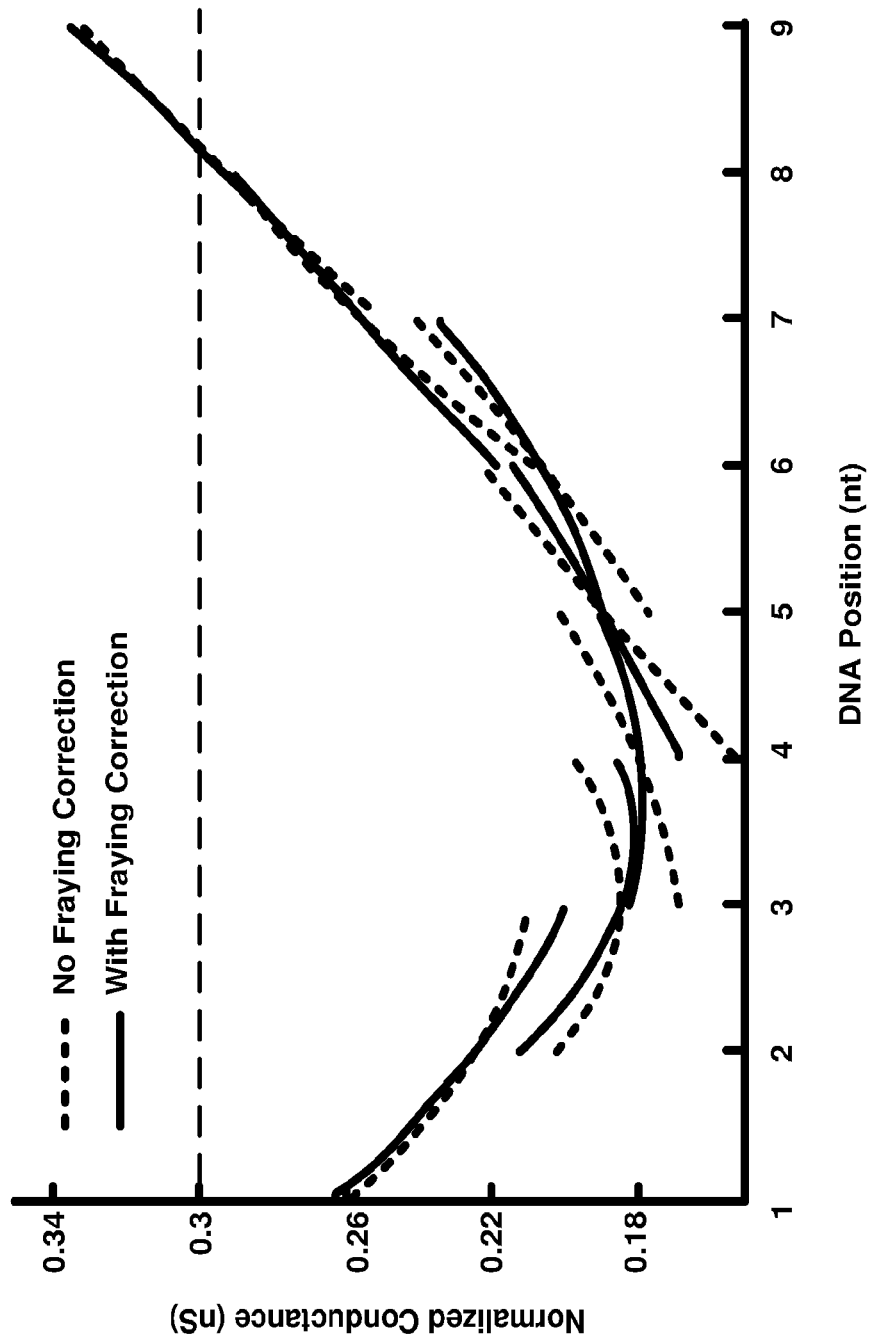
FIG. 18 is a chart that illustrates a non-limiting example embodiment of fraying correction according to various aspects of the present disclosure.

FIG. 18 is a chart that illustrates a non-limiting example embodiment of fraying correction according to various aspects of the present disclosure. The linear fray correction accounts for the exaggerated effects of a few bases on the conductance at high voltage. The initial mean-only normalization (dashed) demonstrates systematic discontinuities around peaks (not shown) and troughs (shown here) where the high-voltage points (left on each segment) are too high (peaks) or low (troughs). The dashed horizontal line shows the overall average conductance (for the whole read, of which only a short section is shown). The fray correction accounts for this and generates a more-continuous conductance profile (solid curves).

Returning to FIG. 4, at block 410, the computing system extracts features from the conductance-vs-voltage curves. Each G-V curve characterizes one enzyme step along the DNA, as determined during change point detection. Each G-V curve is made up of 101 conductance measurements taken at voltages between 110 and 190 mV, represented by a 101-dimensional feature (column) vector, g. The sampled voltage points are chosen so that the shift in DNA registration between each consecutive pair of points is uniform—we sample the conductance uniformly over DNA position, but non-uniformly over voltage. Uniform sampling over position ensures maximum independence between the sampled conductances.

Figure 16:
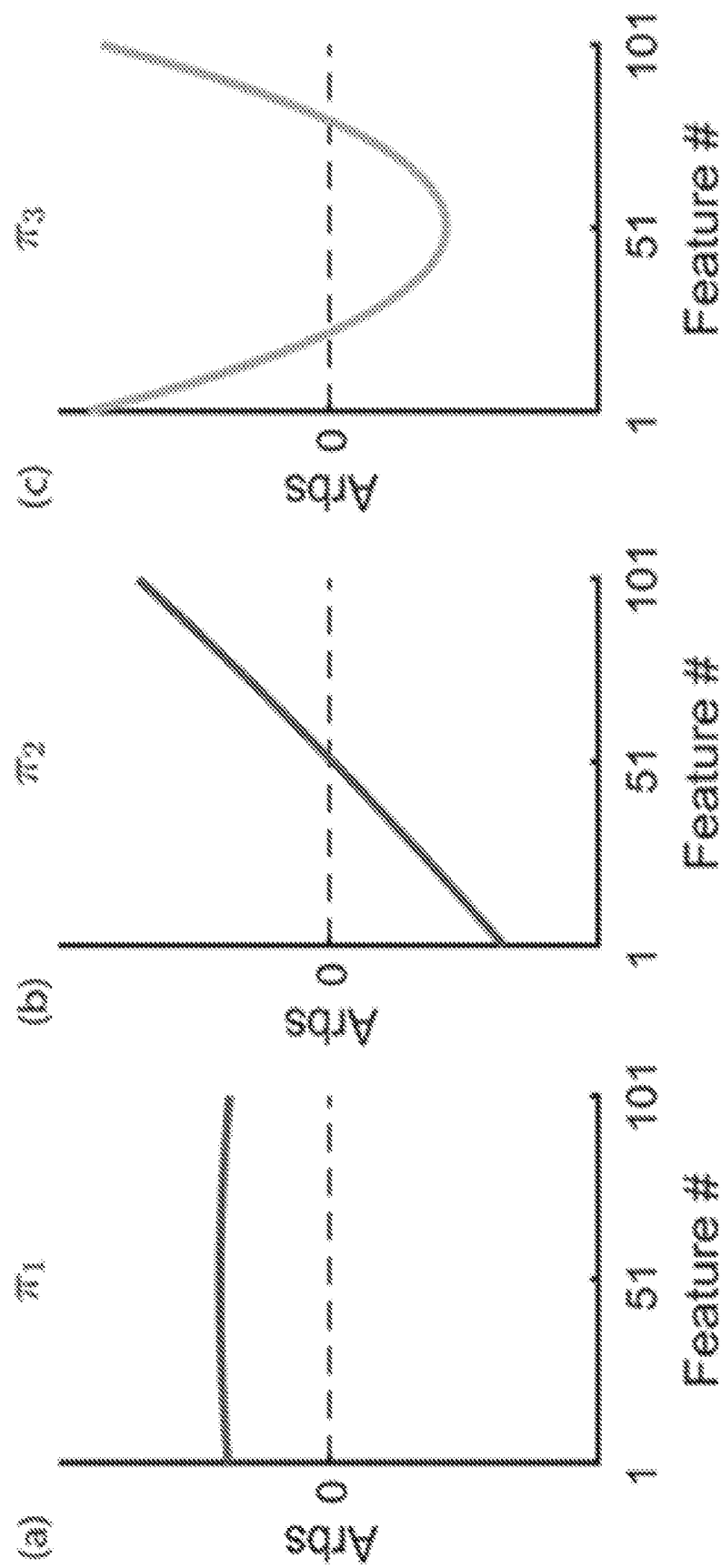
FIG. 16 includes three charts that illustrate non-limiting example embodiments of three principal component vectors for feature extraction according to various aspects of the present disclosure.

The 101 elements (features) in g are largely not independent. Many of the features provide redundant information and serve only to introduce noise into our characterization of the states. We used principal component analysis (PCA) to reduce the dimensionality of the feature vectors describing each state. PCA revealed that the top 3 principal components explain nearly 98% of the variance between G-V curves. In light of this, we reduce the dimensionality of the feature vectors from 101 to 3 by replacing the 101 sampled conductances with the coefficients of the top 3 principal components. FIG. 16 includes three charts that illustrate non-limiting example embodiments of three principal component vectors for feature extraction according to various aspects of the present disclosure. Charts (a), (b), and (c) show the first, second, and third principal component vectors for the variable voltage data, respectively. Linear combinations of these three vectors can describe all observed conductance vs. DNA position states. The three vectors roughly represent an offset (a), slope (b), and curvature (c) and thus primarily describe the states as quadratic curves.

Figure 17:
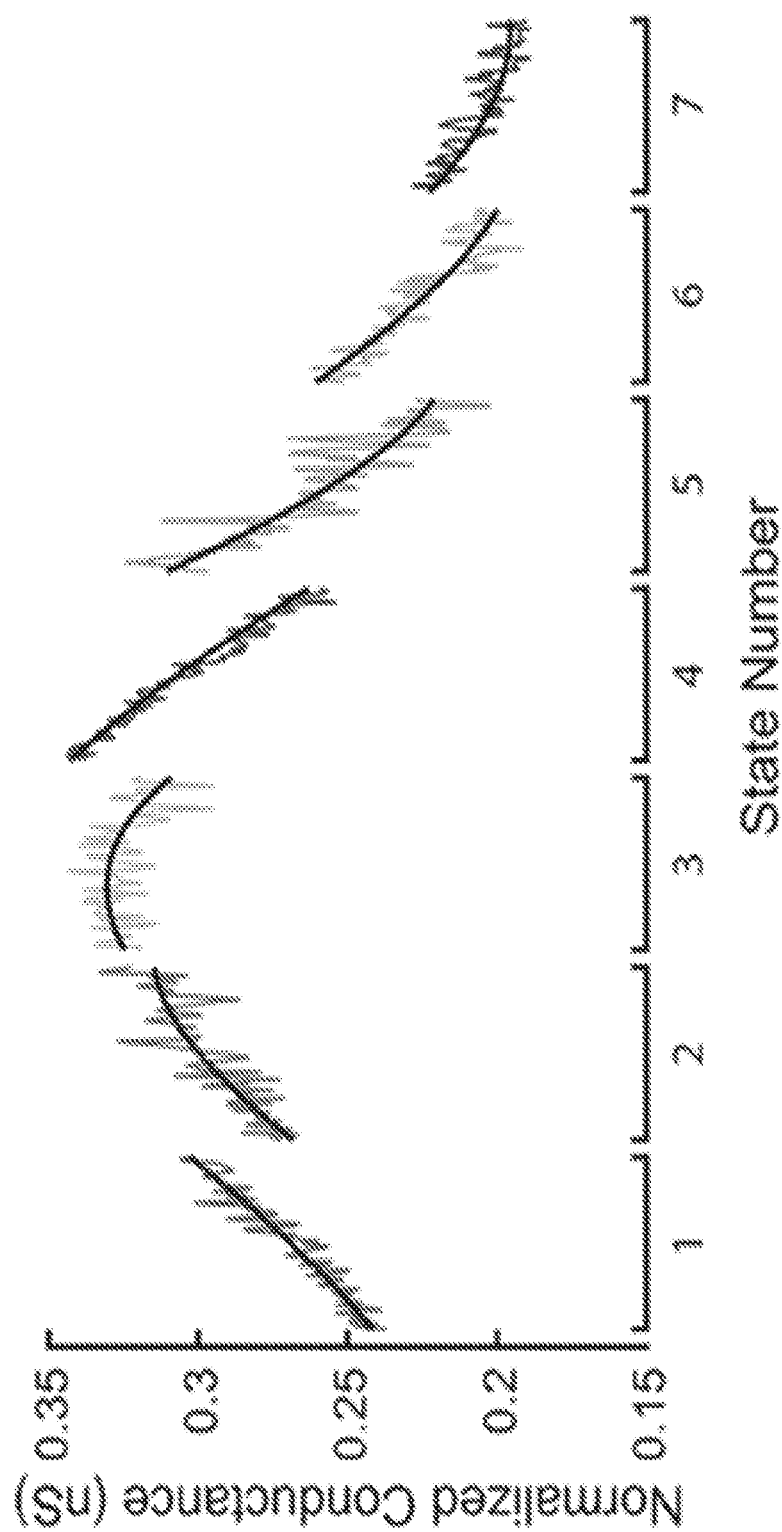
FIG. 17 is a chart that illustrates a non-limiting example embodiment of a principal component description of conductance states according to various aspects of the present disclosure.

We calculate the reduced 3-dimensional feature vector $p_i$ for state i as $$p_i = [\pi_1; \pi_2; \pi_3]^T * g_i$$

where $\pi_j$ is the $j^{th}$ principal component (column) vector. This dimensional reduction allows us to satisfactorily characterize each state while dramatically de-noising our description. FIG. 17 is a chart that illustrates a non-limiting example embodiment of a principal component description of conductance states according to various aspects of the present disclosure. Linear combinations of the 3 principal components (smooth curves) satisfactorily describe the 101-dimensional conductance states (jagged curves). The description preserves the state shape while discarding parameters describing only noise.

Additionally, we are much better able to estimate the covariance amongst the features for these smaller feature vectors. Each full voltage cycle j (200 Hz) completed during a given state i provides two measurements $g_i^j$ of the state's conductance feature vector $g_i$, one from the voltage up-swing, one from the voltage down-swing. Similarly, we can treat the 3 principal component coefficients for each half cycle $p_i^j$ as distinct measurements of the overall principal component feature vector $p_i$. Given t half-cycle measurements, we can estimate the covariance in the state's conductance ($\Sigma_i^g$) and principal component features ($\Sigma_i^p$) as $$E_i^g = E_{j \in 1:t}[(g_i^j - E_{j \in 1:t}[g_i^j])(g_i^j - E_{j \in 1:t}[g_i^j])^T]$$

and $$E_i^p = E_{j \in 1:t}[(p_i^j - E_{j \in 1:t}[p_i^j])(p_i^j - E_{j \in 1:t}[p_i^j])^T]$$

The estimators $\Sigma_i^{g,p}$ are only well defined if we have at least as many measurements as there are independent entries elements in the covariance matrix. As covariance matrices are symmetric, $\Sigma_i^{g,p}$ has $$\frac{d}{2} * (d-1)$$

independent entries, where d is the dimensionality of the associated g or p feature vector. So, in order to get a good estimate of the covariance of the conductance features $g_i$ for a given state, we require 5050 half-cycle measurements, representing over 12.5 seconds spent in that state—far longer than the typical state duration. Conversely, we can estimate the covariance of the principal component features $p_i$ from just 6 half-cycle measurements, or 15 ms of data. Using the principal component dimensional reduction, we are thus able to accurately estimate the feature covariance for nearly all (>90%) of the observed states (see results portion below). For the <10% of states for which the covariance is not well estimated, we fill in the covariance with the 90th percentile largest (by value of the determinant) well-estimated covariance.

Figure 5:
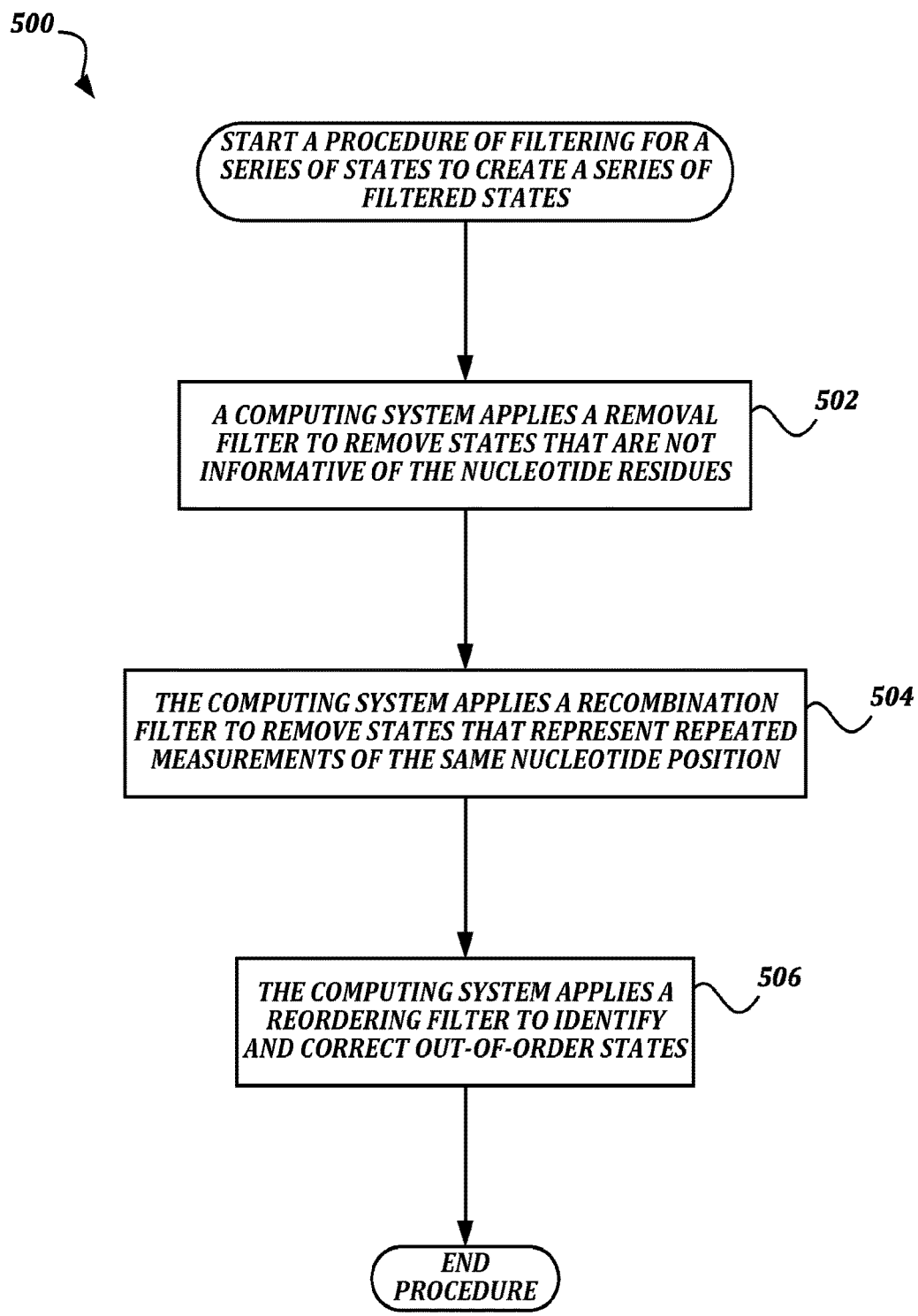
FIG. 5 is a flowchart that illustrates a non-limiting example embodiment of a procedure of filtering for a series of states to create a series of filtered states according to various aspects of the present disclosure.

Returning to FIG. 4, at procedure block 412, the computing system performs filtering for the series of states to create a series of filtered states. One of the advantages of the variable-voltage method is that it allows us to determine the correct ordering of the observed states prior to sequencing. We can determine the best ordering of observed states via a "state filtering" process prior to sequencing. Any suitable technique, or combination of techniques, may be used to filter the series of states. One example procedure for filtering states is illustrated in FIG. 5 and described in further detail below. The procedure in FIG. 5 is a three-stage filtering technique. The three stages are termed the removal filter, the recombination filter, and the reordering filter. Each stage of state filtering aims to eliminate a specific error mode common to the data, and is described in further detail in conjunction with the discussion of FIG. 5 below.

At block 414, the computing system determines the identity of one or more nucleotide residues of the nucleic acid based on the series of filtered states.

DNA sequencing is performed using a hidden Markov model (HMM) solver as described below. Simply, we decode the series of k-mers most likely to have generated the observed series of conductance states by conducting an alignment between the observed states and the 6-mer model states. In standard sequence-to-sequence (or conductance-to-conductance) alignment, the alignment proceeds from left-to-right in both sequences. In contrast, this sequencing alignment proceeds left to right in the measured states, but jumps around in the model states based on the allowed k-mer transitions. For example, AAAAAT (the 4th k-mer) can transition to AAAATG (the 15th k-mer) via a single nucleotide step, but requires a 6 nucleotide jump to reach the 5th k-mer, AAAACA. Our full adaptation and calculation of the measured-to-model alignment is described in detail below.

We first compute a score matrix S of match likelihoods $S_{nj}$ between measured state n and reference 6-mer model state j. The measured state and model state are each characterized by their d principal component amplitudes and the associated uncertainty (for measured states) or covariance (for model states) covariance matrix. The measured state is written as $x_n$ with uncertainty matrix $\Sigma_{x_n}$, and the reference state is written as $y_j$ with covariance matrix $\Sigma_{y_j}$. The match score between these states is given by $$S_{nj} = \frac{1}{\sqrt{(2\pi)^d} \frac{|\Sigma_{x_n}^{-1}||\Sigma_{y_j}^{-1}|}{|\Sigma_{x_n}^{-1} + \Sigma_{y_j}^{-1}|}} \exp\left[-\frac{1}{2}\left(\Sigma_{x_n}^{-1} x_n - \Sigma_{y_j}^{-1} y_j\right)^T \left(\Sigma_{x_n}^{-1} + \Sigma_{y_j}^{-1}\right)\left(\Sigma_{x_n}^{-1} x_n - \Sigma_{y_j}^{-1} y_j\right)\right]$$

The corresponding array of log-likelihoods is the natural logarithm of this, $$s_{nj} = \log S_{nj} = \frac{1}{2}[d \log 2\pi + \log|\Sigma_{x_n}^{-1}| + \log|\Sigma_{y_j}^{-1}| - \log|\Sigma_{x_n}^{-1} + \Sigma_{y_j}^{-1}| - (\Sigma_{x_n}^{-1} x_n - \Sigma_{y_j}^{-1} y_j)^T (\Sigma_{x_n}^{-1} + \Sigma_{y_j}^{-1})^{-1} (\Sigma_{x_n}^{-1} x_n - \Sigma_{y_j}^{-1} y_j)].$$

We use the known backstep kinetics of the enzyme, such as the known backstep kinetics of the Hel308 enzyme, to inform our sequencing. Specifically, previous work found that Hel308 is far more likely to backstep when in its ATP-independent state (the "pre" states in our 6-mer model) than when in its ATP-dependent state (the "post" states in our 6-mer model). Consequently, measured states determined to have backstepped during enzyme step correction are more likely to have been generated with ATP-independent states in our 6-mer model. To use this information, we label which measured states backstepped, then incorporate the independent/dependent state probabilities into the score matrix S as follows.

We estimate the probability that a state that backstepped was an ATP-independent state $P_{ind|b} = 0.975$ from Hel308 kinetics data. The overall probability that a state will backstep is also estimated from kinetics data as $P_b = 0.025$. From these, we can calculate the probability $P_{ind|\sim b}$ that an ATP-independent state will not backstep as $$P_{ind|\sim b} = \frac{\frac{1}{2} - P_b * P_{ind|b}}{P_{ind|\sim b}}$$

The probability that a given state is ATP-dependent given that it did ($P_{dep|b}$) or did not ($P_{dep|\sim b}$) backstep is simply 1 minus the complementary independent probability:

$$P_{dep|b} = 1 - P_{ind|b}$$

$$P_{dep|\sim b} = 1 - P_{ind|\sim b}$$

We incorporate these probabilities into the score matrix S by first converting them to log-probabilities: $p = \log(P)$. The odd-numbered columns in the score matrix ($S_{ij}$ where j is odd) represent matches to ATP-independent states and the even-numbered columns ($S_{ij}$ where j is even) are matches to ATP-dependent states. For every measured state i where we observed a backstep, we update the row $S_{i:}$ as $$S_{ij} \leftarrow S_{ij} + p_{ind|b} \text{ if } j \text{ is odd}$$

and $$S_{ij} \leftarrow S_{ij} + p_{dep|b} \text{ if } j \text{ is even}$$

Likewise, for every measured state i where we did not observe a backstep, we update the row $S_{i:}$ as $$S_{ij} \leftarrow S_{ij} + p_{ind|\neg b} \text{ if } j \text{ is odd}$$

and $$S_{ij} \leftarrow S_{ij} + p_{dep|\neg b} \text{ if } j \text{ is even}$$

This accounting tells our sequencer to preferentially call states for which a backstep was observed as ATP-independent states.

We also determine transition probabilities between each pair of states. In the case of constant-voltage sequencing, the relative probabilities of different transitions (step, skip1, skip2, . . . ) between any two given states are fixed for all states. In variable-voltage sequencing, we can use the overlap between two states' conductance curves in order to get a more informed estimate of the relative probabilities. Two states whose conductance curves overlap well are likely to be separated by a single step, whereas states whose conductance curves do not overlap are more likely to be skips. We find that we can differentiate effectively between steps and non-steps (88.9% correct calls on the labeled validation set), as well as between single skips and larger skips (79.1% correct calls on the validation set).

We use an ensemble of SVMs (similar to those described below with regard to filtering) to assign each transition its own set of probabilities of being a step, skip1, or a larger skip. The SVMs take as input the principal components of the two measured states m and n to assign probabilities to the different types of transitions between m and n. The ensemble of SVMs is made up of two classifiers ($S_1$ and $S_2$), trained on labeled examples of steps and variously sized skips from the ΦX-174 data collected during the 6-mer model construction. The scores $\mathbb{S}_i$ output by the SVMs $S_i$ are converted into probabilities using the same logit procedure as described with regard to filtering.

$S_1$ differentiates between steps and non-steps, and assigns the probability that the transition from state m to state n was a single step as $$P_{mn}^{(1)} = \text{logit}(\mathbb{S}_1, \alpha_1, \beta_1)$$

with the logit function as defined below with respect to filtering and using logit parameters $\alpha_1$ and $\beta_1$ determined from global likelihood maximization over a labeled validation set.

Similarly, $S_2$ differentiates between single skips (involving two half-nucleotide steps) and larger skips (involving more than two half-nucleotide steps). $S_2$ gives us the probability that the transition between states m and n was a single skip given that it was not a step:

$$P_{mn}^{(2|\neg 1)} = \text{logit}(\mathbb{S}_2, \alpha_2, \beta_2)$$

The overall probability then that the transition between m and n was a single skip is then $$P_{mn}^{(2)} = P_{mn}^{(2|\neg 1)} * P_{mn}^{(\neg 1)} = \text{logit}(\mathbb{S}_2, \alpha_2, \beta_2) * (1 - \text{logit}(\mathbb{S}_1, \alpha_1, \beta_1))$$

We set the probabilities of larger skips by an affine probability $P_{mn}^{(+)}$ such that $$P_{mn}^{(k)} = P_{mn}^{(k-1)} * P_{mn}^{(+)}$$

$P_{mn}^{(+)}$ is set so that the summed probability of all possible steps and skips sums to 1.

For each pair of measured states we wish to consider, we compute an 8192×8192 transition matrix T composed of the probabilities of transitioning between map states:

$$T_{mn,ij} = P\left(\begin{array}{l}\text{state } m \text{ is a measurement} \\ \text{of true map state } i\end{array} \middle| \begin{array}{l}\text{state } n \text{ is a measurement} \\ \text{of true map state } j\end{array}\right)$$

To calculate the transition matrix, we first find a matrix whose elements are the probabilities of having transitioned between states conditioned on a step size of a single half-step, $$T_{ij1} = P\left(\begin{array}{l}\text{state } t \text{ is a measurement} \\ \text{of true map state } i\end{array} \middle| \begin{array}{l}\text{state } t+1 \text{ is a measurement} \\ \text{of true map state } j\end{array}, \text{step size} = 1\right)$$

$$= \begin{cases} 1 & i \text{ is a "pre" state and } j \text{ the corresponding "post state} \\ 1/4 & i \text{ is a "post" state and } j \text{ a succeeding } 6\text{-}mer \\ 0 & \text{otherwise} \end{cases}$$

where we define two 6-mers as "successive" when they share 5 nucleotides shifted by one position, e.g. ACGTAC could be succeeded by CGTACT. We then define a similar matrix for larger sizes of step, which is calculated by taking powers of the single half-step matrix:

$$T_{ijk} = P\left(\begin{array}{l}\text{state } t \text{ is a measurement} \\ \text{of true map state } i\end{array} \middle| \begin{array}{l}\text{state } t+1 \text{ is a measurement} \\ \text{of true map state } j\end{array}, \text{step size} = k\right) = (T_{ij1}^k)$$

Finally, we define $\tau_{ij(12)}$ to correspond to all transitions with step size greater than or equal to 12, which could be between any two states. Therefore it has uniform entries $\tau_{ij(12)} = 1/8192$. Now, we can compute the total transition probability matrix as the sum of the probabilities of each possible step size by which the measured levels could have advanced:

$$T_{mn,ij} = P_{mn}^{(1)} \tau_{ij1} + \sum_{k=2}^{12} P_{mn}^{(2)} \left(P_{mn}^{(+)}\right)^{k-2} \tau_{ijk}.$$

We also define the log transition likelihood, $t_{mn,ij} = \log T_{mn,ij}$.

If we are sequencing a read of N measured states, we create an N×8192 alignment matrix, $\mathbb{A}$. In each element of the array $\mathbb{A}_{nj}$ we write an estimate of the log-likelihood that measured state n came from map state j, given the observation of measured states 1 through n−1:

$$\mathbb{A}_{1j} = s_{1j} + \log(1 - P_1^{(bad)})$$

$$\mathbb{A}_{nj} = \log \sum_{k=1}^{8192} \sum_{m=1}^{n-1} \exp\left\{ \begin{array}{l} s_{nj} + t_{mn,kj} + h_{mk} + \\ \log(1 - P_n^{(bad)}) + \sum_{l=m+1}^{n-1} \log P_l^{(bad)} \end{array} \right\}, n > 1$$

where $P_n^{(bad)}$ is the probability that observed state n is an erroneous measurement that should be omitted from the sequencer. In constant-voltage sequencing, $P^{(bad)}$ is taken as a constant value for all states. In variable-voltage sequencing, we use the same bad state classifier as in the removal filter to assign a unique $P^{(bad)}$ to each state.

This is a forwards-propagating approximation of a MAP algorithm, which in practice gives similar results to a slower forwards-backwards algorithm relying on all observations to determine likelihoods. We take two additional steps to increase speed. Firstly, using the approximation $$\log \sum_i e^{a_i} \approx \mathrm{argmax}_i a_i,$$

which is valid when one $a_i$ is significantly larger than the others. We replace the logarithms of sums of exponentials in our alignment matrix A with maxima, which are more expedient to calculate:

$$\mathbb{A}_{nj} = \max_{k,m}\left\{ \begin{array}{l} s_{nj} + t_{mn,kj} + h_{mk} + \\ \log(1 - P_n^{(bad)}) + \sum_{l=m+1}^{n-1} \log P_l^{(bad)} \end{array} \right\}, n > 1$$

We also record a traceback array, $$\mathbb{B}_{nj} = \mathrm{argmax}_{k,m}\left\{ \begin{array}{l} s_{nj} + t_{mn,kj} + h_{mk} + \\ \log(1 - P_n^{(bad)}) + \sum_{l=m+1}^{n-1} \log P_l^{(bad)} \end{array} \right\}, n > 1$$

Thus $\mathbb{B}$ nj=(m,k), such that $\mathbb{A}_{mk}$ is the maximum likelihood observed state-map state matching to have occurred just prior to the one described by likelihood $\mathbb{A}_{nj}$. This is a Viterbi technique, approximating the results of the MAP technique.

Additionally, we improve speed by restricting the max over m to only cases where m>n−q−1, where q is the maximum number of sequential "bad" observed states allowed by the algorithm. We found good results taking q=3, as cases of more than 3 consecutive "bad" states not removed by the removal filter are exceedingly rare. We also restrict the max over k to values of k such that $s_{nk} > \max_j s_{nj} - c$, where c is a score difference cut-off. Similarly, $\mathbb{A}_{nk}$ with k subject to the same restrictions is left uncalculated, because it will not be used by the algorithm under any circumstances. This avoids spending time calculating the probability flow into and out of states unlikely to represent the optimal alignment. Using c=10 provides identical results to the full calculation in all tested cases, while dramatically reducing the computational load.

Calculation of $\mathbb{A}_{nj}$ and $\mathbb{B}_{nj}$ uses knowledge of $\mathbb{A}_{(n-1)k}$ for all k, so the array is calculated starting with the n=1 elements and proceeding upwards in n.

Once $\mathbb{B}$ has been calculated, we find sequence of map states with the maximum approximate-likelihood of having produced the observed states. We do this by starting at the maximum approximate-likelihood entry in alignment matrix, at $\mathbb{A}_{n^*j^*}$, and iteratively following the traceback array through the most likely sequence of transitions. In other words, if a is the sequence of indices of true map states and n is the sequence of indices of valid observed states, $$(n_{final}, a_{final}) = \arg\max_{(n,j)} \mathbb{A}_{nj},$$

$$(n_i, a_i) = \mathbb{B}_{n_{i+1}, a_{i+1}}.$$

From a we calculate the most likely DNA sequence. Between $a_i$ and $a_{i+1}$, we find the most likely (the smallest) step size that could transition between those two 6-mers, and fill in bases accordingly. For example, GTACAC (pre) could transition to ACACTT (pre) with four half-nucleotide steps, moving the GT outside of the pore's constriction and the TT into it. It could also make the transition by taking eight half-nucleotide steps, moving the GTAC outside and the ACTT in, or by taking twelve half-nucleotide steps, moving the entire sequence GTACAC out of the constriction and the entire sequence of ACACTT in. The four-nucleotide step is the most likely based on our empirical model of transition probabilities. Therefore, if these two 6-mers were $a_i$ and $a_{i+1}$, they would be sequenced as GTACACTT, because that is more likely than the alternative choices GTACACACTT or GTACACACACTT. By performing this step for every state in a, we arrive at a close-to-optimal-likelihood sequence for the observed states.

Returning to FIG. 4, the method 400 then advances to an end block and terminates. At this point, the method 400 has determined the sequence of the analyte. This sequence may then be recorded digitally for use in downstream analysis. In some embodiments, many such sequences may be collectively stored as a sequencing run in an output file which could then be used for further analysis.

FIG. 5 is a flowchart that illustrates a non-limiting example embodiment of a procedure of filtering for a series of states to create a series of filtered states according to various aspects of the present disclosure.

From a start block, the procedure 500 advances to block 502, where a computing system applies a removal filter to remove states that are not informative of the nucleotide residues. A goal of the removal filter is to find and remove states that are not informative of the DNA sequence moving through the pore. These uninformative "bad" states are common in both constant-voltage and variable-voltage sequencing data and can arise from myriad sources. Common sources of "bad" states include:

1. Pore Gating: Protein pores such as MspA are well known to exhibit transient stochastic changes in their conductance, referred to as gating. Gating can occur during DNA translocation, resulting in an abrupt drop in the observed conductance of the observed states for the duration of the gating event. Although DNA translocation continues during the gating event, the conductance states measured in this time period will not match the ionic current-to-sequence model states of the translocating DNA due to the low overall conductance.

2. Conductance Spikes: We observe occasional transient spikes up in the conductance through the pore during DNA translocation events. These spikes may be attributable to brief openings of alternative conducting pathways through the bilayer. Regardless of origin, these spike states are not indicative of the translocating DNA sequence, and are not observed at the same DNA sequence position when comparing multiple translocation events of the same DNA sequence.
3. Flickers: As discussed above, we observe short drops in conductance within enzyme states termed "flickers" in both constant- and variable-voltage data. These drops in conductance are distinct from pore gating as they are far shorter-lived and return to the state that preceded them.
4. Over-called States: The change point detection technique occasionally calls too many transitions, partitioning a single state into multiple. This can be caused by spontaneous changes in the electronic noise, flickers occurring faster than the variable-voltage cycling frequency, or other transient effects distorting the signal. Frequently, the over-called states exhibit higher noise than the true state. These high-noise over-called states are discarded for sequencing.

The removal filter works by iteratively assigning a "bad state probability" $P_{bad}$ to each state in the event, then removing those where $P_{bad}$ exceeds some threshold value for removal $T_{remove}$. The process is iterated because $P_{bad}^i$, the bad state probability for a given state i, is a function not only of the state itself, but also of its flanking states i+1 and i−1. So, $P_{bad}^i$ can change following the first round of removal if either of its flanking states were removed. As there is no state preceding the first state or following the last state, $P_{bad}$ cannot be evaluated for these two cases. To cope with this, the first and last state are kept as "good" until the final iteration of removal, at which time they are discarded.

FIG. 27 is a pseudo-code listing that describes a non-limiting example embodiment of a removal filter according to various aspects of the present disclosure.

The $P_{bad}$ values are calculated as follows. States are first evaluated using a support vector machine (SVM) with a quadratic kernel classifying between "good" states (those to be kept for sequencing) and "bad" states (those to be removed). The SVM takes as input 12-dimensional feature vectors for each state.

The composition of the feature vector for state i is as follows:

The first 9 features serve to quantify how continuous or discontinuous the state is with its neighbors. States that are discontinuous with both the previous and subsequent states are more likely to be "bad." Accordingly, features 1-3 are the 3 principal component coefficients for the previous state, i−1, features 4-6 are the 3 principal component coefficients for the state itself, i, and features 7-9 are the 3 principal component coefficients for the subsequent state, i+1.

Feature 10 is the value of the single conductance measurement in the state's conductance curve that most deviates from the overall mean conductance in the event. This helps to identify levels with short, extreme deviations from typical conductance values. Such deviations can indicate that a noise spike occurred during the state, likely causing an over-calling during change point detection.

Feature 11 is the average mean square difference between the state's 101-dimensional measured conductance curve and its 3-dimension principal component description. This quantifies how well the state is described by the principal components. States poorly described by the principal components are more likely to be "bad."

Feature 12 is the score of these state's best match against the 6-mer model. States that do not have any high scoring match within the 6-mer model are unlikely to represent good measurements of the DNA's conductance profile and should be labeled "bad."

Figure 19:
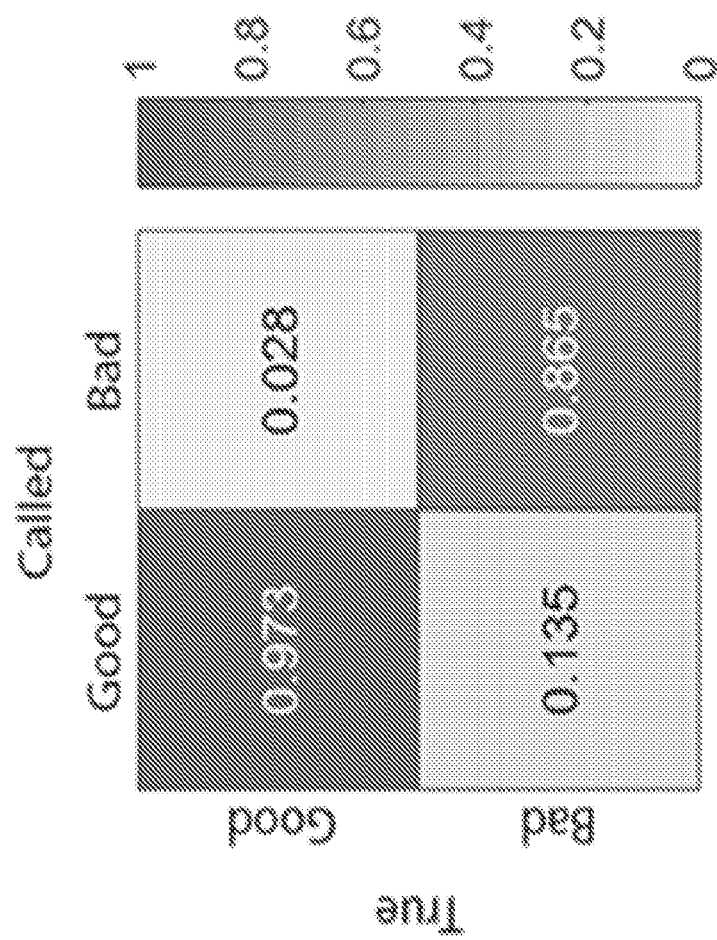
FIG. 19 illustrates the removal filter confusion matrix according to various aspects of the present disclosure.

To train the SVM, we hand-labeled states taken from the reads used for map building as either "good" or "bad." The SVM was trained on a sample of 800 labeled "good" states and 800 labeled "bad" states. We then passed a hold-out validation set consisting of 400 labeled "good" and 400 labeled "bad" states to the trained SVM. FIG. 19 illustrates the removal filter confusion matrix. Entries show the rate at which truly "good" or "bad" states are called as either "good" or "bad" by the SVM. The validation set showed that the SVM correctly classifies 97.3% of "good" states, 86.5% of "bad" states, and 91.9% of validation states overall.

To generate the "bad state" probabilities $P_{bad}$, we looked at the scores output by the SVM, rather than the labels. The SVM score S of a state is the distance of that state's SVM feature vector from the decision boundary. This score serves as a proxy for how good (negative scores) or bad (positive scores) a state is. We want to assign higher $P_{bad}$ to states with higher scores. We do this by plotting the true state labels (0 for good, 1 for bad) as a function of the state scores S. These data are then fit by the logit function $$f(S \mid \alpha, \beta) = \frac{1}{1 - e^{-(\alpha S + \beta)}}$$

using a global likelihood maximization fit.

FIG. 20 includes two charts that illustrate a non-limiting example embodiment of converting SVM outputs to $P_{bad}$ probabilities as discussed above. In the classifier illustrated in chart (a) (contrived data), points occupying the space above the decision boundary (solid black line) are classified as good while those below are classified as bad. Points marked with a "plus" are classified correctly, while "boxes" and "triangles" are classified incorrectly. Each point I has an associated score $S_i$, which is its distance from the decision boundary. In chart (b), each state in the validation set is plotted by its good (0) or bad (1) label as a function of its assigned SVM score S. The dashed black vertical line is at S=0, representing points lying exactly on the decision boundary. The solid black curve shows the logit function fit to the validation states using a global likelihood maximization procedure. The SVM scores S are converted into probabilities that the state is bad using a logit function. During removal filtering, an unknown state is assigned a score S* by the SVM. This score is then converted into a probability it is bad (P*bad) using the logit function (arrow).

Together, the SVM and the fit logit function give us a way to calculate $P_{bad}^i$ for any state i. First, the 12 features are evaluated for this state. Then, the SVM is used to score the feature vector relative to the decision boundary, yielding a score $S^i$. Finally, we evaluate $f(S^i \mid \alpha, \beta)$ yielding $P_{bad}^i$ for the state.

Returning to FIG. 5, at block 504, the computing system applies a recombination filter to remove states that represent repeated measurements of the same nucleotide position. A goal of the recombination filter is to find instances where multiple observed states represent repeated measurements of the same DNA position. Repeated state measurements can arise from two potential sources.

First, over-called transitions during change point detection result in consecutive states representing the same DNA position. If these over-called states are not removed by the removal filter, they show up in this stage as "holds". The second source of duplicate states is enzyme missteps in which the enzyme moves backwards (in the 3' direction) along the DNA. These "back steps" result in non-consecutive duplicate states.

FIG. 28 is a pseudo-code listing that describes a non-limiting example embodiment of a recombination filter according to various aspects of the present disclosure. The recombination filter works by aligning an event against itself (self-alignment). Repeated states will match to their duplicates within the event nearly as well as they match to themselves. We conduct a Needleman-Wunsch-style alignment of the states $\{x^i\}$ with themselves, $\mathbb{A}$ ($\{x^i\}, \{x^i\}$).

In this alignment, alignment of a state i to itself $\mathbb{A}$ ($x^i, x^i$) can be thought of as establishing $x^i$ as a unique, previously unobserved state. Conversely, alignment of a state i to a different (previous) state j, $\mathbb{A}$ ($x^i, x^j$), i≠j means that states i and j are repeated measurements of the same DNA position and should be recombined into a single state.

Figure 21:
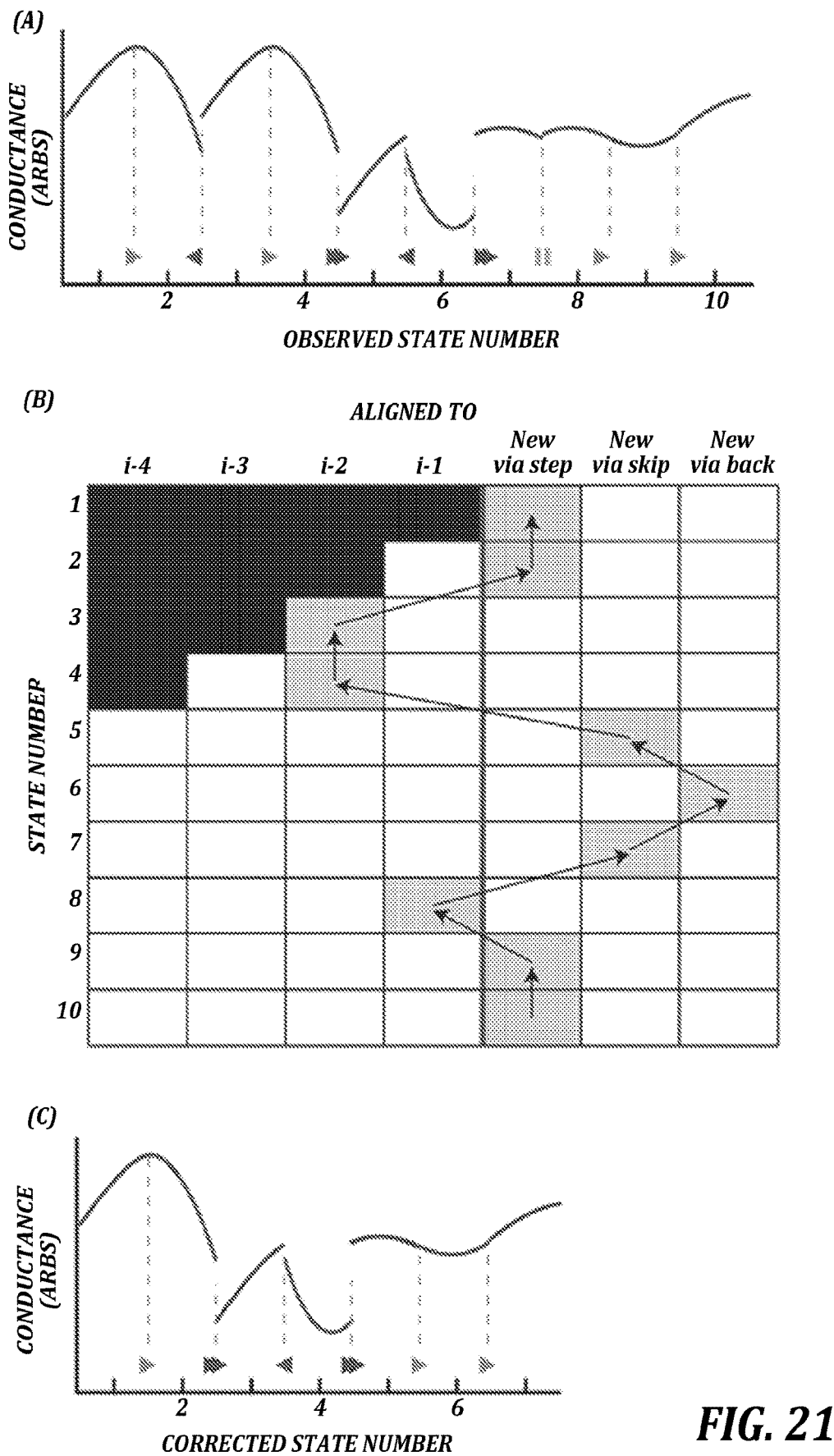
FIG. 21 includes several charts that illustrate a non-limiting example embodiment of a self-alignment procedure for a recombination filter according to various aspects of the present disclosure.

A state i will always match best with itself. However, we bias the alignment against aligning states to themselves by applying a "self-alignment penalty" $P_{SA}$ to such cells in the alignment matrix. FIG. 21 includes several charts that illustrate a non-limiting example embodiment of a self-alignment procedure for a recombination filter according to various aspects of the present disclosure. In chart (a), the recombination filter seeks to find repeated instances of the same k-mer conductance state in a sequencing read. Shown here is a toy example of a sequencing read with various missteps. Toy data is modeled on a single-nucleotide-stepping enzyme for simplicity. In chart (b), the self-alignment of the above states to themselves reveals repeated k-mer states. States 1, 2, 5, 6, 7, 9, and 10 are unique states. States 3 (=state 1), 4 (=state 2), and 8 (=state 7) are repeated measurements of previously observed states. Chart (c) illustrates that recombining the repeated measurements into single states dramatically reduces the errors in the signal. The remaining misordered states (3 and 4 should be swapped) will be treated by the reordering filter.

Statistically, the self-alignment penalty is a penalty for adding parameters (states) to our model of the observed event and the self-alignment penalty is thus taken ½ the number of added parameters (3, for the 3 principal component coefficients characterizing each state (FIG. 16)).

With these considerations, we conduct a Needleman-Wunsch-style alignment of the measured states against themselves with the following modifications. First, to reduce the computational load and avoid recombining distant states that may look similar but too far apart to represent a likely duplication, we limit ourselves to a fixed lookback distance L, where we only consider matches for state i within states i–L to i–1.

Secondly, we assign unique step-type probabilities at each transition based on the conductance curve overlap information. At each transition between two states m and n, we calculate the relative probabilities that the transition between the two occurred via a single half-nucleotide step ($P_S^{mn}$), skip ($P_K^{mn}$), backstep ($P_B^{mn}$), or hold ($P_H^{mn}$). To calculate these probabilities, we use an ensemble of 3 SVMs (quadratic kernel), $S_{SK}$, $S_{SB}$, and $S_{SH}$. These three SVMs are all trained on labeled transitions generated from the ΦX-174 data used to build the 6-mer model. In the same manner as was described above for the good/bad SVM classifier, we first trained these classifiers to determine their decision boundary, then conducted a global likelihood maximization fit to tune a logit function (characterized by two parameters, α and β) to their output scores on a held-out validation set. This fit logit function allows us to convert the output scores from the SVMs (distances from the decision boundary) into probabilities. All three SVMs take as input a 6-dimensional feature vector composed of the 3 principal component coefficients of state m and from state n.

$S_{SK}$ differentiates between steps and skips (88.7% correct on the validation set), $S_{SB}$ differentiates between steps and backsteps (98.2% correct on the validation set), and $S_{SH}$ differentiates between steps and holds (95.4% correct on the validation set). The scores of these SVMs ($\mathbb{S}_{SX}$, X one of K, B, H), converted to probabilities through their associated logit functions, give us relative likelihoods between the different step types. The relative likelihoods of a step vs. a skip between states m and n is given by $$\frac{P_S^{mn}}{P_K^{mn}} = \frac{\text{logit}(\mathbb{S}_{SK}, \alpha_{SK}, \beta_{SK})}{1 - \text{logit}(\mathbb{S}_{SK}, \alpha_{SK}, \beta_{SK})}$$

with similar relations for step vs. back and step vs. hold. These three relations, along with the overall normalization condition that $$P_S^{mn} + P_B^{mn} + P_H^{mn} + P_K^{mn} = 1$$

give us a system of four equations for the four unknowns, allowing us to solve for the various step type probabilities. Skips longer than two half-steps and backsteps longer than a single half-step backwards are treated as independent processes, with their probability given as the product of the correct number of $P_K$'s or $P_B$'s. For example, the probability of a backstep of 3 half-steps $P_{B3}$ is given as $$P_{B3} = P_B^3$$

In the language of affine probabilities, the extension probability is set to be equal to the basic probability, $$P_{B+} = P_B$$

We can enter a previously unmeasured (new) state through one of three transitions: a step, a skip, or a backstep. Consequently, our alignment matrix has dimensions N×(L+3) where N is the number of measured states. The columns 1:L represent alignment of a state to the state L:1 states before it. The final 3 columns represent the creation of a new state via alignment of the state to itself, entered into via a step, skip, or backstep, respectively.

The final modification made in our self-alignment method is the above-discussed assessment of an additional self-alignment penalty $P_{SA} = -3/2$ to these newly created states. FIG. 22 is a chart that illustrates a non-limiting example embodiment of a full matrix of transition penalties (penalties taken as log probabilities, $S = \log(P_S)$, etc.) according to various aspects of the present disclosure. During self-alignment, the transition from a starting point in the alignment (rows) into a final point in the alignment matrix (columns) takes an additive penalty. Alignments of a state to a previously measured state take a penalty equal to the log probability of the enzyme step required to generate the states in that order. Alignments of a state to itself take a step-type penalty as well as the self-alignment penalty PSA. Certain transitions (marked --) are not allowed. Using this self-alignment method to identify repeated states, we conduct recombination filtering as described in FIG. 29.

Returning to FIG. 5, at block 506, the computing system applies a reordering filter to identify and correct out-of-order states. Some enzyme misstep errors can persist in the signal even after removal and recombination filtering. Particularly, complex error modes involving successive enzyme missteps (e.g. a skip, then backstep, then skip as in FIG. 21, chart (c))

can result in out-of-order states even after bad states are removed and duplicate states are recombined. The reordering filter—the last of the three filters involved in the state filtering process—aims to identify and correct these out-of-order states prior to sequencing.

The reordering filter works by using by using an ensemble of SVMs with associated logit functions (as in the recombination filter) to assign a probability that each transition was a single step ("S"), a skip ("K"), or a backstep ("B"). A dynamic programming technique is then used to find the most likely set of allowed transitions linking the observed states.

The calculation of step-type probabilities for the reordering filter uses the same SVMs and logits as the recombination filter. The only change here is we are no longer looking for holds (holds by definition result in duplicate states, and so should be entirely treated by the recombination filter) so we only use two of the three SVMs: $S_{SK}$ to decide between steps and skips, and $S_{SB}$ to decide between steps and backsteps. Using the same procedure as in the recombination filter, we use these two SVMs to calculate the probability that each state-to-state transition represents a step, skip, or backstep. In our notation, the $n^{th}$ transition, from state n to state n+1 has a step probability $P_S^n$, skip probability $P_K^n$, and backstep probability $P_B^n$. For a read of N states, the step-type probabilities are summarized in the N−1×3 matrix $\mathcal{P}$:

$$\mathcal{P} = \begin{bmatrix} P_S^1 & P_K^1 & P_B^1 \\ P_S^2 & P_K^2 & P_B^2 \\ \cdots & \cdots & \cdots \\ P_S^{N-1} & P_K^{N-1} & P_B^{N-1} \end{bmatrix}$$

For convenience, we convert these probabilities to log-probabilities (denoted $\mathbb{P}$) for further use:

$$\mathbb{P} = \log(\mathcal{P})$$

Now with the step-type log-probabilities calculated, we use a dynamic programming technique to find the most likely path of transitions through the states, subject to certain constraints. Namely, we must choose a set of transitions reflective of a state ordering not requiring any repeated visits to the same state. For example, we cannot choose to take a step from state 1 to 2, then a backstep from 2 to 3. This hypothetical path would imply that state 3 is a repeated measurement of state 1. If this were the case, these states would have been recombined during the previous filtering step. As they were not recombined, this transition pathway must be ruled out, and is not allowed during reordering. To implement this "no repeated states" condition, we consider 4 "transition states": steps (S), backsteps (B), skips where the previous transition was a step or a skip (K|SK), and skips where the previous transition was a backstep (K|B). The allowed linkages between these transition states are summarized as an allowed linkage matrix $\mathbb{L}$:

$$\mathbb{L} = \begin{bmatrix} 1 & 0 & 1 & 0 \\ 0 & 0 & 0 & 1 \\ 1 & 1 & 1 & 0 \\ 1 & 0 & 1 & 0 \end{bmatrix}$$

where a linkage from transition state i to transition state j is allowed if $\mathbb{L}_{ij}=1$ and is not allowed if $\mathbb{L}_{ij}=0$. The 1st row and column in represents the step "transition state" S, the 2nd represents B, the 3rd represents K|SK, and the 4th represents K|B. So, for example $\mathbb{L}_{1,2}=0$ tells us that we cannot jump from a step into a backstep (as discussed above). Subject to these allowed transitions, we compute an alignment matrix $\mathbb{A}$ and traceback matrix $\mathbb{B}$ that provide us the most likely pathway through the allowed transitions. This pathway tells us what type of step was most likely taken at each transition. With this step-type information, we can optimally reorder the observed states to finally reconstruct the most likely sequence order, completing the filtering process. FIG. 29 is a pseudo-code listing that describes a non-limiting example embodiment of a reordering filter that uses a dynamic programming technique according to various aspects of the present disclosure.

Returning to FIG. 5, from block 506, the procedure 500 advances to an end block and terminates, returning the series of filtered states to a requester.

Experiments

In this work, we show how replacing the constant bias voltage with a time-varying voltage substantially reduces the impact of both error modes in nanopore sequencing. In our sequencing experiments, we use the nanopore *Mycobacterium smegmatis* porin A (MspA), which has a single narrow constriction region ideally suited to resolve nucleotide-long enzyme steps along single-stranded DNA (Butler, T. Z., Pavlenok, M., Derrington, I. M., Niederweis, M. & Gundlach, J. H. Single-molecule DNA detection with an engineered MspA protein nanopore. *Proc. Natl. Acad. Sci.* 105, 20647-20652 (2008); Manrao, E. A., Derrington, I. M., Pavlenok, M., Niederweis, M. & Gundlach, J. H. Nucleotide Discrimination with DNA Immobilized in the MspA Nanopore. *PLOS ONE* 6, e25723 (2011)) (ssDNA). We use the Hel308 DNA helicase enzyme from *Thermococcus gammatolerans* EJ3 (hereafter referred to as Hel308) as the motor enzyme to control DNA translocation through the pore. Hel308 has been observed to take two steps per nucleotide as it translocates along ssDNA, with each step approximately a half nucleotide in length (Derrington, I. M. et al. Subangstrom single-molecule measurements of motor proteins using a nanopore. *Nat. Biotechnol.* 33, 1073-1075 (2015)). These half-nucleotide steps provide two conductance measurements per nucleotide (FIG. 1, chart (c)).

Positive voltage applied across the nanopore generates a force on the DNA threaded through the pore. Varying the magnitude of this voltage changes the force pulling on the DNA. The force stretches the section of DNA between the DNA-binding sites within Hel308 and the high field region at the nanopore's constriction (Derrington, I. M. et al. Subangstrom single-molecule measurements of motor proteins using a nanopore. *Nat. Biotechnol.* 33, 1073-1075 (2015)). Increasing the applied voltage elongates the DNA and shifts the relative position of the DNA in the constriction (FIG. 1, chart (d)). A voltage change from 100 mV to 200 mV repositions the DNA in the pore by slightly more than a full nucleotide (FIG. 1, chart (e); discussed below). Thus, the applied voltage serves as a fine control over the DNA position in the pore.

The fine DNA position control using the variable-voltage complements the discrete stepping of the motor enzyme. We combine the enzyme and voltage control methods by replacing the constant applied voltage with a 200 Hz, symmetric triangle waveform voltage from 100 to 200 mV. The positive overall bias is necessary to keep the DNA-enzyme complex held on top of the pore. The 200 Hz triangle wave frequency goes through several cycles for each Hel308 step (average rate ~20 steps/s in our sequencing conditions, discussed below). While the motor enzyme steps along the entire length of the DNA, the changing voltage repositions the DNA incrementally within each enzyme step. Together, the enzyme steps and the variable-voltage sample the effect of the DNA on the pore's conductance nearly continuously along the DNA (FIG. 1, chart (f)).

In the constant-voltage signal, the pore conductance is probed only at a single DNA position at each enzyme step. Each step is thus only characterized by a single value: the conductance at that DNA position (FIG. 2, charts (a) and (b), upper). Variable-voltage sequencing instead probes the conductance continuously over a ~1 nucleotide long range at each enzyme step, characterizing each step by a conductance vs. position curve (FIG. 2, charts (a) and (b), lower). These curve segments provide additional identifying information as to the generating DNA sequence compared to the mean conductance alone. Two sequences with nearly identical conductance values in the constant-voltage mode can be distinguished based on the shape of the curves generated by the variable-voltage (FIG. 2, chart (a), oval highlights).

The variable-voltage signal also provides information about the correct ordering of the measured enzyme steps and can be used to infer the existence of steps too fast to observe. The ability to identify enzyme missteps is enabled by the variable-voltage technique's continuous sampling of the conductance through the pore as a function of DNA position. In variable-voltage sequencing, at each consecutive Hel308 half-nucleotide step, the full-nucleotide stretch caused by the voltage sweep samples the conductance at many of the same DNA positions as the previous and next Hel308 steps. Therefore, each measured segment of the conductance vs. position curve will be overlapping and continuous with the segments measured at adjacent Hel308 steps. If two consecutively measured segments are not overlapping and continuous, a non-uniform step such as a backstep or skip must have occurred. The degree of overlap between consecutive measurements can therefore be used to identify and correct enzyme missteps (FIG. 2, charts (a) and (b), arrows). A probabilistic support vector machine informed by the shapes of the curves immediately preceding and following each enzyme step as discussed above can be used on the variable-voltage signal to identify and eliminate misorderings caused by enzyme missteps and reestablish the order most representative of the generating DNA sequence. The resulting corrected signal (FIG. 2, charts (c) and (d)) is free of enzyme missteps and is more easily decoded into the correct DNA sequence. Measurements of DNA positions that go completely unobserved due to enzyme skips cannot be filled in at this stage. However, the overlap information can be used to label the probable locations of enzyme skips in the final signal to be sequenced. This information tells the sequencer that one or more bases must be inserted at this location, reducing the detrimental impact of enzyme skips relative to constant-voltage nanopore sequencing.

To objectively evaluate the extent to which the variable-voltage method improves single-passage sequencing accuracy over the constant-voltage method, we tested both sequencing methods on the same target DNA sequence, using the same enzyme (Hel308) and nanopore (MspA). In both cases, we used a hidden Markov model (HMM) (discussed above) to decode the generating DNA sequence for the observed signal. For both constant- and variable-voltage sequencing, we used a model mapping each unique 6 base sequence segment (6-mer) to an associated conductance signal. We generated this model empirically by measuring the signal of known DNA sequences (ΦX-174 and lambda phage DNA, as well as synthetic oligos) using our variable-voltage sequencing conditions. For constant-voltage sequencing, we extracted a constant-voltage 6-mer model from the variable-voltage model to ensure that any systematic model errors affecting the sequencing accuracy of one method affected both methods equally.

We used the pET28a vector as the target DNA sequence because it provided a non-synthetic DNA testing ground for the two methods separate from the sequences that were used in constructing the 6-mer model. We fragmented the pET28a vector using a selection of restriction enzymes, allowing us to attach the necessary sequencing adapters and increasing the likelihood of reading sequences at all locations on the pET28a vector given the limited processivity of Hel308 (~1000 nt). The variable-voltage method does not reduce the nanopore sequencer's ability to sequence long (multiple kb) reads.

We obtained reads of the pET28a fragments using both constant-voltage (31 reads, N=9368 bases across all reads) and variable-voltage (97 reads, N=17309 bases across all reads) methods. Enzyme steps in the constant- and variable-voltage conductance signals were detected using the change-point detection technique discussed above, segmenting the data into distinct conductance states. In the variable-voltage experiments, the capacitive charging currents from the bilayer were removed from each state using the techniques discussed above. We used the overlap information between successive conductance states to identify and correct enzyme missteps in the variable-voltage reads as discussed above, then both sets of reads were calibrated and sequenced. For both the constant- and variable-voltage sequencing results, we determined the ground truth sequence for each read by aligning the called sequence to the pET28a reference sequence. Based on the alignment, we calculated the per-base sequencing accuracy as (number of matches)÷(number of matches+number of mismatches+number of insertions+number of deletions). The error in per-base sequencing accuracy is binomially distributed.

Relative to the constant-voltage reads, the variable-voltage reads have fewer base calling errors (miscalls, deletions, and insertions, as illustrated in FIG. 3, charts (a) and (b)). The average per-base accuracy in the variable-voltage reads is 79.3±0.3% (SEM) for single passages of a single-stranded DNA molecule. This represents a significant improvement over nanopore sequencing with constant-voltage where our average accuracy using the same DNA was 62.7±0.5% (SEM). Our constant-voltage sequencing accuracies are similar to single-passage, unpolished 1D reads reported with the Oxford Nanopore Technologies' MinION device (Krishnakumar, R. et al. Systematic and stochastic influences on the performance of the MinION nanopore sequencer across a range of nucleotide bias. Sci. Rep. 8, 3159 (2018); Rames, E. & Macdonald, J. Evaluation of MinION nanopore sequencing for rapid enterovirus genotyping. Virus Res. 252, 8-12 (2018)). To contextualize the relative accuracy of the two methods, we compared the distribution of observed per-read accuracies with the accuracy distribution for random sequences of the same lengths aligned against the pET28a reference sequence. The sequencing accuracies of these random sequences is about 58% (FIG. 3, charts (c) and (d)); this random base call accuracy is so high (i.e. much larger than 25%) because of the freedom provided to the alignment algorithm to call insertions, deletions or mismatches. Whereas the constant-voltage read accuracies only barely outperform the accuracies of randomly generated sequences (FIG. 3, chart (c)), the variable-voltage read accuracies are significantly higher than the distribution of random accuracies (FIG. 3, chart (d)). We conclude that, with all other variables held constant (choice of nanopore, motor enzyme, base calling algorithm), the variable-voltage reads recover significantly more information from the target DNA and, thereby, substantially increase the base calling accuracy.

Improved single-read accuracy will allow fewer reads to be assembled into a high-accuracy consensus sequence, reducing sequencing time and cost. Additionally, variable-voltage sequencing addresses systematic errors—in the form of sequence-dependent enzyme missteps (Craig, J. M. et al. Revealing dynamics of helicase translocation on single-stranded DNA using high-resolution nanopore tweezers. *Proc. Natl. Acad. Sci.* 114, 11932-11937 (2017)) and indistinguishable signals—that persist even when the information from many reads is combined. Variable-voltage reads can also be more confidently identified with only single-read coverage. This capability is necessary for nanopore sequencing applications where high coverage is not an efficient workaround, such as metagenomics studies and pathogen detection at low concentrations.

The additional information provided by the variable-voltage signal is complementary to other nanopore sequencing improvements, including more processive and predictable motor enzymes, more sophisticated base calling algorithms, reading both sense and antisense of the target DNA strand in "2D" techniques (Jain, M. et al. MinION Analysis and Reference Consortium: Phase 2 data release and analysis of R9.0 chemistry. *F1000Research* 6, 760 (2017)) (or the similar "1D squared" technique) or polishing reads with a consensus of passages of different DNA molecules (Vaser, R., Sovic, I., Nagarajan, N. & Sikic, M. Fast and accurate de novo genome assembly from long uncorrected reads. *Genome Res*. gr.214270.116 (2017). doi: 10.1101/gr.214270.116; Simpson, J. *Signal-level algorithms for MinION data. Contribute to jts/nanopolish development by creating an account on GitHub*. (2018)). Existing nanopore sequencers already consist of hundreds or thousands of parallel nanopores, which are separately addressable with distinct driving voltages. Accordingly, the variable-voltage method approaches described herein require little re-engineering of existing nanopore sequencing devices other than the application of a waveform in place of a constant voltage. Consequently, this method can be used to improve sequencing accuracy on most existing platforms. The performance of variable-voltage nanopore sequencing will further improve as larger data sets are used to train both the model that maps conductance curves to DNA bases and the enzyme misstep classifier. Incorporating the variable-voltage method into new nanopore sequencing platforms will enhance all nanopore-based DNA sequencing applications, including species identification, epigenetic mapping, and higher accuracy de novo genome sequencing at lower coverage.

Proteins

The same mutant MspA protein was used in all sequencing experiments. This mutant, M2-NNN-MspA, was custom ordered from GenScript. M2-NNN-MspA is engineered on the wild type MspA (accession number CAB56052.1) with the following mutations: D90N/D91N/D93N/D118R/E139K/D134R (Butler, T. Z., Pavlenok, M., Derrington, I. M., Niederweis, M. & Gundlach, J. H. Single-molecule DNA detection with an engineered MspA protein nanopore. *Proc. Natl. Acad. Sci.* 105, 20647-20652 (2008)). All sequencing experiments used the Hel308 helicase enzyme from *Thermococcus gammatolerans* EJ3 (accession number WP_015858487.1). Hel308 was expressed in *E. coli* using standard techniques. All proteins were stored at −20° C. until immediately before use.

DNA Sequences and Constructs

Short DNA oligonucleotides were synthesized and purified using column purification methods at Stanford University Protein and Nucleic Acid Facility. The ΦX-174 DNA (NCBI reference sequence NC 001422.1) was obtained from New England Biolabs. The lambda phage DNA (GenBank J02459.1) was obtained from Promega. The pET-28a DNA was obtained from collaborators who used it as an expression vector for another DNA sequence not used in this work. The complete DNA sequences for ΦX-174, lambda, and pET28a can be found at http://dx.doi.org/10.6084/m9.figshare.7140896.v1.

All experiments were conducted with the DNA threaded through the pore 5' end first. DNA constructs for Hel308 experiments consisted of a template read strand and a cholesterol-tagged blocking strand. A negatively charged terminal phosphate was attached to the 5' end of the template strand, increasing the capture rate of that end by MspA. The cholesterol tag at the 5' end of the blocking strand anchors the DNA constructs into the bilayer, increasing the local concentration near the pore and increasing the capture rate. Detailed description of how the various DNA sequences were prepared can be found above. A full accounting of the custom DNA sequences used in these experiments is given below.

Nanopore Experiments

All experiments were conducted as described in detail in previous work (Laszlo, A. H., Derrington, I. M. & Gundlach, J. H. MspA nanopore as a single-molecule tool: From sequencing to SPRNT. *Methods San Diego Calif.* 105, 75-89 (2016)). Briefly, experiments were established with a device made from Teflon that contains two ~50 µL chambers (cis and trans). The two chambers are connected by a Teflon heat-shrink "u-tube", ~30 µL in volume. The cis side of the u-tube narrows into a horizontal ~20 µm aperture. Both chambers and the u-tube were filled with the operating buffers. The cis chamber was connected to ground via an Ag/AgCl electrode, while the trans-side Ag/AgCl electrode was connected to an Axopatch 200B integrating patch clamp amplifier (Axon Instruments) that also supplied the positive driving voltage. A lipid bilayer was formed across the aperture using 1,2-diphytanoyl-sn-glycero-3-phosphocholine (DPhPC) or 1,2-di-O-phytanyl-sn-glycero-3-phosphocholine (DOPC), obtained from Avanti Polar Lipids.

Following bilayer formation, M2-NNN-MspA was added to the cis chamber to a final concentration of ~2.5 ng/mL. A single pore insertion into the bilayer was recognized by a characteristic increase in the conductance. Upon single pore insertion, the cis chamber buffer was perfused out and replaced with MspA-free buffer to prevent the insertion of additional pores. The Hel308 motor enzyme was added to the cis chamber to a final concentration of ~50 nM, and DNA was added to a final concentration of ~5 nM.

Hel308 is used as a translocase, rather than a helicase, in the sequencing experiments presented here, similar to previously described experiments (Derrington, I. M. et al. Subangstrom single-molecule measurements of motor proteins using a nanopore. *Nat. Biotechnol.* 33, 1073-1075 (2015)). Briefly, Hel308 loads onto the overhanging 3' end of the template DNA strand at the single-stranded/double-stranded junction. The 5' end of the template strand is captured by the pore, and the blocking strand is sheared off as the template strand is pulled through the pore. Hel308 is too large to fit through MspA, and arrests the template strand translocation once the duplexed blocking strand has been completely sheared away. Hel308 proceeds as a translocase from 3' to 5' along the template strand, incrementally pulling the DNA out of the pore towards cis.

Operating Buffers

All experiments were conducted using symmetric cis and trans buffer conditions of 400 mM KCl with 10 mM HEPES at pH 8.00±0.05. The cis buffer additionally contained 1 mM EDTA, 1 mM DTT, 10 mM $MgCl_2$, and 100 µM ATP. ATP-containing buffer was re-perfused into cis approximately once per hour to prevent depletion of ATP and accumulation of ADP. Experiments were performed at 37° C.

These buffer conditions and temperature were found to have good performance for the techniques described herein. In some embodiments, different buffer conditions may be used, such as a value for KCl in a range of 100 mM to 1000 mM, a value for HEPES in a range of 9 mM to 11 mM, a pH value in a range of 7.00±0.05 to 9.0±0.05, a value for EDTA in a range of 0.9 mM to 1.1 mM, a value for DTT in a range of 0.9 mM to 1.1 mM, a value for $MgCl_2$ in a range of 9 mM to 11 mM, and a value for ATP in a range of 10 µM to 1000 µM.

Data Acquisition and Analysis

Experiments were controlled and data were acquired with custom acquisition software written in LabView (National Instruments) at a sampling rate of 50 kHz. The ionic current signal was low pass filtered at 10 kHz in the patch clamp amplifier. Ionic current traces were analyzed using custom programs written in Matlab (the Mathworks).

Reads were filtered using a custom compression filter (flicker removal, discussed above) to eliminate transient fluctuations in ionic current unrelated to translocating DNA sequence. Enzyme-controlled DNA translocation events were detected with a thresholding technique as described in previous work (Jain, M. et al. MinION Analysis and Reference Consortium: Phase 2 data release and analysis of R9.0 chemistry. *F1000Research* 6, 760 (2017)). For constant-voltage experiments, the open pore ionic current value was determined for the data, and an event was called whenever the ionic current drops below 75% of the open pore value. The event end was called when the ionic current returns to greater than 94% of the open pore value. Events failing certain basic criteria (duration longer than 1 s, an average ionic current less than 10% or greater than 70% of the open pore value) were automatically discarded. Remaining events were classified by-eye based to select events with a large number of enzyme steps. The same thresholding method was used for event detection in the variable-voltage data, with the sole difference being that the variable-voltage data was first downsampled to 200 Hz, thus removing the periodic characteristics of the signal.

Small variations in temperature, salt concentration, and electrode offsets from day-to-day, pore-to-pore, and read-to-read cause changes in both the overall magnitude of the observed conductances (an "offset") as well as the relative magnitudes of adjacent states (a "scale"). We calibrate each read to the 6-mer model prior to sequencing using a scale and an offset calculated specifically for that read.

Elongation of DNA in MspA

We hypothesize that the observed voltage-dependent shift in DNA position relative to MspA is due primarily to the elongation of the section of ssDNA between the enzyme and the pore constriction in response to the force generated by the applied voltage. To confirm that DNA stretching is the main effect responsible for the position shift and that other effects (i.e. Brownian motion of the enzyme above MspA or deformation within the enzyme or pore under force) are less important, we compare our shift vs. voltage data to the extensible Freely Jointed Chain (ex-FJC) model of ssDNA elongation in response to force. The ex-FJC is an experimentally validated model of the elastic response of ssDNA to applied force which predicts the average end-to-end distance of the DNA (x) as a function of the force (F) applied to one end as $$x = L_c\left(\coth\left(\frac{Fb}{k_BT}\right) - \frac{k_BT}{Fb}\right)\left(1 + \frac{F}{S}\right)$$

where $L_c$ is the DNA contour length, $k_B$ is the Boltzmann constant, T is the temperature, b is the Kuhn length of ssDNA, and S is the stretching modulus of ssDNA.

In the high force regime in which we operate our variable-voltage experiments $Fb \gg k_BT$, so the coth term can be well-approximated as identically equal to 1. With this approximation, the force-extension relation simplifies to $$x = L_c\left(1 - \frac{k_BT}{Fb}\right)\left(1 + \frac{F}{S}\right)$$

The Kuhn length of ssDNA is known to depend upon salt concentration. From Bosco et al., we expect a Kuhn length of around 1.50 nm for the 400 mM KCl conditions in our variable-voltage experiments. We take a reasonable value of the stretching modulus S to be 800 pN.

Following the analysis in Derrington et al. 2015, we observe that in our system the end-to-end extension x is fixed as the distance between the constriction and the point where the DNA is anchored within the enzyme. With x fixed, it is the contour length $L_c$ that changes with applied force. Assuming that the force on the DNA is proportional to the applied voltage as $F=\alpha V$ (a some proportionality constant) gives $$x = L_c\left(1 - \frac{k_BT}{\alpha Vb}\right)\left(1 + \frac{\alpha V}{S}\right)$$

Changing the applied voltage from V to $\beta V$ will change the contour length of the DNA within the pore from $L_c$ to $\omega L_c$:

$$x = \omega L_c\left(1 - \frac{k_BT}{\beta \alpha Vb}\right)\left(1 + \frac{\beta \alpha V}{S}\right)$$

Here, the elongation ratio $\omega$ is the ratio between the contour length of DNA in the pore at the two voltages V and $\beta V$. Solving these two equations for $\omega$ gives us a model predicting the elongation ratio $\omega$ as a function of the voltage ratio $\beta$ as $$\omega_{model} = \beta\left[\frac{(b\alpha V - k_BT)(S + \alpha V)}{(b\beta \alpha V - k_BT)(S + \beta \alpha V)}\right]$$

Figure 23:
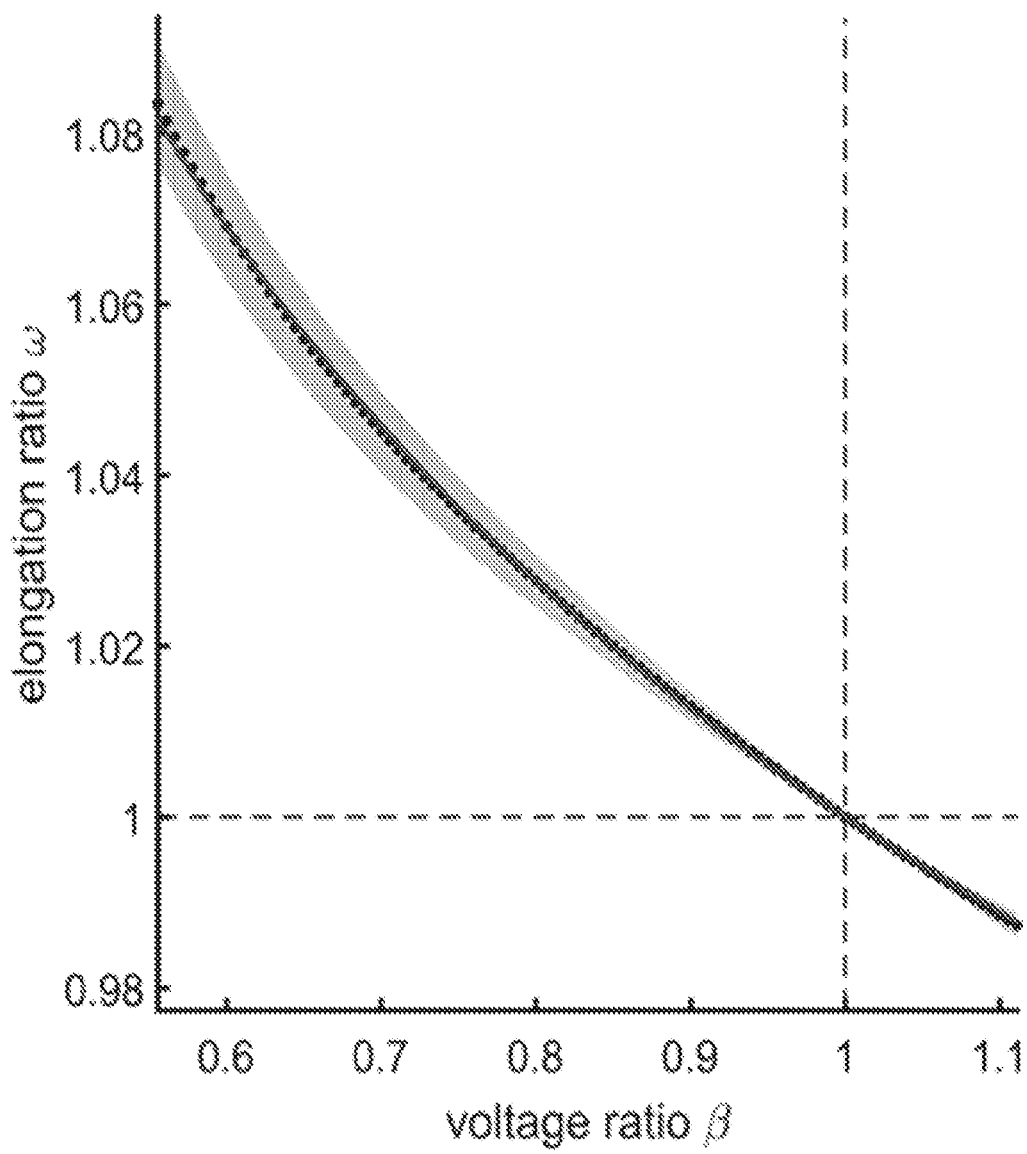
FIG. 23 is a chart that illustrates a non-limiting example embodiment of DNA stretching in MspA according to various aspects of the present disclosure.

We compare this $\omega_{model}$ to the measured elongation ratio results ($\omega_{meas}$) as a function of voltage. The measured elongation ratio is calculated from the position shift data as $$\omega_{meas}(\beta) = \frac{N_{ref} + \delta(\beta)}{N_{ref}}$$

where δ is the measured position shift from 180 mV and $N_{ref}$ is the number of nucleotides between the last hold point within the enzyme and the constriction at the reference voltage of 180 mV. FIG. 23 is a chart that illustrates a non-limiting example embodiment of DNA stretching in MspA according to various aspects of the present disclosure. The fractional DNA elongation relative to DNA position at 180 mV (ω) is plotted (points) relative to the fractional applied voltage relative to 180 mV (β). The gray shading shows the 1 standard deviation interval. The curved line shows the ex-FJC fit with α=1.47±0.8 e-nm. Position shift is calculated as described below.

From Bhattacharya et al., we estimate $N_{ref}$=12 nt. Fitting the equation above to our data shows that a single parameter fit with $$\alpha = 1.47 \pm 0.08 \frac{e^-}{nm}$$

describes me data well, as shown in FIG. 23. Uncertainties here are based on uncertainties in the DNA shift at different voltages and an assumed 0.5 nt uncertainty in $N_{ref}$. As the position shift can be well modeled by a reasonable single parameter model of DNA elongation, we are confident attributing the shift observations to this effect.

The fitted α parameter corresponds to a force of ~42 pN at 180 mV. This force estimate has larger uncertainties than the uncertainty in a as the estimate is critically dependent on the choices of ex-FJC parameters and ignores secondary effects contributing to the stretching. Potentially relevant secondary effects not accounted for by the ex-FJC model could include effects from the confinement of the ssDNA within the pore vestibule, voltage dependence of the position of the enzyme relative to MspA, and voltage-induced deformation of the enzyme or the pore.

Position Shift Calculation

The position shift calculation was done using the consensus conductance measurements for a known DNA sequence (stretching read strand, Table S3). The consensus conductances were determined from 18 separate measurements of the DNA sequence using standard variable-voltage sequence conditions (Table S4).

The position shift between two voltages $V_1$ and $V_2$ is determined as the shift that best places the conductance profile measurements from each of the two voltages along a single spline. The shift is calculated between consecutive voltages (e.g. 101 mV to 102 mV) because the conductance profile changes over large changes in voltages. As the DNA is more elongated at higher voltages, the conductance measured at each DNA position is a function of a smaller number of nucleotides. Consequently, features of the conductance profile that are blurred out at low voltages due to averaging can become apparent at higher voltages. This affect is accounted for during our normalization procedure, discussed above.

The shift best placing the conductance measurements from the two voltages along a single spline is calculated as follows. After first normalizing the conductances (described above), we have the conductance profiles for each of the two voltages, $G_1$ and $G_2$. We then calculate cubic spline interpolations ($spG_1$ and $spG_2$) to both of the transformed current profiles. The two splines are shifted left and right relative to each other in increments of $$\frac{1^{th}}{1000} nt.$$

For each shift position ϕ, we calculate a match score $\mathcal{M}$ by taking the sum-square difference between the two splines for the given shift, and dividing out by the total number of compared points:

$$\mathcal{M}(\phi) = \frac{\sum_{i=1}^{N_{pts}} (spG_1^{(i)} - spG_2^{(i+\phi)})^2}{N_{pts} - \phi}$$

The shift $\phi_0$ giving the best (smallest) match score gives us the shift that makes the two splines most similar. This $\phi_0$ is taken as the position shift between $V_1$ and $V_2$. The uncertainty δϕ was determined by measuring the shift using subsets of the entire dataset. From the longer measured sequence, we extracted 9 distinct subsets, and measured the shift function for each. We took δϕ ad the standard deviation of these separate measurements.

Hel308 Processivity

The read length in both our constant-voltage and variable-voltage sequencing experiments is limited by the processivity of the Hel308 helicase enzyme we use to control DNA motion through the pore. The enzyme's processivity is the typical number of nucleotides it translocates through the pore before it dissociates from the DNA, ending the event. Processivity can in principle be a function of various experimental conditions, including temperature, substrate and salt concentration, pH, and applied force (i.e. applied voltage). Hel308's activity is insensitive to force over the range of forces (voltages) we apply in our experiments, so its stepping rate and processivity should not change with the variable applied voltage.

We observed Hel308's processivity in both the constant- and variable-voltage conditions by looking at the read lengths obtained on our ΦX-174 construct. Specifically, we looked at read lengths on the larger, 5042 bp fragment, as this fragment is long enough that nearly all reads terminated due to the helicase unbinding from the DNA prior to reaching the end of the strand. Based on alignments of the reads to the ΦX-174 reference, we investigated 49 constant-voltage reads and 50 variable-voltage reads of the long fragment, all starting at the same location in the genome (at the AvaII cut site, described above). Hel308 shows little ability to unwind dsDNA in our experimental conditions, so all reads began at the loading site and only progressed once the duplex strand had been sheared away by the pore. The read survival fraction as a function of read length was calculated as the number of reads reaching a given position in ΦX-174 over the total number of reads. We found that the survival fraction $f$ as a function of read length l was well modeled by a single exponential function of the form $$f(l) = e^{\frac{l}{l_p}},$$

where $l_p$ is the characteristic processivity of the enzyme.

Figure 24:
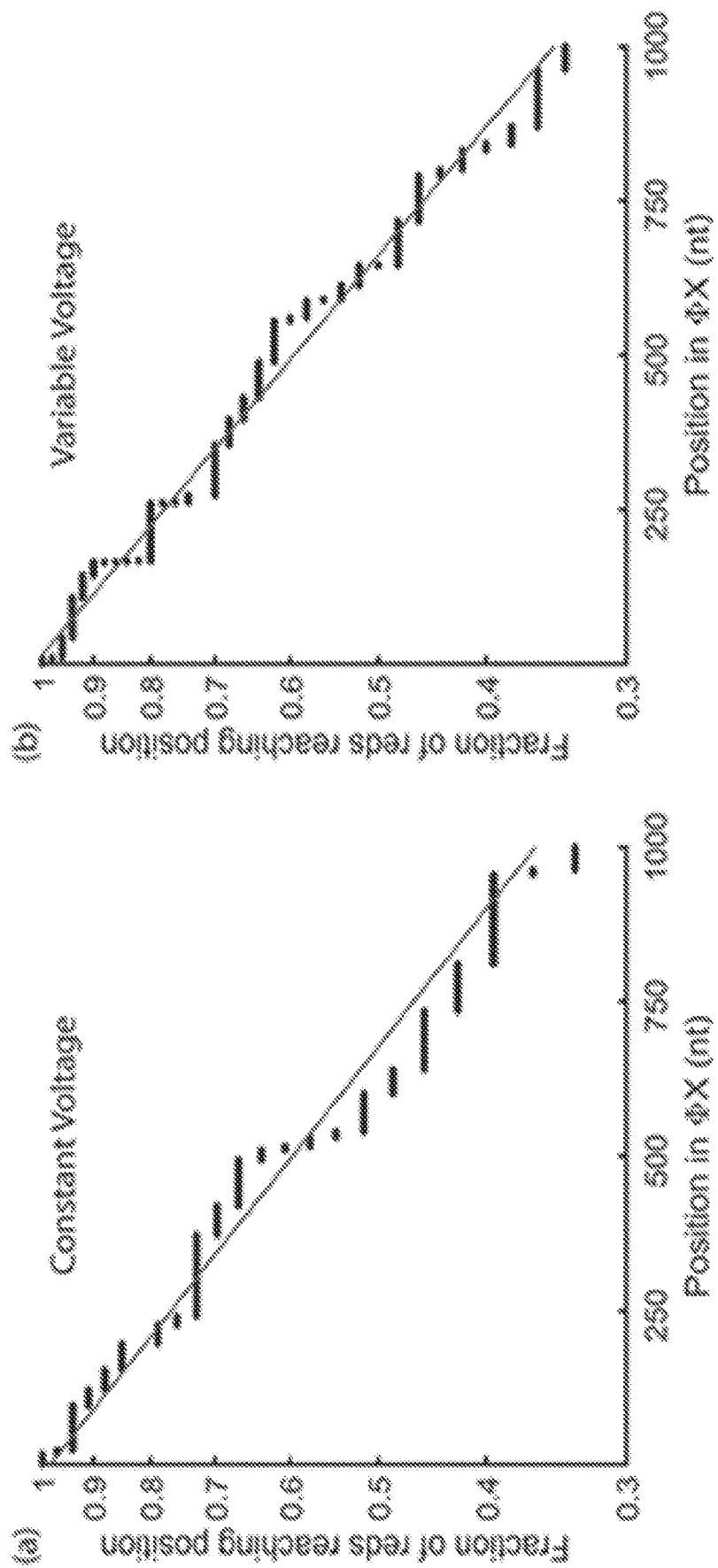
FIG. 24 is a chart that illustrates an example embodiment of Hel308 processivity in constant voltage (a) and variable voltage (b) sequencing conditions according to various aspects of the present disclosure.

FIG. 24 is a chart that illustrates an example embodiment of Hel308 processivity in constant voltage (a) and variable voltage (b) sequencing conditions according to various aspects of the present disclosure. The fraction of reads (all starting from the same cut site in ΦX-174) reaching a given position in the genome is plotted as black dots on a logarithmic y-scale. We see an exponential fall-off in read survival, indicating a read-termination process dominated by a single off-rate. The diagonal line shows the best-fit single exponential model of the form $f(l)=e^{-1/l_p}$. The best fit for constant voltage is given by $l_p=999$ nt, the best fit for variable voltage is given by $l_p=933$ nt. The processivity in the two conditions is identical within statistical uncertainty.

The single-exponential form of the survival fraction indicates that Hel308 dissociation from the ssDNA track in our experiments is dominated by a single rate-limiting step. From our data, we found a best fit processivity of $l_p=999\pm174$ nt for the constant-voltage data and $l_p=933\pm132$ nt for the variable-voltage data. The processivity in the two conditions is identical within statistical uncertainty, meaning the change from constant to variable voltage has no effect on read length.

Figure 25:
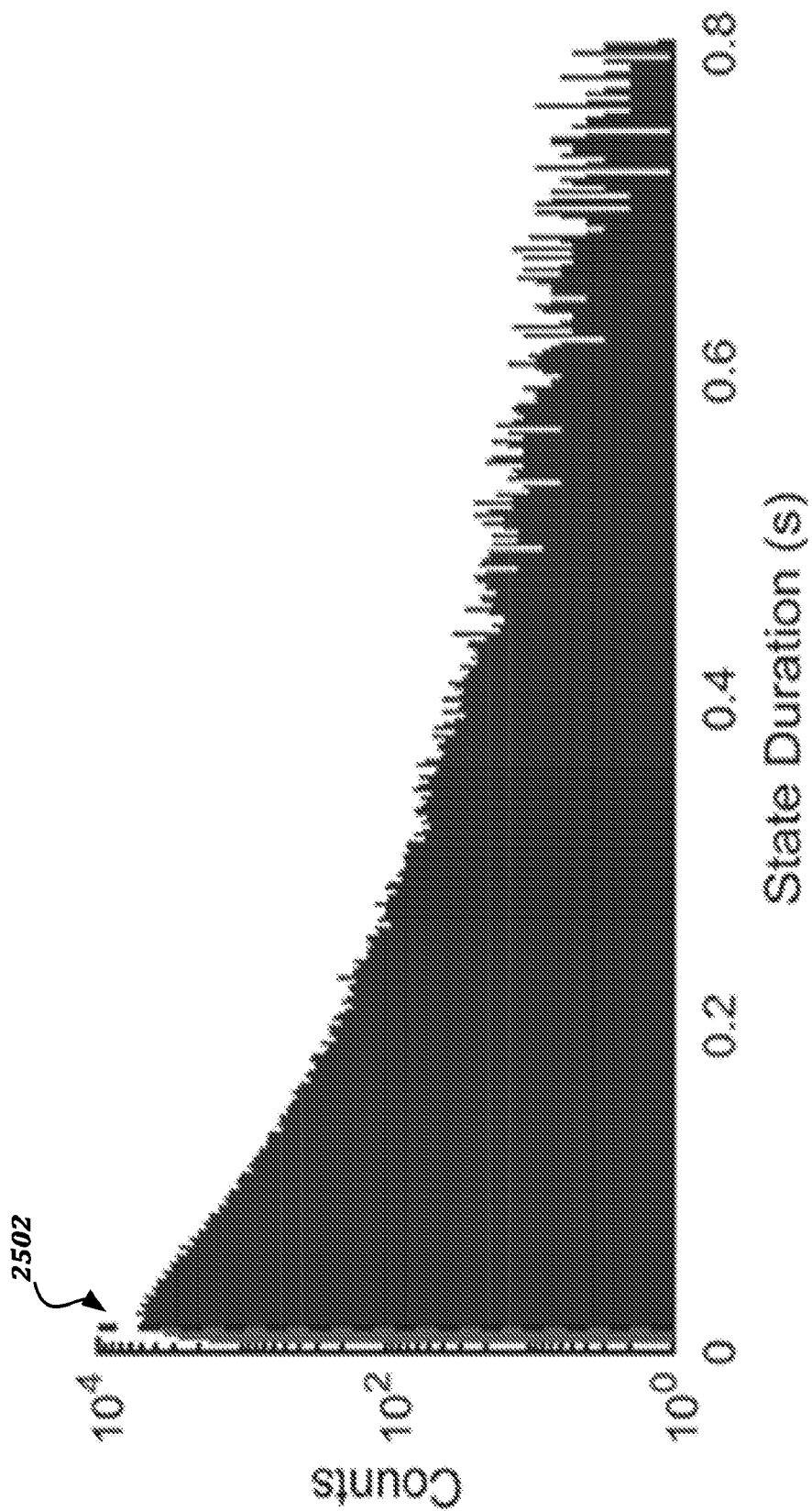
FIG. 25 is a chart that illustrates the distribution of step durations for Hel308 in the sequencing experimental conditions used by the present disclosure.

FIG. 25 is a chart that illustrates the distribution of step durations for Hel308 in the sequencing experimental conditions used by the present disclosure. We need 3 complete voltage cycles (15 ms) to accurately estimate the covariance of the 3 principal components for a state, otherwise we must take a default value for the covariance for the state. Over 90% of states are long enough to accurately estimate the covariance. A small fraction (Φ0%, to the left of the vertical dashed line 2502) are too short and are assigned a default covariance value.

States shorter than a full voltage cycle (5 ms) will not be detected by the change-point detection algorithm and ultimately manifest as skips in the final data. However, for these conditions such short states should make up only a small minority of the total Hel308 states. Long term, it may be desirable to use a faster enzyme (or experimental conditions in which Hel308 steps faster) in to increase throughput and decrease the per-read time. To accomplish this in variable-voltage setting, one may increase the variable-voltage cycle frequency. One difficulty in increasing the cycle frequency is that the capacitive current increases with increasing rate of change in the voltage. If the capacitive current becomes too large, it could rail the amplifier (rail is ±1 nA), resulting in a loss of signal.

This issue can be addressed in multiple ways. First, reducing bilayer capacitance is a straightforward way of reducing the capacitive current. A commercial sequencing device may be dramatically miniaturized compared to the experiments run in a laboratory, and may likely use an automated method of bilayer formation. These automatically-formed bilayers can in principle be much smaller (lower capacitance) than the hand-painted bilayers used in this work.

Second, we have some room to reduce the range of the voltage sweep without compromising the efficacy of the variable-voltage signal. The 100-200 mV swing currently in use gives us more than enough state-to-state overlap to identify and correct enzyme missteps. A smaller voltage range should still provide adequate overlap, while reducing the rate of voltage change and thus the size of the capacitive current.

Finally, on-line methods can be used to compensate for the capacitive signal. The injection of an in-phase square wave current into the system to counteract the square wave contribution of the capacitance would allow us to take the variable-voltage method to much higher cycle frequencies.

Sequencing Verification Experiment

We tested the relative performances of our constant-voltage and variable-voltage sequencing methods by using both methods to sequence DNA from the pET-28a vector. The pET-28a vector was chosen as it represented a readily available genomic DNA sequence and was not involved in our 6-mer model construction, thus avoiding the risk of over-training artificially boosting our sequencing numbers. Given Hel308's limited processivity, an experiment in which all reads began from the same start point in pET-28a would be unlikely to generate good coverage throughout the sequence and instead concentrate most reads on the same ~1000 base pairs nearest the start point. To get broad coverage throughout the sequence, and to get reads of both the sense and antisense strands, we fragmented the pET-28a sequence using a double restriction digest. Digestion gave us a variety of 100-1000 base fragments for our sequencing experiments (Table S1), which were generated, then prepared for Hel308 sequencing experiments as follows:

1. The pET-28a vector was digested using the NspI and Sau3aI restriction enzymes (New England Biolabs). We used 3.5 μL of $$10000\frac{U}{mL} NspI$$

and 7 μL of $$5000\frac{U}{mL} Sau3aI$$

per 17.5 μg of vector DNA. Following digestion, fragments were cleaned on DNA Clean and Concentrator column (Zymo Research).

2. Following digestion, we prepared 4 distinct adapter constructs for ligation. The four constructs were
   (a) Sau3aI threading adapter, composed of the Sau3aI threading strand and the Sau3aI cholesterol blocker (Table S3)
   (b) Sau3aI loading adapter, composed of the Sau3aI loading strand and the Sau3aI loading blocker
   (c) NspI threading adapter, composed of the NspI threading strand and the NspI cholesterol blocker
   (d) NspI loading adapter, composed of the NspI loading strand and the NspI loading blocker We require four adapter constructs as each pET-28a fragment needs a threading adapter to facilitate capture into the pore and a loading adapter to facilitate Hel308 loading onto the DNA. Each of the two cutsites needs its own set of loading and threading adapters as the two restriction enzymes leave different sticky-end overhangs. Adapters were prepared individually by mixing equimolar portions of the two constituent oligos and annealing using standard annealing protocols.

3. We ligated the several adapters to the pET-28a fragments by mixing the fragmented DNA with the annealed adapter constructs in approximately equimolar ratios, then incubating with T4 DNA ligase. Following ligation, the final products were purified using another DNA Clean and Concentrator column.

There are a few issues with the above-described preparation procedure to be considered in estimating the overall yield and in conducting downstream analysis. First, due to the palindromic nature of both the NspI and Sau3aI cutsites, we are not guaranteed to correctly get one each of the loading and threading adapters ligated to each fragment. Indeed, 25% of the total fragments will have the correct adapters for a sense strand read, 25% will have the correct adapters for an antisense strand read, and 50% will have either 2 loading adapters or 2 threading adapters and will be unlikely to produce reads. Even with this 50% drop off in the effective yield of this preparation procedure, we were still able to generate plenty of DNA to collect the data needed.

On this same note, the loading and threading adapters for each cutsite are themselves self-complementary at their overhanging sticky ends. This can lead to the formation of so-called adapter dimers, where two adapters ligate to each other. When a loading adapter ligates to a threading adapter, we create a DNA construct that can both load Hel308 and thread into the pore, and so is likely to be read. We see a population of these dimers in our experiments, and discard them from later analysis based on their characteristically short length and recognizable pattern of states.

The final drawback also stems from the palindromic nature of the restriction cutsites. The sticky-end overhangs left on the pET-28a fragments after digestion are self-complementary, which can lead to chimera formation. Chimeras occur when different fragments from disparate parts of the pET-28a reference sequence ligate together. We see a population of these chimeras in our reads. There is nothing intrinsically wrong with the chimera reads, but determining the base calling accuracy for these reads is more difficult. In these cases, we piece together the ground truth reference sequence by separately aligning the smaller fragments composing the chimera to find which parts of the reference sequence have been stitched together.

The called sequence is then compared against this stitched-together ground truth sequence to evaluate the read accuracy.

TABLE 1 pET-28a fragments from double digest with NspI and Sau3aI.

| Fragment Length (bp) | Left Cutsite | Right Cutsite |
|---|---|---|
| 826 | Sau3aI | Sau3aI |
| 570 | Sau3aI | NspI |
| 409 | Sau3aI | Sau3aI |
| 389 | Sau3aI | Sau3aI |
| 373 | Sau3aI | Sau3aI |
| 367 | NspI | NspI |
| 346 | Sau3aI | Sau3aI |
| 292 | NspI | NspI |
| 252 | Sau3aI | Sau3aI |
| 207 | Sau3aI | Sau3aI |
| 178 | Sau3aI | Sau3aI |
| 145 | NspI | Sau3aI |
| 132 | Sau3aI | Sau3aI |
| 130 | Sau3aI | Sau3aI |
| 104 | Sau3aI | Sau3aI |
| shorter fragments | | |

DNA Sequences

Tables 2 and 3 contain a list of the short custom DNA sequences used in our sequencing and DNA stretching experiments. In addition to these short sequences, we used the λ phage (Promega) and ΦX-174 genomes (New England Biolabs) as well as the pET-28a vector (from collaborators).

TABLE 2

Table of short DNA sequences used for constructing the variable-voltage 6-mer model.

| DNA Construct Name | SEQ NO | Sequence (5' →3') With modifications indicated in underline |
|---|---|---|
| ΦX174 Experiments | | 1    6    11   16   21   26   31   36   41   46   51 |
| ΦX174 threading strand | 1 | PXAAA AAAAC CTTCC XCCTT CCCAT CATCA TCAGA TCTCA CGCGG TGCA |
| ΦX174 cholesterol blocker | 2 | PCCGC GTGAG ATCTG AAAAA TTTAA ACCCA AAXZ |
| ΦX174 loading strand | 3 | PGACC CGCCA AGTAC AAGTA AGCCT ACGCC TACGG TTTTT TTTTT TTTTT TTTTT |
| ΦX174 loading blocker | 4 | CCGTA GGCGT AGGCT TACTT GTACT TGGCG G |
| λ-phage Experiments | | 1    6    11   16   21   26   31   36   41   46   51 |
| λ threading strand | 5 | PTACT ACTAC TACTA CTACX XTTTT GAGCC TCTCA CTATC GCATT CTCAT GCAGG T |
| λ cholesterol blocker | 6 | PCCTG CATGA GAATG CGATA GTGAG ATCGT AGCCQ QQQZ |
| λ loading strand | 7 | PGGAC GTACT CTTAC GCTAT CACTC TTCGT AGCC |
| λ loading blocker | 8 | AGAGT GATAG CGTAA GAGTA CGTCC T |
| Missing 6-mer Experiments | | 1    6    11   16   21   26   31   36   41   46   51<br>56   61   66   71   76   81   86   91   96   101  106<br>111  116  121  126  131  136  141  146  151  156 |

TABLE 2-continued

Table of short DNA sequences used for constructing the variable-voltage 6-mer model.

| DNA Construct Name | SEQ NO | Sequence (5'→3') With modifications indicated in underline |
|---|---|---|
| Fill-in template 1 | 9 | PTACT ACTAC TACTA CTACX XTTTT TTGGC GCTTC ATACA GCCGC GCCGG CGAGA TTTTG GCGAG ACAGG CACGC GCGAG CCCAA TCTAT TTTCA ATCTA CGTAT ACTAG GGGGT TCTAG TACTT TTTCT CACTA TCGCA TTCTC ATGCA GGTCG TAGCC |
| Fill-in template 2 | 10 | PTACT ACTAC TACTA CTACX XTTTT CTAGT ACACT AGACT AGTCC CTACT ACGAT TTTTC TACGA TTAGG GCCCT ATCTA ATCTA GAGTT TTTCT AGAGT AGGGA CCCCG GGACT CCCTT GTATT TTTCT CACTA TCGCA TTCTC ATGCA GTCG TAGCC |
| Fill-in template 3 | 11 | PTACT ACTAC TACTA CTACX XTTTT CCTTG TAGAT CCTAT ACGGA CGGGG TCTCT TTTTG GTCTC TAGCG CTCGA ATGTG TCGAC ACCTT TTTGA CACCT CAGAG ACCTA GCTAG GCTAG TGTTT TTTCT CACTA TCGCA TTCTC ATGCA GGTCG TAGCC |
| Fill-in template 4 | 12 | PTACT ACTAC TACTA CTACX XTTTT CTAGT GTACA CCTCG GACCG GTGCC CTCGA TTTTC CCTCG AGAGG ACCAT GCTAG CCCCC CGCTT TTTCC CCGCT ATACA AGTAC CCGAG TTAGA ACTTT TTTCT CACTA TCGCA TTCTC ATGCA GGTCG TAGCC |
| Fill-in template 5 | 13 | PTACT ACTAC TACTA CTACX XTTTT TAGAA CTAGG ATAGG GTGGG GCACA TACCT TTTTC ATACC TAGGT CCGAA TCGAT CTTAG CCTAT TTTTA GCCTA AGGGT AGACG TGATT GGGCC TACTT TTTCT CACTA TCGCA TTCTC ATGCA GGTCG TAGCC |
| Fill-in template 6 | 14 | PTACT ACTAC TACTA CTACX XTTTT CATAC GTAGC ATTTT TCATA GGCCC CATTT TTCAT CCCGC GCATT TTTCA TCCTA CGCAT TTTTT CTCAC TATCG CATTC TCATG CAGGT CGTAG CC |
| Fill-in cholesterol blocker | 15 | CCTGC ATGAG AATGC GATAG TGAGA QQQQZ |

Legend: P = phosphate, Q = 18 carbon spacer, X = abasic site, Z cholesterol tag

TABLE 3

Table of short DNA sequences used for measuring DNA stretching and for validating variable-voltage sequencing performance.

| DNA Construct Name | SEQ NO | Sequence (5'→3') With modifications indicated in underline |
|---|---|---|
| pet28a Sequencing Experiments | | 1   6   11  16  21  26  31  36  41  46  51 56  61  66  71 |
| Sau3aI threading strand | 16 | PTACT ACTAC TACTA CTACT ACTAC TACTA CXXTT TTATT GAAGT GCAGT ACTTT ACTAA TTATT GCTTT T |
| Sau3aI cholesterol blocker | 17 | PGATC AAAAG CAATA ATTAG TAAAG TACTG CACTT CAATQ QQQZ |
| Sau3aI loading strand | 18 | PGATC ATTGA AGTGC AGTAC TTTAC TAATT ATTGC TTTTT CTGAG CC |
| Sau3aI loading blocker | 19 | AAAAG CAATA ATTAG TAAAG TACTG CACTT CAAT |
| NspI threading strand | 20 | PTACT ACTAC TACTA CTACT ACTAC TACTA CXXTT TTATT GAAGT GCAGT ACTTT ACTAA TTATT GCTTT TCATG |
| NspI cholesterol blocker | 21 | PAAAA GCAAT AATTA GTAAA GTACT GCACT TCAAT QQQQZ |
| NspI loading strand | 22 | PATTG AAGTG CAGTA CTTTA CTAAT TATTG CTTTT TCTGA GCC |
| NspI loading blocker | 23 | AAAAG CAATA ATTAG TAAAG TACTG CACTT CAATC ATG |
| DNA Stretching Experiments | | 1   6   11  16  21  26  31  36  41  46  51 56  61  66  71  76  81  86  91  96  101 106 111 116 121 126 131 136 141 146 151 156 |

TABLE 3-continued

Table of short DNA sequences used for measuring DNA stretching and for validating variable-voltage sequencing performance.

| DNA Construct Name | SEQ NO | Sequence (5' →3') With modifications indicated in underline |
|---|---|---|
| Stretching read strand | 24 | PTACT ACTAC TACTA CTACX XTTTT TTCTG CAGTG CAGTT TGCTT TGCGA AATGA AACTG CAGTT TGCGA AATTG CAGTT TGCGA AAGTT TGCTG CACGA AATTT TGCTG CAGGA AATTT TTTTC TCACT ATCGC ATTCT CATGC AGGTC CGAGC C |
| Stretching cholesterol blocker | 25 | CCTGC ATGAG AATGC GATAG TGAGA QQQQZ |

Legend: P = phosphate, Q = 18 carbon spacer, X = abasic site, Z cholesterol tag

Experimental Statistics

Statistics for the variable-voltage and constant-voltage experiments conducted to generate the 6-mer model, validate the performance of variable-voltage sequencing, and measure the stretching response of DNA in MspA in response to voltage are summarized in Table S4.

TABLE S4

Experimental statistics. The number of pores run and the total number of enzyme-controlled DNA translocation events collected are summarized for the experiments underpinning the development and demonstration of variable-voltage sequencing

| Experiment Description | Enzyme control mechanism | DNA Sequence | Number of Pores | Number of Events |
|---|---|---|---|---|
| 6-mer model building, SVM training | He1308 | OX174 | 19 | 155 |
| 6-mer model building | He1308 | X phage | 46 | 128 |
| 6-mer model building | He1308 | Fill-in template 1 | 3 | 18 |
| 6-mer model building | He1308 | Fill-in template 2 | 3 | 28 |
| 6-mer model buildingr | He1308 | Fill-in template 3 | 7 | 38 |
| 6-mer model building | He1308 | Fill-in template 4 | 6 | 30 |
| 6-mer model building | He1308 | pET28a | 4 | 25 |
| 6-mer model building | He1308 | pET28a | 4 | 33 |
| Variable-voltage sequencing | He1308 | Fill-in template 5 | 10 | 97 |
| Constant-voltage sequencing | He1308 | Fill-in template 6 | 21 | 31 |
| DNA stretching | He1308 | Stretching strand | 2 | 18 |

Example Computing Device

Figure 30:
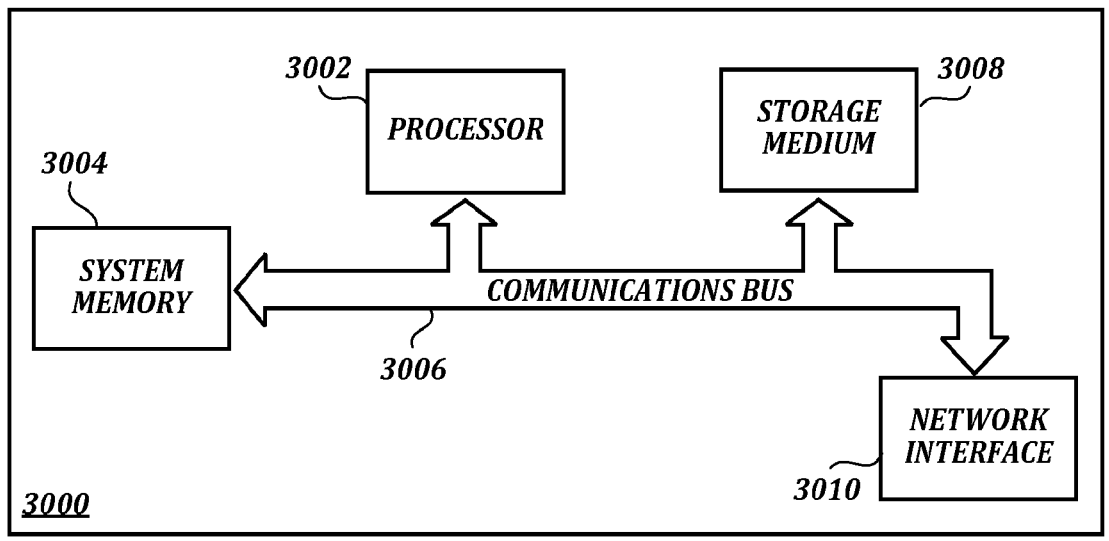
FIG. 30 is a block diagram that illustrates aspects of an exemplary computing device appropriate for use as a computing device of the present disclosure.

FIG. 30 is a block diagram that illustrates aspects of an exemplary computing device 3000 appropriate for use as a computing device of the present disclosure. While multiple different types of computing devices were discussed above, the exemplary computing device 3000 describes various elements that are common to many different types of computing devices. While FIG. 30 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 3000 may be any one of any number of currently available or yet to be developed devices.

In its most basic configuration, the computing device 3000 includes at least one processor 3002 and a system memory 3004 connected by a communication bus 3006. Depending on the exact configuration and type of device, the system memory 3004 may be volatile or nonvolatile memory, such as read only memory ("ROM"), random access memory ("RAM"), EEPROM, flash memory, or similar memory technology. Those of ordinary skill in the art and others will recognize that system memory 3004 typically stores data and/or program modules that are immediately accessible to and/or currently being operated on by the processor 3002. In this regard, the processor 3002 may serve as a computational center of the computing device 3000 by supporting the execution of instructions.

As further illustrated in FIG. 30, the computing device 3000 may include a network interface 3010 comprising one or more components for communicating with other devices over a network. Embodiments of the present disclosure may access basic services that utilize the network interface 3010 to perform communications using common network protocols. The network interface 3010 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 3010 illustrated in FIG. 30 may represent one or more wireless interfaces or physical communication interfaces described and illustrated above with respect to particular components of the system 100.

In the exemplary embodiment depicted in FIG. 30, the computing device 3000 also includes a storage medium 3008. However, services may be accessed using a computing device that does not include means for persisting data to a local storage medium. Therefore, the storage medium 3008 depicted in FIG. 30 is represented with a dashed line to indicate that the storage medium 3008 is optional. In any event, the storage medium 3008 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 3004 and storage medium 3008 depicted in FIG. 30 are merely examples of computer-readable media.

Suitable implementations of computing devices that include a processor 3002, system memory 3004, communication bus 3006, storage medium 3008, and network interface 3010 are known and commercially available. For ease of illustration and because it is not important for an understanding of the claimed subject matter, FIG. 30 does not show some of the typical components of many computing devices. In this regard, the computing device 3000 may include input devices, such as a keyboard, keypad, mouse, microphone, touch input device, touch screen, tablet, and/or the like. Such input devices may be coupled to the computing device 3000 by wired or wireless connections including RF, infrared, serial, parallel, Bluetooth, Bluetooth low energy, USB, or other suitable connections protocols using wireless or physical connections. Similarly, the computing device 3000 may also include output devices such as a display, speakers, printer, etc. Since these devices are well known in the art, they are not illustrated or described further herein.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. Words such as "about" and "approximately" imply minor variation around the stated value, usually within a standard margin of error. In some embodiments, the term "about" implies variation within 10%, 9%, 8%, 7%, 6%, 5%, 4%, 3%, 2%, or 1% of the stated reference value.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

While illustrative embodiments have been illustrated and described, it will be appreciated that various changes can be made therein without departing from the spirit and scope of the invention.

The embodiments of the invention in which an exclusive property or privilege is claimed are defined as follows:

1. A computer-implemented method of determining an identity of one or more monomer subunit residues of a polymer analyte, the method comprising:
   transmitting, by a computing system, an instruction to a nanopore system that causes a voltage source of the nanopore system to generate a variable voltage between a first conductive liquid medium and a second conductive liquid medium;
   receiving, by the computing system, a raw current signal generated as a polymer analyte translocates through a nanopore of the nanopore system in response to the variable voltage;
   detecting, by the computing system, change points in the raw current signal to determine a series of states, wherein detecting change points in the raw current signal includes determining basis functions derived from a dimensionality-reduced version of the raw current signal;
   performing, by the computing system, capacitance compensation on the raw current signal for each state to create an ionic current-vs-voltage curve for each state;
   converting, by the computing system, the ionic current-vs-voltage curves to conductance-vs-voltage curves;
   performing, by the computing system, filtering for the series of states to create a series of filtered states; and
   determining, by the computing system, the identity of one or more monomer subunit residues of the polymer analyte based on the series of filtered states.

2. The computer-implemented method of claim 1, wherein detecting change points in the raw current signal includes:
   removing flicker from the raw current signal to create a flicker-free current signal; and
   using the flicker-free current signal to detect the change points.

3. The computer-implemented method of claim 1, wherein the dimensionality-reduced version of the raw current signal is generated via principal component analysis.

4. The computer-implemented method of claim 1, wherein detecting change points in the raw current signal includes using an over-fitting bias removal technique to remove over-fitting bias from a likelihood-maximization process for determining the change points, wherein the overfitting bias removal technique is at least one of a Change Point Information Criterion or an Aikaike Information Criterion.

5. The computer-implemented method of claim 1, wherein performing capacitance compensation on the raw current signal for each state to create an ionic current-vs-voltage curve for each state includes:
   determining a phase of the raw current signal based on an applied voltage signal;

binning data points in the raw current signal based on a location of each data point in the phase of the raw current signal;

averaging data points in each bin to determine an average current-voltage characteristic for up portions of the phase and for down portions of the phase;

determining a difference between the average current-voltage characteristic for up portions of the phase and the average current-voltage characteristic for down portions of the phase to find an asymmetry between the up portions and the down portions;

fitting a parabola to the asymmetry between the up portions and the down portions over a second quartile and a third quartile of the voltage to determine a residual function;

determining an up correction function and a down correction function based on the residual function;

applying the up correction function to the average current-voltage characteristic for up portions of the phase and applying the down correction function to the average current-voltage characteristic for down portions of the phase; and applying a correction based on the average current-voltage characteristics to each data point of the raw current signal to create the ionic current-vs-voltage curves.

6. The computer-implemented method of claim 1, further comprising determining one or more features for each state based on the conductance-vs-voltage curves.

7. The computer-implemented method of claim 6, wherein the conductance-vs-voltage curves include a full feature vector, and wherein determining the one or more features for each state includes, for each state, performing dimensionality reduction on the full feature vector, wherein performing dimensionality reduction includes performing a principal component analysis to determine a reduced set of descriptive features of the full feature vector.

8. The computer-implemented method of claim 1, wherein converting the ionic current-vs-voltage curves to the conductance-vs-voltage curves includes performing conductance normalization to remove any portion of the current signal not associated with a monomer subunit identity of the polymer analyte translocating through the nanopore.

9. The computer-implemented method of claim 8, wherein performing conductance normalization includes:
determining a mean conductance at each voltage over each state; and
for each state:
subtracting the mean conductance from the measured conductance of the state to obtain a reduced conductance curve;
fitting a linear model to the reduced conductance curve to obtain a slope;
linearly fitting the slope to a mean voltage of the reduced conductance curves to obtain a bias; and
subtracting the bias from the reduced conductance curve to remove the portion of the conductance that is not dependent upon monomer subunit position.

10. The computer-implemented method of claim 1, wherein performing filtering for the series of states to create a series of filtered states includes:
applying a removal filter to remove states that are not informative of the monomer subunit residues;
applying a recombination filter to remove states that represent repeated measurements of the same monomer subunit position; and
applying a reordering filter to identify and correct out-of-order states.

11. The computer-implemented method of claim 10, wherein applying the removal filter includes determining a probability that a state should be removed using a machine learning classification algorithm, wherein the machine learning classification algorithm is a support vector machine.

12. The computer-implemented method of claim 11, wherein determining the probability that the state should be removed using the machine learning classification algorithm includes determining the probability based on one or more features of the state, one or more features of a preceding state, and one or more features of a subsequent state.

13. The computer-implemented method of claim 12, wherein determining the probability that the state should be removed using the machine learning classification algorithm includes determining the probability based further on at least one of:
a value of a single conductance measurement in the state that most deviates from an overall mean conductance;
an average mean square difference between a full feature vector of the state and a reduced-dimensionality feature vector of the state; and
a score of a best match for the state against a k-mer model.

14. The computer-implemented method of claim 10, wherein applying the recombination filter to remove states that represent repeated measurements of the same monomer subunit position includes performing a Needleman-Wunsch-style alignment of each state against itself.

15. The computer-implemented method of claim 14, wherein performing the Needleman-Wunsch-style alignment of each state against itself includes:
determining step-type probabilities at each transition based on conductance curve overlap information using a machine learning classification algorithm; and
applying a self-alignment penalty to newly created states;
wherein the machine learning classification algorithm is an ensemble of support vector machines.

16. The computer-implemented method of claim 10, wherein applying the reordering filter to identify and correct out-of-order states includes:
using a machine learning classification technique to assign a probability that each transition was a step, a skip, or a backstep; and
using a dynamic programming technique to reorder the states in a most likely true order;
wherein the machine learning classification algorithm is an ensemble of support vector machines with associated logit functions.

17. The computer-implemented method of claim 1, wherein determining the identity of one or more monomer subunit residues of the polymer analyte based on the series of filtered states includes performing sequencing using a hidden Markov model (HMM) solver.

18. The computer-implemented method of claim 17, wherein performing sequencing using the HMM solver includes:
using information regarding a likelihood of a sequencing enzyme used to translocate the polymer analyte through the nanopore in a given state to help determine state probabilities for a score matrix used with the HMM solver.

19. The computer-implemented method of claim 17, wherein performing sequencing using the HMM solver includes:
using probabilities of steps, skips, and bad levels determined while performing filtering on the series of states to help determine state probabilities for a score matrix used with the HMM solver.

20. A non-transitory computer-readable medium having computer-executable instructions stored thereon that, in response to execution by one or more processors of a computing system, cause the computing system to perform actions for determining an identity of one or more monomer subunit residues of a polymer analyte, the actions comprising:

- transmitting, by the computing system, an instruction to a nanopore system that causes a voltage source of the nanopore system to generate a variable voltage between a first conductive liquid medium and a second conductive liquid medium;
- receiving, by the computing system, a raw current signal generated as a polymer analyte translocates through a nanopore of the nanopore system in response to the variable voltage;
- detecting, by the computing system, change points in the raw current signal to determine a series of states;
- performing, by the computing system, capacitance compensation on the raw current signal for each state to create an ionic current-vs-voltage curve for each state;
- converting, by the computing system, the ionic current-vs-voltage curves to conductance-vs-voltage curves;
- determining, by the computing system, one or more features for each state based on the conductance-vs-voltage curves, wherein the conductance-vs-voltage curves include a full feature vector, and wherein determining the one or more features for each state includes, for each state, performing dimensionality reduction on the full feature vector to determine a reduced set of descriptive features of the full feature vector;
- performing, by the computing system, filtering for the series of states to create a series of filtered states; and
- determining, by the computing system, the identity of one or more monomer subunit residues of the polymer analyte based on the series of filtered states.

* * * * *